United States Patent
Tangy et al.

(10) Patent No.: US 10,980,873 B2
(45) Date of Patent: Apr. 20, 2021

(54) USE OF A GENETICALLY MODIFIED INFECTIOUS MEASLES VIRUS WITH ENHANCED PRO-APOPTOTIC PROPERTIES (MV-DELTAC VIRUS) IN CANCER THERAPY

(71) Applicants: INSTITUT PASTEUR, Paris (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR); UNIVERSITE DE NANTES, Nantes (FR)

(72) Inventors: Frédéric Tangy, Les Lilas (FR); Marc Gregoire, Nantes (FR); Jean-François Fonteneau, Nantes (FR); Jean-Baptiste Guillerme, Nantes (FR); Chantal Combredet, Paris (FR)

(73) Assignees: INSTITUT PASTEUR, Paris (FR); CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM), Paris (FR); UNIVERSITE DE NANTES, Nantes (FR)

( * ) Notice: Subject to any disclaimer, the term of this patent is extended or adjusted under 35 U.S.C. 154(b) by 0 days.

(21) Appl. No.: 16/429,571

(22) Filed: Jun. 3, 2019

(65) Prior Publication Data
US 2020/0016260 A1    Jan. 16, 2020

Related U.S. Application Data

(60) Division of application No. 15/880,133, filed on Jan. 25, 2018, now Pat. No. 10,314,905, which is a continuation of application No. 14/762,559, filed as application No. PCT/EP2014/051063 on Jan. 20, 2014, now Pat. No. 9,889,193.

(30) Foreign Application Priority Data

Jan. 24, 2013 (EP) .................................... 13305086

(51) Int. Cl.
| | |
|---|---|
| A61K 39/165 | (2006.01) |
| A61K 35/768 | (2015.01) |
| C12N 7/00 | (2006.01) |
| A61K 35/15 | (2015.01) |
| A61K 39/00 | (2006.01) |

(52) U.S. Cl.
CPC ............ *A61K 39/165* (2013.01); *A61K 35/15* (2013.01); *A61K 35/768* (2013.01); *C12N 7/00* (2013.01); *A61K 2039/5154* (2013.01); *A61K 2039/5254* (2013.01); *C12N 2760/18421* (2013.01); *C12N 2760/18432* (2013.01); *C12N 2760/18434* (2013.01); *C12N 2760/18462* (2013.01)

(58) Field of Classification Search
None
See application file for complete search history.

(56) References Cited

U.S. PATENT DOCUMENTS

| | | | |
|---|---|---|---|
| 9,023,643 B2* | 5/2015 | Gauvrit | A61K 39/12 435/325 |
| 9,399,062 B2* | 7/2016 | Richardson | A61K 31/713 |
| 9,889,193 B2* | 2/2018 | Tangy | C12N 7/00 |
| 10,314,905 B2* | 6/2019 | Tangy | C12N 7/00 |
| 2010/0278872 A1* | 11/2010 | Gauvrit | A61K 39/12 424/277.1 |

FOREIGN PATENT DOCUMENTS

| | | |
|---|---|---|
| WO | 2009/047331 | 4/2009 |
| WO | 2009/047331 A1 | 4/2009 |
| WO | 2012/022495 A1 | 2/2012 |

OTHER PUBLICATIONS

Short et al., Mol Cancer Ther 2009;8(8):2096-102 (Year: 2009).*
Jiménez-Baranda et al., The Journal of Clinical Investigation vol. 122, No. 2, pp. 481-484 (Year: 2012).*
H Li et al: "Oncolytic measles viruses encoding interferon [beta] and the thyroidal sodium iodide symporter gene for mesothelioma virotherapy", Cancer Gene Therapy, vol. 17, No. 8, Apr. 9, 2010, pp. 550-558.
Radecke, F. et al.: The nonstructural C protein is not essential for multiplication of Edmonston B strain measles virus in cultured cells, Virology, vol. 217, 1996, pp. 418-421.
K. Takeuchi et al: "Stringent Requirement for the C Protein of Wild-Type Measles Virus for Growth both In Vitro and in Macaques", Journal of Virology, vol. 79, No. 12, May 26, 2005, pp. 7838-7844.

(Continued)

*Primary Examiner* — Shanon A. Foley
*Assistant Examiner* — Myron G Hill
(74) *Attorney, Agent, or Firm* — Arrigo, Lee, Guttman & Mouta-Bellum LLP

(57) ABSTRACT

The invention relates to a genetically modified infectious measles virus derived from a live-attenuated measles virus strain, in which the gene encoding the viral accessory C protein has been knocked out (MV-deltaC). It concerns in particular the use of said genetically modified infectious MV-deltaC in the treatment of malignant tumour or cancer conditions, and for the preparation of agents or compositions for such treatment.

10 Claims, 30 Drawing Sheets

Specification includes a Sequence Listing.

(56) References Cited

OTHER PUBLICATIONS

Valsamakis A et al: "Recombinant measles viruses with mutations in the C, V, or F gene have altered growth phenotypes in vivo", Journal of Virology, vol. 72, No. 10, Oct. 1, 1998, pp. 7754-7761.
P. Devaux et al: "Attenuation of V- or C-Defective Measles Viruses: Infection Control by the Inflammatory and Interferon Responses of Rhesus Monkeys", Journal of Virology, vol. 82, No. 11, Apr. 2, 2008, pp. 5359-5367.
J.-B. Guillerme et al: "Measles Virus Vaccine-Infected Tumor Cells Induce Tumor Antigen Cross-Presentation by Human Plasmacytoid Dendritic Cells", Clinical Cancer Research, vol. 19, No. 5, Jan. 21, 2013, p. 1147-1158.
G Ungerechts et al: "Mantle cell lymphoma salvage regimen: synergy between a reprogrammed oncolytic virus and two chemotherapeutics", Gene Therapy, vol. 17, No. 12, Aug. 5, 2010 (Aug. 5, 2010), pp. 1506-1516.
Xin Meng et al: "Enhanced Antitumor Effects of an Engineered Measles Virus Edmonston Strain Expressing the Wild-type N, P, L Genes on Human Renal Cell Carcinoma",Molecular Therapy, vol. 18, No. 3, Jan. 5, 2010 (Jan. 5, 2010), pp. 544-551.
A. M. Toth et al: "Protein Kinase PKR Mediates the Apoptosis Induction and Growth Restriction Phenotypes of C Protein-Deficient Measles Virus", Journal of Virology, vol. 83, No. 2, Nov. 12, 2008 (Nov. 12, 2008), pp. 961-968.
J. Tel et al: "Human plasmacytoid dendritic cells efficiently cross-present exogenous Ags to CD8+ T cells despite lower Ag uptake than myeloid dendritic cell subsets", Blood, vol. 121, No. 3, Dec. 4, 2012 (Dec. 4, 2012), pp. 459-467.
Gauvrit, A. et al.: Cancer Research, vol. 68, No. 12, Jun. 15, 2008 , pp. 4882-4892.
Jean-Francois Fonteneau et al: "Attenuated measles virus used as an oncolytic virus activates myeloid and plasmacytoid dendritic cells", Onco Immunology, vol. 2, No. 5, May 1, 2013 (May 1, 2013), pp. e24212-1.
J. Tel et al: "Natural Human Plasmacytoid Dendritic Cells Induce Antigen-Specific T-Cell Responses in Melanoma Patients", Cancer Research, vol. 73, No. 3, Jan. 23, 2013 (Jan. 23, 2013), pp. 1063-1075.
P. Msaouel et al., "Attenuated oncolytic Measles Virus strains as cancer therapeutics," Curr Pharm Biotechnol. Jul. 1, 2012; 13(9): 1732-1741.
Notice of Reasons for Rejection, Japanese Application No. 2015-554120, dated Jul. 15, 2017.
Nakamura, et al., Drug Delivery System, 2009, 24, 599-607.
Peng, et al., Cancer Research, 2002, 62, 4656-4662.
Short, et al., Mol. Cancer Ther. 2009;8(8):2096-102.

* cited by examiner

→ MV
→ MV-P$_{G954}$
→ MV-deltaV
→ MV-deltaC

MV  MV-deltaC

FIG. 4

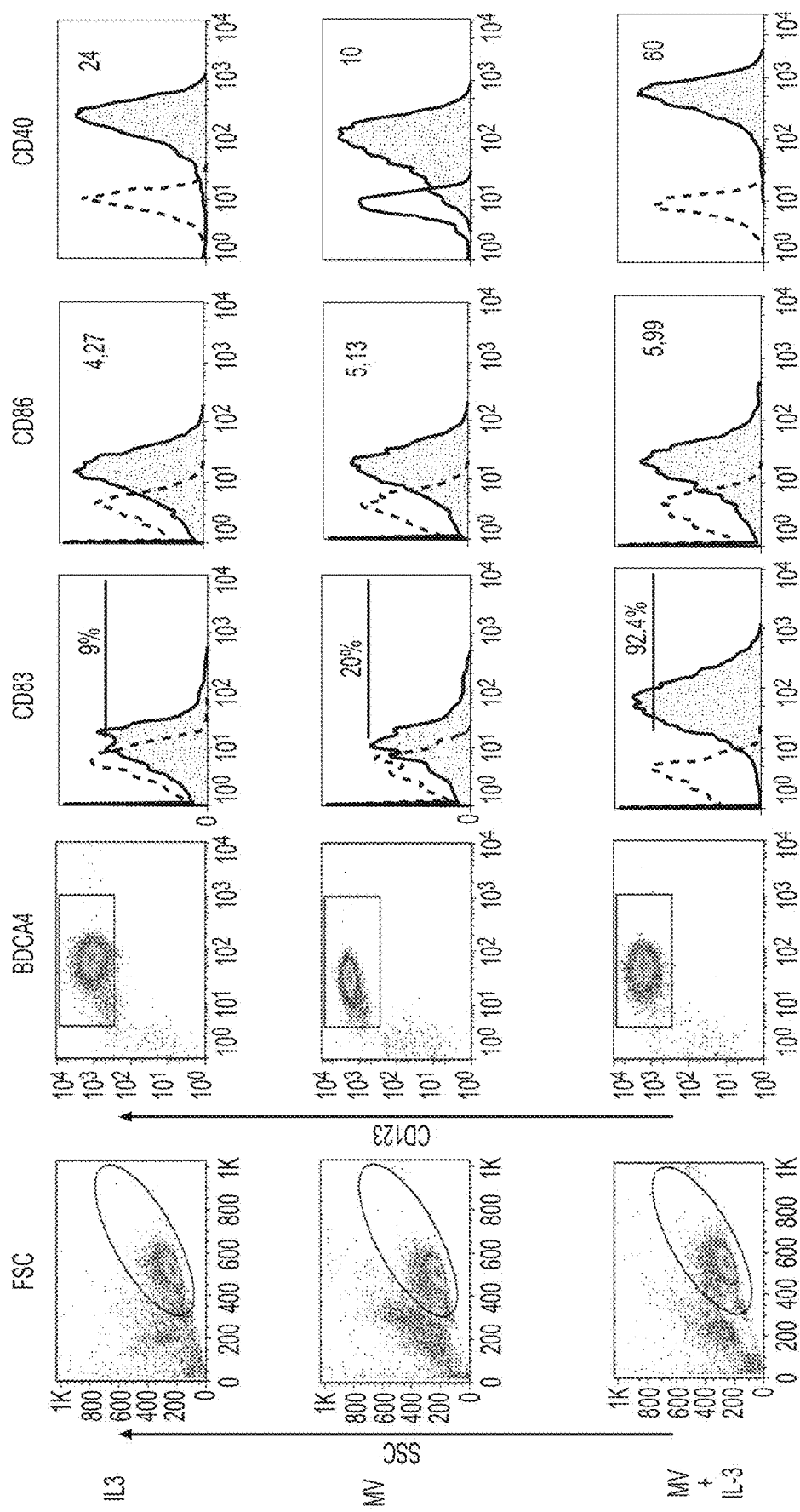
FIG. 13A (first part)

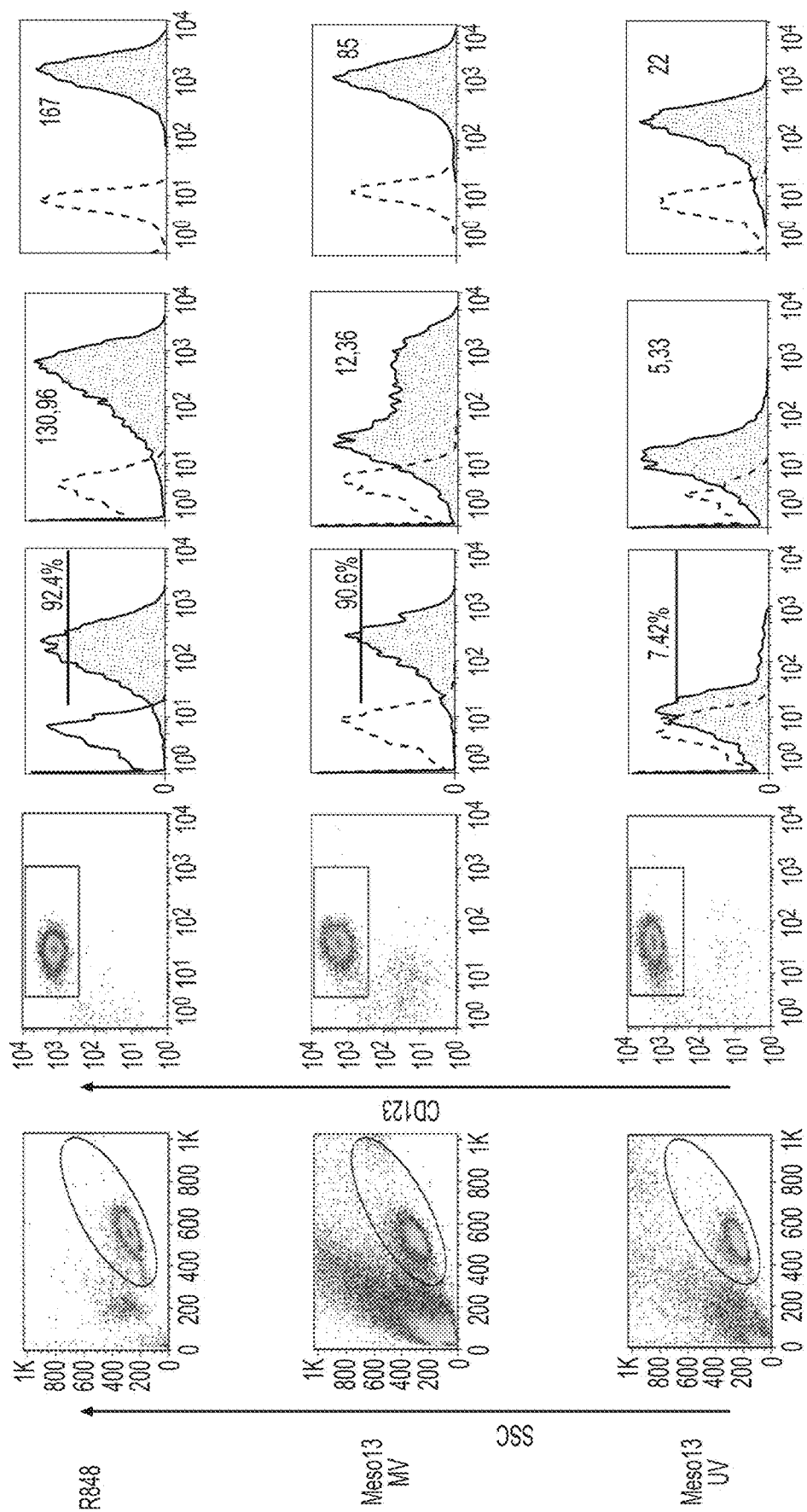
FIG. 13A (second part)

USE OF A GENETICALLY MODIFIED INFECTIOUS MEASLES VIRUS WITH ENHANCED PRO-APOPTOTIC PROPERTIES (MV-DELTAC VIRUS) IN CANCER THERAPY

SEQUENCE LISTING

The instant application contains a Sequence Listing which has been submitted electronically in ASCII format and is hereby incorporated by reference in its entirety. Said ASCII copy, created on Jan. 27, 2014, is named eolf-seql.txt and is 53,965 bytes in size.

FIELD OF THE INVENTION

The invention relates to a genetically modified infectious measles virus derived from a live-attenuated measles virus strain, in which the gene encoding the viral accessory C protein has been knocked out (MV-deltaC). It concerns in particular the use of said genetically modified infectious MV-deltaC in the treatment of malignant tumour or cancer conditions, and for the preparation of agents or compositions for such treatment.

BACKGROUND OF THE INVENTION

Malignant mesothelioma is a rare and highly aggressive cancer, resistant to usual curative treatments. The development of the malignant pleural mesothelioma is mostly linked to a prolonged exposure to asbestos fibres and dusts (Kazan-Allen et al., Lung cancer, 2005, 49S1:S3-S8; Robinson et al., Lancet, 2005, 366:397-408). Melanoma is a malignant tumour that develops in melanocytes and can spread to the entire body when it is not treated. Although it represents one of the least frequent types of skin cancers, it is responsible for the most skin cancer-related deaths (Chin, L. et al., Genes Dev. 2006 20: 2149-2182). Lung adenocarcinomas are the most common kind of lung cancer, both in smokers and non-smokers and are one of the most common causes of cancer death (Travis, W. D. et al., J Thorac Oncol., 2011, 6(2), 244-285).

No strategy currently proposes a significant curative opportunity for several aggressive cancers such as malignant mesotheliomas, melanomas and lung adenocarcinomas.

Their prognoses are very poor and they are relatively refractory to all conventional treatment modalities, such as chemotherapy, radiotherapy and/or surgery. There is thus a pressing need for the development of new clinical approaches.

Cancer virotherapy is widely regarded as a new alternative for the treatment of cancers that are resistant to conventional anti-cancer therapies (Boisgerault N et al., Immunotherapy, 2010, march 2(2), 185-199). Oncolytic virotherapy has demonstrated multimodal antitumour mechanisms in both pre-clinical and a few phase I clinical anti-cancer treatments (Lech, P J and Russell, S J; Expert Review of Vaccines, 2010, 9(11):1275-1302; Galanis et al., Cancer Research, 2010, 70(3):875-882), and also in in vitro investigations (Gauvrit, A et al., Cancer Research, 2008, 68 (12), 4882-4892). Compared with cell-transfer immunotherapy, virus-vaccines have the advantage of conferring personalised anti-cancer immunity simultaneously with cytoreduction without the requirement for personalised manufacture. Additionally, virus-vaccines can be engineered to delete immunosuppressive viral components and to insert transgenes that enhance antitumour cytotoxicity and immunity (A. Gauvrit et al., Cancer Research, 2008, 68 (12), 4882-4892).

Measles virus (MV) is a non-segmented single-stranded, negative-sense enveloped RNA virus of the genus Morbillivirus within the family of Paramyxoviridae. The non-segmented genome of MV has an antimessage polarity, which results in a genomic RNA which is neither translated in vivo or in vitro nor infectious when purified. This virus has been isolated in 1954 (Enders, J. F. and Peebles, T. C., 1954, *Proc Soc Exp Biol Med,* 86(2): 277-286), and live-attenuated vaccines have been derived from this virus since then to provide vaccine strains, and in particular from the Schwarz/Moraten strain.

Transcription and replication of non-segmented (−) strand RNA viruses and their assembly as virus particles have been studied and reported especially in Fields virology (3rd edition, vol 1, 1996, Lippincott-Raven publishers—Fields B N et al.). Transcription and replication of MV do not involve the nucleus of the infected cells but rather take place in the cytoplasm of said infected cells. The genome of MV comprises genes encoding six major structural proteins from the six genes (designated N, P, M, F, H and L) and the additional two-non structural proteins from the P gene, the C and V proteins. The gene order is the following: 3', N, P (including C and V), M, F, H, and L large polymerase protein at the 5' end (FIG. 1A). The genome further comprises non-coding regions in the intergenic region M/F; this non-coding region contains approximately 1000 nucleotides of untranslated RNA. The cited genes respectively encode the leader peptide (I gene), the proteins of the nucleocapsid of the virus, i.e., the nucleoprotein (N), the phosphoprotein (P), and the large protein (L), which assemble around the genome RNA to provide the nucleocapsid. The other genes encode the proteins of viral envelope including the hemagglutinin (H), the fusion (F) and the matrix (M) proteins. The MV C protein is coded by the polycistronic P gene, it is a small (186 amino acids) and basic protein, localised both in the cytoplasm and in the nucleus (Bellini, W. J. et al., J. Vivol., 1985, 53:908-919). The role of this viral protein, described as a MV virulence factor, is not yet well understood. To determine the role of the MV C protein, a recombinant wild-type MV strain lacking expression of the C protein, based on the highly pathogenic IC-B strain and generated by using a reverse genetics system, has been used. It was suggested that the MV C protein could be involved in the assembly of viral particles, in the virus protein expression and in the delay of apoptosis of infected cells in order to establish a long term MV infection (Takeuchi, K. et al., *J. Vivol*., June 2005, 7838-7844). Although it has been reported that the MV C protein inhibits the interferon antiviral response (Shaffer, J. A. et al., *Virology,* 2003, 315:389-397), another study reached the opposite conclusion (Takeuchi, K. et al., *J. Vivol*., June 2005, 7838-7844), thereby confirming that the function of the MV C protein has not yet been well established.

Among human viruses that deserve to be tested as oncolytic agents, live-attenuated MV vaccine presents a number of advantages. Administered to hundreds of millions of children during 30 years, it is the safest and most widely used human paediatric vaccine. Attenuated strains of MV infect a large number of cell types and preferentially the transformed cancer cells. This is due to the use by MV of CD46 as a receptor frequently over-expressed in cancer cells to resist to the complement-dependant killing by natural killer cells (Naniche, D. et al., *J Vivol,* 1993, 67(10): 6025-6032; Dhiman, N. et al., *Rev Med Vivol,* 2004, 14(4):

217-229), whereas wild-type MV uses preferentially SLAM (CD150) (Tatsuo, H. et al. *Nature,* 2000, 406(6798):893-897; Anderson, B. D. et al., *Cancer Res.,* 2004, 64: 4919-4926; Schneider, U. et al., *J Virol.,* 2002, 76: 7460-7467). Interestingly, MV exhibits natural antitumour properties by specifically targeting cancer cells without infecting the healthy ones. Thus, MV demonstrates an unquestionable safety profile for application in future therapeutic protocols.

The oncolytic properties of wild-type MV are well known to a person skilled in the art (Mayo Foundation for Medical Education and Research, U.S. Ser. No. 07/854,928). Recently, clinical trials were initiated to investigate the capacity of an Edmonston MV strain to treat ovarian, glioblastoma, non-small lung cancer and multiple myeloma (see http://clinicaltrials.gov, measles and cancer keywords). The use of MV vaccines, either recombinant or chimeric, as vaccination vectors has also been described (WO2004/000876, WO2004/076619, WO2006/136697, and WO2008/078198).

This technology has also been proposed to the immuno-oncolytic treatment of mesothelioma (Gauvrit, A. et al., *Cancer Research,* 2008, 68 (12), 4882-4892). Accordingly, International Patent Application WO2009/047331 described both the oncolytic and immuno-adjuvant properties of the live-attenuated Schwarz strain of MV vaccine on a panel of epithelioid mesothelioma tumour cells. Using a rescued Schwarz strain of MV vaccine produced from an infectious cDNA clone, it was shown that MV-infected mesothelioma cells induced spontaneous monocyte-derived dendritic cell (Mo-DC) maturation and a tumour antigen-specific response.

The potential advantages of oncovirotherapy over conventional treatments include the property to induce an immune response including not only higher on-target specificity against cancer antigens (tumour associated antigens), and thus a better safety margin but also prolonged effect due to immune memory, and thus preventing relapse and metastasis. Indeed, it has been demonstrated that an immune-specific response and memory are developed after administration of MV at the site of cancer cells, in the presence of antigen-presenting cells (Massé, D. et al., *Int. J. Cancer,* 2004, 111(4), 575-580); Liu et al., *Molecular therapy: the journal of the American Society of Gene Therapy,* 2010, 18(6):1155-1162). It was demonstrated that the antitumour activity of the Schwarz MV strain acts through multiple mechanisms, including oncolysis, induction of tumour immunogenic apoptosis (danger signal expression associated with cell death) and virus-mediated syncytium formation (Gauvrit, A. et al., *Cancer Res,* 2008, 68(12), 4882-4892). In addition, the released tumour associated antigens and the inflammation resulting from viral replication have also been suggested to break the immunotolerance to tumours and induce anticancer immunity.

Despite an efficient infection, some MV-infected malignant tumour or cancer cells resist to cell death induction. Hence there is a need for the development of viruses that would help to overcome this type of resistance, and thus improve and extend the specific cell death induction of malignant tumour or cancer cells.

Dendritic cell (DC) precursors are divided into monocyte-derived dendritic cells (Mo-DCs) and plasmacytoid dendritic cells (pDCs), which display different functional properties. pDCs are a subset of DCs involved in the antiviral immune response due to their expression of Toll-like receptors (TLR) specialised in the recognition of viral nucleic acids (TLR7, TLR9) (Gilliet, M. et al., *Nat Rev Immunol.,* 2008, 8:594-606). They respond to a wide range of viruses (inter alia influenza A virus, herpes simplex virus, HIV) in terms of activation and maturation by producing large amounts of type-I interferon (IFN-$\alpha$,-$\beta$,-$\omega$). They are also able to present viral antigens to CD8+ and CD4+ T cells when they are infected by a virus (Fonteneau, J. F. et al., *Blood,* 2003, 101:3520-3526) and to cross-present viral antigens from virus-infected cells to CD8+ T lymphocytes (Di Pucchio, T. et al., *Nat Immunol.,* 2008, 9:551-557; Lui, G. et al., *PLoS One,* 2009, 4:e7111). It has also been shown that pDCs could play a beneficial role in the immune response against tumours (Drobits, B. et al., *J Clin Invest.,* 2012, 122:575-585; Liu, C. et al., *J Clin Invest.,* 2008, 118:1165-1175). As an example, in a mouse melanoma model, pDC activation and antitumour immune response were observed inside tumours after topical treatment with the TLR7 ligand, imiquimod (Drobits, B. et al., *J Clin Invest.,* 2012, 122:575-585). As MV is single-stranded RNA (ssRNA), the inventors have hypothesised that pDCs could be able to detect the MV infection of tumour cells, because of their intravacuolar TLR7 expression which recognises single-stranded RNA.

DESCRIPTION OF THE INVENTION

The inventors have surprisingly found that a genetically modified infectious measles virus derived from a live-attenuated MV strain, in which the gene encoding the viral accessory C protein has been knocked out (MV-deltaC) elicits enhanced response against malignant tumour or cancer cells and in particular has enhanced pro-apoptotic properties compared to unmodified MV. The present invention thus provides MV-deltaC and shows that it can efficiently infect and kill malignant tumour or cancer cells, such as malignant mesothelioma, melanoma and lung adenocarcinoma cells. The inventors have also shown that plasmacytoid dendritic cells contacted with lysate from MV infected malignant mesothelioma, melanoma and lung adenocarcinoma cells can activate anti-mesothelioma, anti-melanoma and anti-lung adenocarcinoma CD8 T cells. The inventors have thus proposed that the observed properties of MV-deltaC could be of interest when using it as an active compound against malignant tumour or cancer cells when MV-deltaC activates pDCs.

The present invention relates to an infectious measles virus derived from a live-attenuated measles virus strain for use in the treatment of an aggressive malignant tumour or of an aggressive cancer by activating plasmacytoid dendritic cells (pDCs), when administered to an individual diagnosed with such a tumour or a cancer condition.

The present invention also relates to a genetically modified infectious measles virus derived from a live-attenuated measles virus strain, in which the gene encoding the viral accessory C protein has been knocked out (MV-deltaC) for use in the treatment of an aggressive malignant tumour or of an aggressive cancer by activating plasmacytoid dendritic cells (pDCs), when administered to an individual diagnosed with such a tumour or a cancer condition.

The term "measles virus" is abbreviated MV and the expression "measles virus derived from a live-attenuated measles virus strain, in which the gene encoding the viral accessory C protein has been knocked out" is abbreviated MV-deltaC.

The term "encoding" used in the present application defines the ability of the nucleic acid molecules to be transcribed and where appropriate translated for product expression into selected cells or cell lines.

In the present invention, the individual is preferably a mammal, more preferably a human.

As defined herein, the expression "genetically modified" encompasses the fact that measles virus C protein synthesis is abolished in the produced, in particular rescued, genetically modified infectious MV-deltaC.

As defined herein, the expression "the gene encoding the viral accessory C protein has been knocked out" means that the expression of the gene encoding the C protein is silenced.

Inhibition of C protein synthesis is in particular achieved by silencing expression of the C protein Open Reading Frame (ORF) contained in the P gene and encoding C protein. The C protein ORF overlaps part of the P ORF in the +1 frame. Silencing of the C protein ORF is achieved in particular by a suitable mutation of the sequence of said ORF, by mutation of the second "ATG" initiation codon at the N-terminal region of the P gene. In addition to this first mutation, a second mutation can be introduced by adding a stop codon as a result of substitution of one nucleotide downstream in the C open reading frame (FIG. 1B) (Patterson, J. B. et al., *Virology*, 2000, 267(1): 80-89).

According to the convention used for paramyxoviridae, the term "gene" may be used to designate the genome RNA nucleic acid encoding mRNA. In the context of the present invention, it may also refer to the ORF contained in said mRNA.

Said mutation to silence expression of the C protein must preserve the expression of the P gene for its ability to express the P protein.

In a preferred embodiment, the mutated RNA nucleic acid of MV further meets the so-called "rule of six". The "rule of six" is expressed in the fact that the total number of nucleotides present in a nucleic acid encoding the full-length MV(+) strand RNA genome is a multiple of six. In a particular embodiment, nucleic acid constructs comprising same or comprising the mutated MV-deltaC genome or consisting of said mutated MV-deltaC genome, and possibly additional, in particular coding, sequences is a multiple of six. The "rule of six" has been acknowledged in the state of the art as a requirement regarding the total number of nucleotides in the genome of the MV, which enables efficient or optimised replication of the MV genomic RNA as a consequence of interaction with each MV protein subunit encapsidating 6 ribonucleotides on the genome to form the nucleocapsid.

Processes that disclose expression of the C protein that has been knocked out in different MV strains, such as the highly pathogenic IC-B strain (Takeuchi, K. et al., *J. Virol.*, June 2005, 7838-7844) or the Edmonston B vaccine strain (Radecke, F. et al., *Virology*, 1996, 217:418-421; Patterson, J. B. et al., *Virology*, 2000, 267(1):80-89), have been proposed in the prior art by using a reverse genetics system, and may be applied in the context of the present invention.

As defined herein, the expression "infectious measles virus derived from a live-attenuated measles virus strain" designates a measles virus originating from a strain that is avirulent or less virulent than a determined parent strain in the same host, especially in human, while maintaining infectious properties and immunogenicity and possibly adjuvanticity when administered in a host, especially in human, i.e., preserving immunodominant T and B cell response to MV and possibly the adjuvanticity such as the induction of T cell costimulatory proteins or the cytokine IL-12. Pathogenic primary strains strongly disrupt hematopoiesis (Arneborn, P. et al., *Clin Exp Immunol*, 1983, 51:165-172; Kim, E. A. et al., *Radiographics*, 2002, 22 Spec No: S137-149; Okada, H. et al., *Arch Virol*, 2000, 145:905-920), thus resulting on transitory immunosuppression responsible for most deaths due to measles infection in developing countries. In contrast to primary strains, live-attenuated strains do not induce immunosuppression (Okada, H. et al., *Arch Virol*, 2001, 146:859-874).

A live-attenuated MV strain accordingly refers to a strain which has been serially passaged on selected cells and, preferably, adapted to other cells such as primary cells with an IFN α/β response, i.e. CEF cells, to produce seed strains suitable for the preparation of vaccine strains, harboring a stable genome which would not allow reversion to pathogenicity nor integration into host chromosomes, in particular human host chromosomes. In a particular embodiment of the invention, a live-attenuated MV is one which has been selected on primary cells such as CEF cells.

As a particular "live-attenuated strain", an approved strain for a vaccine used for human is a live-attenuated strain suitable for the invention when it meets the criteria defined by the FDA (US Food and Drug Administration) i.e., it meets safety, efficacy, quality and reproducibility criteria, after rigorous reviews of laboratory and clinical data (www.fda.gov/cber/vaccine/vacappr.htm).

In the present invention, a particular live-attenuated MV strain providing MV virus is the Schwarz strain or the Moraten strain, in particular from the Rouvax® vaccine (Aventis). It has been demonstrated that the Schwarz strain has a perfect identity of sequence with the Moraten strain (Parks, C. L. et al., 2001, *J Virol*, 75(2): 910-920; Schwarz, A. J., 1962, *Am J Dis Child*, 103, 386-389). The Schwarz/Moraten strains are currently widely-used since they induce long-term cell and humoral immune responses and present an important genetic stability since no reversion to a pathogenic form has ever been observed (Hilleman, M., 2002, *Vaccine*, 20:651-665).

More preferably, the genetically modified infectious MV of the invention is produced using a cDNA of MV Schwarz strain cloned into the plasmid pTM-MVSchw, deposited by Institut Pasteur at the CNCM (Paris, France) under number I-2889 on Jun. 12, 2002, the sequence of which is described by Combredet (Combredet, C. et al., 2003, *J Virol*, 77(21): 11546-11554), and also disclosed in WO2004/000876 and in Example 1 of the present invention. The plasmid pTM-MVSchw has been obtained from a Bluescript plasmid, comprises the polynucleotide coding for the full-length MV (+) RNA strand of the Schwarz strain placed under the control of the promoter of the T7 RNA polymerase, and has 18967 nucleotides. cDNAs from other MV strains may be similarly obtained starting from the nucleic acid purified from viral particles of live-attenuated MV. In order to prepare a suitable cDNA encoding the MV-deltaC genome, plasmid pTM-MVSchw has been modified by substitution of the second "ATG" start codon in the P gene to give plasmid pTM-MVSchw-deltaC-ATU1 (eGFP) (SEQ ID NO: 1). In particular, the "ATG" codon has been replaced with the "ACG" codon by mutation of the T nucleotide to the C nucleotide.

In a particular embodiment, the pTM-MVSchw-deltaC-ATU1 (eGFP) plasmid of SEQ ID NO:1 is further mutated by substitution at position 2803 of the G nucleotide by an A nucleotide to provide a stop codon. This variant of pTM-MVSchw-deltaC-ATU1 (eGFP) has the nucleotide sequence of SEQ ID NO: 2.

In a preferred embodiment of the invention, the genetically modified infectious MV-deltaC is obtained by rescue. Rescue of unmodified MV of the Schwarz MV strain has been described extensively in WO2004/000876 and the same process can be applied to the preparation of the genetically modified infectious MV-deltaC.

In a particular embodiment of the invention, the genetically modified infectious MV-deltaC expresses GM-CSF (Granulocyte Macrophage-Colony Stimulating Factor) (Guse, K. et al., 2011, *Oncolytic vaccinia virus for the treatment of cancer*, Vol. 11, No. 5, Pages 595-608), and accordingly is MV-deltaC-GM-CSF.

As defined herein, the expression "for use in the treatment" means that a genetically modified infectious MV-deltaC can be used in a process of administration to an individual to completely eradicate a malignant tumour or a cancer condition diagnosed in an individual, especially in a human, or to reduce the size of the tumour, or to alleviate symptoms of such a malignant tumour or a cancer condition. In a particular embodiment, virotherapy involving the MV-deltaC according to the invention may be accompanied by other therapies, in particular chemotherapy. Thus, the virotherapy involving MV-deltaC may be used in a combination or an add-on therapeutic regime.

As defined herein, the expression "aggressive malignant tumour or aggressive cancer" refers to a malignant tumour or a cancer that is refractory to currently known conventional treatment modalities, such as chemotherapy, radiotherapy and/or surgery, and as a consequence develops despite such a conventional treatment.

As defined herein, the expression "by activating plasmacytoid dendritic cells (pDCs)" refers to MV or MV-deltaC infected tumour cells that hire pDCs in the antitumour immune response by activating their ability to produce high quantities of IFN-α and/or to cross-present TAA from infected tumour cells to tumour-specific CD8+ T lymphocytes.

As defined herein, the term "plasmacytoid dendritic cells (pDCs)" encompasses antigen-presenting cells that produce large amounts of alpha/beta interferons (IFN-α/β) in response to viral and bacterial stimuli, and, in the present invention, are recognised to be capable of phagocytosing tumour infected cells.

In a particular embodiment, said MV-deltaC can be used in the treatment of malignant mesothelioma, in particular malignant pleural mesothelioma.

In another particular embodiment, the present invention relates to a genetically modified infectious measles virus derived from a live-attenuated measles virus strain, in which the gene encoding the viral accessory C protein has been knocked out (MV-deltaC) for use in the treatment of melanoma or lung adenocarcinoma, when administered to an individual diagnosed with such a condition.

A particular embodiment of the invention provides a genetically modified infectious MV-deltaC that can be used in the treatment of malignant tumour or cancer cells that are resistant to unmodified MV, when administered to an individual diagnosed with a malignant tumour or a cancer condition.

The expression "unmodified MV" refers to an infectious live-attenuated strain of MV that has not been genetically modified, such as a virus of the Schwarz or Moraten strain.

As defined herein, the expression "malignant tumour or cancer cells that are resistant to unmodified MV" refers to malignant tumour or cancer cells that are known to resist to cell death induction, despite an efficient infection with unmodified MV, or that are known to undergo a weaker response to cell death induction with unmodified MV than with MV-deltaC.

It has been shown by the inventors that administration of MV-deltaC to various malignant tumour or cancer cells provides or elicits a response which is improved with respect to the response obtained when unmodified MV is administered and in particular elicits improved apoptotic activity at lower concentration levels, with a shorter response time and improved immunogenic properties (Kroemer, G. et al., *Annu. Rev. Immunol.*, 2012, 31:51-72).

According to a particular embodiment of the invention, said genetically modified infectious MV-deltaC displays an apoptotic activity in MV-deltaC infected malignant tumour or cancer cells.

As defined herein, the expression "apoptotic activity" refers to the ability to induce or elicit apoptosis in cells which can be demonstrated by in vitro apoptosis in malignant tumour or cancer cells, in particular in malignant mesothelioma, melanoma and lung adenocarcinoma cells of the examples.

The activities displayed by a MV-deltaC virus of the invention may be characterised by the production of molecules of the immune response or in the cellular stress or in the cell death. These molecules encompass the HMGB-1 (High-Mobility Group Box-1), the calreticulin and Heat Shock Protein (Hsp70), which were described as danger signals involved in the activation of immune response (Zitvogel, L et al. *Cell*, 2012, 140:798-804).

Caspase-3 is known to be involved in late events of the apoptosis program (Duprez, L. et al., *Microbes Infect*, 2009, 11(13): 1050-1062).

According to a particular embodiment of the invention, said genetically modified infectious MV-deltaC induces the activation of caspase-3 in MV-deltaC infected malignant tumour or cancer cells.

The presence of Hsp70 protein on the outer layer of the plasma membrane of infected cells is involved in the immune response, in particular in the recognition by antigen-presenting cells and innate cellular immune effectors (Oglesbee et al., *Viral Immunol*, 2002, 15(3): 399-416).

According to a particular embodiment of the invention, said genetically modified infectious MV-deltaC induces the exposure of the Hsp70 protein to the outer layer of the plasma membrane in MV-deltaC infected malignant tumour or cancer cells.

Calreticulin is an essential protein of the endoplasmic reticulum, which can be relocalised to the outer layer of the plasma membrane during cellular stress (Heal et al., *Biochem J*, 1998, 329(2), 389-394). In particular, this exposure to the cell surface allows for phagocytosis of apoptotic cells by antigen-presenting cells (Ogden et al., *J Exp Med*, 2001, 194(6):781-795). Recently, some research hypothesised that calreticulin exposure at the cell surface dictates the immunogenicity of their death (Obeid et al., *Nat Med*, 2007, 13(1): 54-61).

According to a particular embodiment of the invention, said genetically modified infectious MV-deltaC induces the translocation of calreticulin to the MV-deltaC infected malignant tumour or cancer cell surface.

The HMGB-1 (High-Mobility Group Box-1) protein released in the environment during the immunogenic cell death acts on the maturing of dendritic cells by binding to different receptors, such as TLR4 (Apetoh et al., *Nat Med*, 2007, 13(9): 1050-1059) and TLR9 (Tian et al., *Nat Immunol*, 2007, 8(5): 487-496).

According to a particular embodiment of the invention, said genetically modified infectious MV-deltaC induces the liberation of HMGB-1 in the extracellular medium of MV-deltaC infected malignant tumour or cancer cells.

The inventors have compared cell death induction in human cancer cell lines (A549 human lung adenocarcinoma cells and Hela cervical cancer cells) and in non-cancer cells (HEK 293 human embryonic kidney cells and Vero African Green monkey kidney cells). They demonstrated that MV-deltaC induced a much higher and earlier cell death than unmodified MV on both A549 and Hela human cancer cells, even at low MOI (FIG. 23A). The inventors have also observed that cell death induction on Vero cells was similar for both unmodified MV and MV-deltaC, while no cell death was observed on HEK 293 cells after 68 hours of infection (FIG. 23B). Thus the inventors proved that MV-deltaC was specific to human cancer cells: in fact, MV-deltaC showed a higher apoptotic activity than unmodified MV when it was brought into contact with human cancer cells but showed a similar apoptotic activity to unmodified MV when it was brought into contact with lab cell lines, i.e. Vero cells.

The present invention also relates to a method for preparing vaccinal plasmacytoid dendritic cells (pDCs) intended for treating a malignant tumour or a cancer in an individual diagnosed with such a malignant tumour or a cancer condition, comprising the following steps:

in vitro infection of malignant tumour or cancer cells previously collected from the individual with an infectious measles virus derived from a live-attenuated measles virus strain to yield a cell lysate;

contacting pDCs with the cell lysate to yield vaccinal pDCs;

recovering loaded pDCs.

The present invention also relates to a method for preparing vaccinal plasmacytoid dendritic cells (pDCs) intended for treating a malignant tumour or a cancer in an individual diagnosed with such a malignant tumour or a cancer condition, comprising the following steps:

in vitro infection of malignant tumour or cancer cells previously collected from the individual with a genetically modified infectious measles virus derived from a live-attenuated measles virus strain, in which the gene encoding the viral accessory C protein has been knocked out (MV-deltaC) to yield a cell lysate;

contacting the pDCs with the cell lysate to yield vaccinal pDCs;

recovering the loaded pDCs.

In the present invention, said malignant tumour or cancer of the above-defined method is an aggressive malignant tumour or an aggressive cancer, in particular malignant mesothelioma, melanoma or lung adenocarcinoma.

In the present invention, said live-attenuated measles virus strain of the above-defined method is the Schwarz strain or the Moraten strain.

Where MV-deltaC is administered to an individual, it can be administered through the intrapleural cavity or by the intranasal, intramuscular, intravenous or subcutaneous routes. Where MV-deltaC is administered through the intrapleural cavity, it is preferably administered in close proximity or directly into the malignant tumour or cancer cells to be treated.

The therapeutically effective quantity of MV-deltaC to be administered is preferably in the range of from $10^3$ to $10^9$ 50% tissue culture infective doses (TCID50). TCID50 determination is well known to a person skilled in the art and is notably described by Kärber (Kärber, *Arch. Exp. Path. Pharmak,* 1931, 162:840-483).

The step of taking the malignant tumour or cancer cells from the individual to enable ex vivo preparation of the vaccinal pDCs is preferably not included in the method of preparation of vaccinal pDCs. This step can be performed according to any technique known to a person skilled in the art for taking or sampling cells, such as biopsies and effusions (i.e. pleural effusions). After being taken, the malignant tumour or cancer cells can be maintained in culture according to classical techniques, or frozen (i.e. at −80° C.) for conservation, for instance. Where the malignant tumour or cancer cells do not originate from the individual to be treated by the vaccinal pDCs, they can notably derive from allogenic malignant mesothelioma, melanoma and lung adenocarcinoma cell lines.

In the above-defined in vitro method of preparation, infection of the malignant tumour or cancer cells with MV-deltaC can be performed by directly contacting cells and virus, for instance at a Mutliplicity Of Infection (MOI) of 1, with an incubation of 2 hours at 37° C. After infection, death of the infected cells proceeds spontaneously due to virus action. A syncitia is usually first formed, followed by lysis of the cells, thereby providing a cell lysate suitable for vaccine preparation. This phenomenon can be evidenced by direct microscopic observation of infected cells.

As defined herein, the term "cell lysate" encompasses whole (or total) cell lysate obtained as disclosed herein, or fractions of the cell lysate, such as membrane fractions (i. e. cytoplasmic inclusion bodies or apobodies).

pDCs can be obtained by numerous ways well known to a person skilled in the art. In a particular embodiment of the invention, the pDCs preferably originate from the individual to be treated. It is presently preferred that the pDCs are derived from leukapheresis. Obtaining pDCs is particularly well known to a person skilled in the art. Preferably, pDCs can be obtained following the general methodology described by Coulais (Coulais, D et al., *Cytotherapy,* 2012, 14(7): 887-896). Where the pDCs originate from the individual to be treated, the pDCs can be obtained from leukapheresis of said individual.

As will be apparent to a person skilled in the art, contacting of the pDCs and of the cell lysate should be maintained for a time sufficient to enable an effective loading of the pDCs by antigens present in the cell lysate. Once loaded (or pulsed), vaccinal pDCs according to the invention are obtained. Loading can proceed by following the general methodology described by Gauvrit (Gauvrit, A et al., *Cancer Res,* 2008, 68(12), 4882-4892). An exemplary contact period between the pDCs and the cell lysate sufficient to enable efficient loading of the pDCs is of about 24 hours. The activated state for pDCs is usually reached after the pDCs have been loaded. The activated state (or mature state) of pDCs can be evidenced by numerous markers well known to a person skilled in the art, such as membrane or cytokine markers. Such markers of activated dendritic cells have been notably listed by Barchet (Barchet, W et al., *Seminars in Immunology,* 2005, 17(4):253-261) and Marafioti (Marafioti, T et al., *Blood,* 2008, 111(7):3778-3792).

Thus, vaccinal pDCs, which can be obtained according to the method of preparation of the invention are particularly advantageous since they are potent stimulators of anti-cancer CD8 T cells. Equally advantageous, the method of preparation according to the invention allows the preparation of vaccinal pDCs in an activated state.

The present invention relates in particular to vaccinal dendritic cells which can be obtained by the above-defined method of preparation. According to a particular embodiment of the invention, said vaccinal pDCs can be used in the treatment of an aggressive malignant tumour or of an aggressive cancer, when administered to an individual diagnosed with such a malignant tumour or a cancer condition.

More particularly, it can be used in the treatment of malignant mesothelioma, melanoma, or lung adenocarcinoma, when administered to an individual diagnosed with such a condition. The embodiments disclosed herein in relation to the application of the MV-deltaC are similarly relevant for the use of pDCs as described herein.

The inventors addressed, in vitro, the effect of tumour cell infection by MV Schwarz on the activation status of human pDCs and their ability to cross-present a tumour antigen to a specific CD8+ T cell clone. The inventors showed that, despite CD46 expression, pDCs were not sensitive to MV infection. However, pDCs were able to respond in vitro to MV by producing IFN-α, with a greater sensitivity when IL-3 was added to the culture. The inventors also demonstrated that MV-infected tumour cells triggered pDC activation, notably IFN-α production, whereas UV-irradiated tumour cells did not. pDC activation was probably caused by the single-stranded RNA of MV, which triggered TLR7 in the pDC endocytic compartment following phagocytosis of MV-infected tumour cells. Interestingly, the inventors showed as an illustration, for the first time, that human pDCs co-cultured with MV-infected tumour cells were able to cross-present the NYESO-1 tumour antigen to a specific CD8+ T cell clone. These results suggest that, in addition to a direct tumour lysis effect, MV-based antitumour virotherapy may trigger an antitumour immune response by activating pDCs. Similar results are expected using MV-deltaC since the tumour cell infection by the mutated virus happens to be similar. A higher response is even expected since MV-deltaC leads to higher expression of danger signals (calreticulin and Hsp70) after infection of the tumour cells and the infected cells also expressed the single-stranded RNA of MV-deltaC.

The present invention is also directed to a pharmaceutical composition comprising a genetically modified infectious MV-deltaC or vaccinal pDCs which can be obtained by the above-defined method, as active ingredient, in association with a pharmaceutically acceptable vehicle, for use in the treatment of an aggressive malignant tumour or of an aggressive cancer by activating pDCs, when administered to an individual diagnosed with such a malignant tumour or a cancer condition.

As defined herein, pharmaceutically acceptable vehicles encompass any substance that enables the formulation of MV-deltaC within a composition. A vehicle is any substance or combination of substances physiologically acceptable i.e., appropriate for its use in a composition in contact with a host, especially a human, and thus non-toxic. Examples of such vehicles are phosphate buffered saline solutions, distilled water, emulsions such as oil/water emulsions, various types of wetting agents sterile solutions and the like.

The present invention also concerns a pharmaceutical composition or an assembly of active ingredients comprising a genetically modified infectious MV-deltaC or vaccinal pDCs which can be obtained by the above-defined method, and further comprising a chemotherapeutic agent and a pharmaceutically acceptable vehicle for use in the treatment of an aggressive malignant tumour or of an aggressive cancer, when administered to an individual diagnosed with such a malignant tumour or a cancer condition.

As defined herein, a chemotherapeutic agent is a molecule that can be used in the treatment of a malignant tumour or a cancer. The nature of the chemotherapeutic agent will depend on the type of malignant tumour or cancer. Examples of chemotherapeutic agents are well known to a person skilled in the art.

The present invention is also directed to an assembly of active ingredients comprising (i) a live-attenuated MV or a genetically modified infectious MV-deltaC and (ii) vaccinal pDCs which can be obtained by the above-defined method, for use for simultaneous or separate administration in the treatment of an aggressive malignant tumour or of an aggressive cancer, when administered to an individual diagnosed with such a malignant tumour or a cancer condition.

BRIEF DESCRIPTION OF THE DRAWINGS

FIG. 3A-3D: Replication kinetics of MV, MV-P$_{G954}$, MV-deltaV and MV-deltaC. Vero (A), HeLa (B), Jurkat (C) and U937 (D) cells were infected with the different viruses at a MOI of 1. Cell-associated viral titers were determined as TCID$_{50}$ values.

FIG. 4: Cytopathic effects of MV and MV-deltaC on Vero and HeLa cells. Upper panel: cytopathic effects induced on Vero cells 24 hours after infection with MV or MV-deltaC (MOI of 0.1). Lower panel: immunofluorescence of HeLa cells 24 hours after infection with MV or MV-deltaC. Cells were fixed and stained with a monoclonal anti-hemmaglutinin (H) of MV.

B) Virus infected (MV or MV-deltaC) and uninfected tumour cells were analysed by flow cytometry after staining with an anti-active caspase-3 antibody (BD Biosciences) at 72 hours after infection. The percentages indicate the proportion of "activated Caspase-3-positive" cells after MV-deltaC infection.

Figure 8:
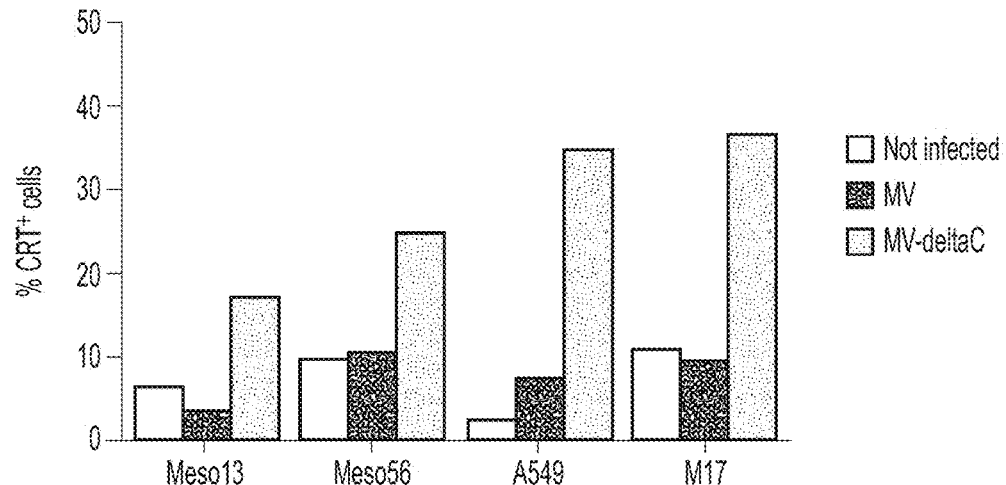

FIG. 8: Exposure of the Hsp70 protein to the cell surface. The membrane Hsp70 protein expression was determined at 48 hours after infection for Meso13 and Meso56 epithelioid mesothelioma cells or at 72 hours after infection for A549 lung adenocarcinoma and M17 melanoma cells, by extracellular staining and flow cytometry. Data represent the percentages of Hsp70 cells.

Figure 9:
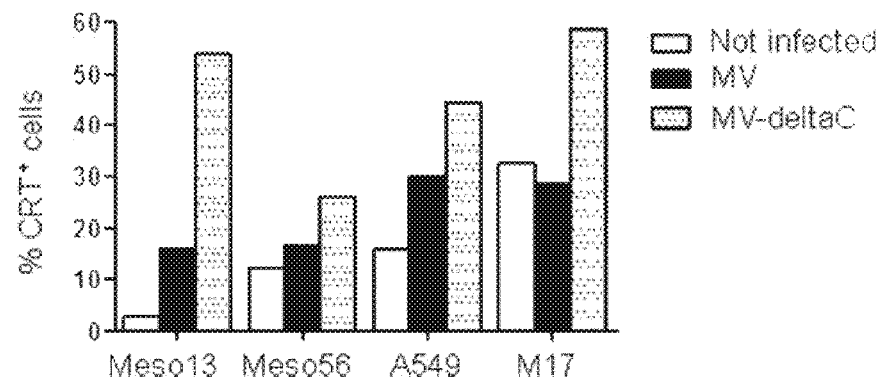

FIG. 9: Membrane translocation of calreticulin after MV-deltaC infection. Uninfected and infected (MV or MV-deltaC, MOI=1) tumour cells were stained with an anti-calreticulin antibody and a Cy5 conjugated anti-mouse secondary antibody at 48 hours after infection for Meso13 and Meso56 epithelioid mesothelioma cells or at 72 hours after infection for A549 lung adenocarcinoma cells and M17 melanoma cells. Cells were then analysed by flow cytometry. Data represent the percentages of calreticulin cells.

Figure 10:
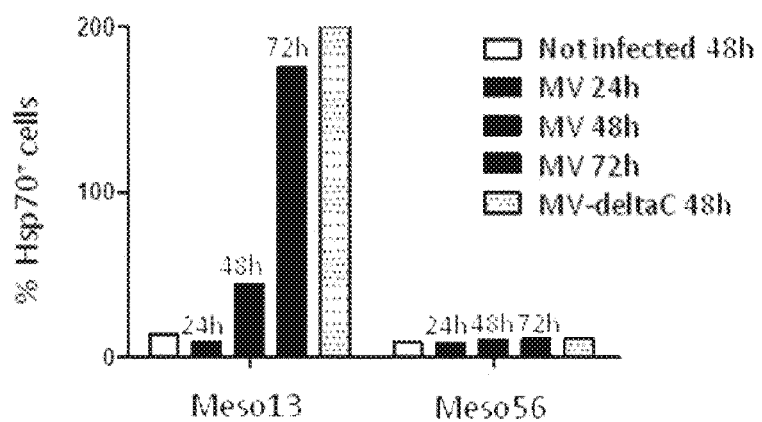

FIG. 10: Release of HMGB-1 in the extra-cellular environment. Supernatants of uninfected or infected (MV or MV-deltaC, MOI=1) tumour cells were collected at 24, 48 or 72 hours after infection and stored at −20° C. The quantity of HMGB-1 in these supernatants was then determined by ELISA.

Figure 1A:
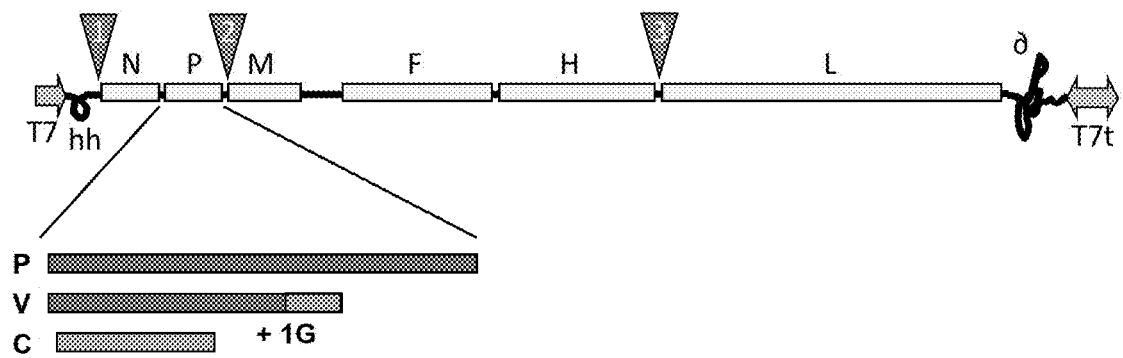
FIGS. 1A and 1B: MV and MV-deltaC. (A) Schematic diagram of MV genome and gene order showing that the P gene encodes for the P, V and C proteins (the P, V and C ORFs are shown). B) Portion of the nucleotide sequence of plasmids pTM-MVSchw (SEQ ID NO: 3) and pTM-MVSchw-deltaC-ATU1 (eGFP), wherein the T nucleotide of native MVSchw genome cDNA at position 2788 has been replaced by a C nucleotide (SEQ ID NO: 4); in addition to this first mutation, a second mutation can be introduced by adding a stop codon downstream in the C open reading frame, i.e. the "TAG" stop codon, which is obtained by replacing the G nucleotide of native MVSchw genome cDNA in position 2803 by an A nucleotide (SEQ ID NO: 5) (the introduced nucleotide mutations are underlined).

FIG. 11A to 11E: MV receptor expression, MV infection sensitivity and survival of tumour cells and pDCs. (A) Expression of CD46 and CD150/SLAM on the surface of tumour cell lines (M18, Meso13 and A549) and pDCs (mAb staining: grey histogram; Isotype control: white histogram; the values on histograms are the R-MFI, relative mean fluorescence intensity, defined as the mAb staining MFI divided by Isotype control MFI). (B) Infection of tumour cell lines (M18, Meso13 and A549) and pDCs by MV-eGFP (MOI=1). (C) Infection of pDCs by MV-eGFP (MOI=1), in the presence or absence of IL-3. (D) Infection of pDCs by MV-eGFP with increasing MOI, in the presence or absence of IL-3. (E) Survival of tumour cell lines following MV infection or UV irradiation. Three days after infection or UV irradiation, cells were incubated with TO-PRO®3 which stains dead cells. Fluorescence was analysed by flow cytometry. Results in FIGS. 1A, 1C and 1E are representative of three independent experiments. Results in FIGS. 1B and 1E reflect the mean of three independent experiments. Error bars represent the standard deviation.

Figure 12:
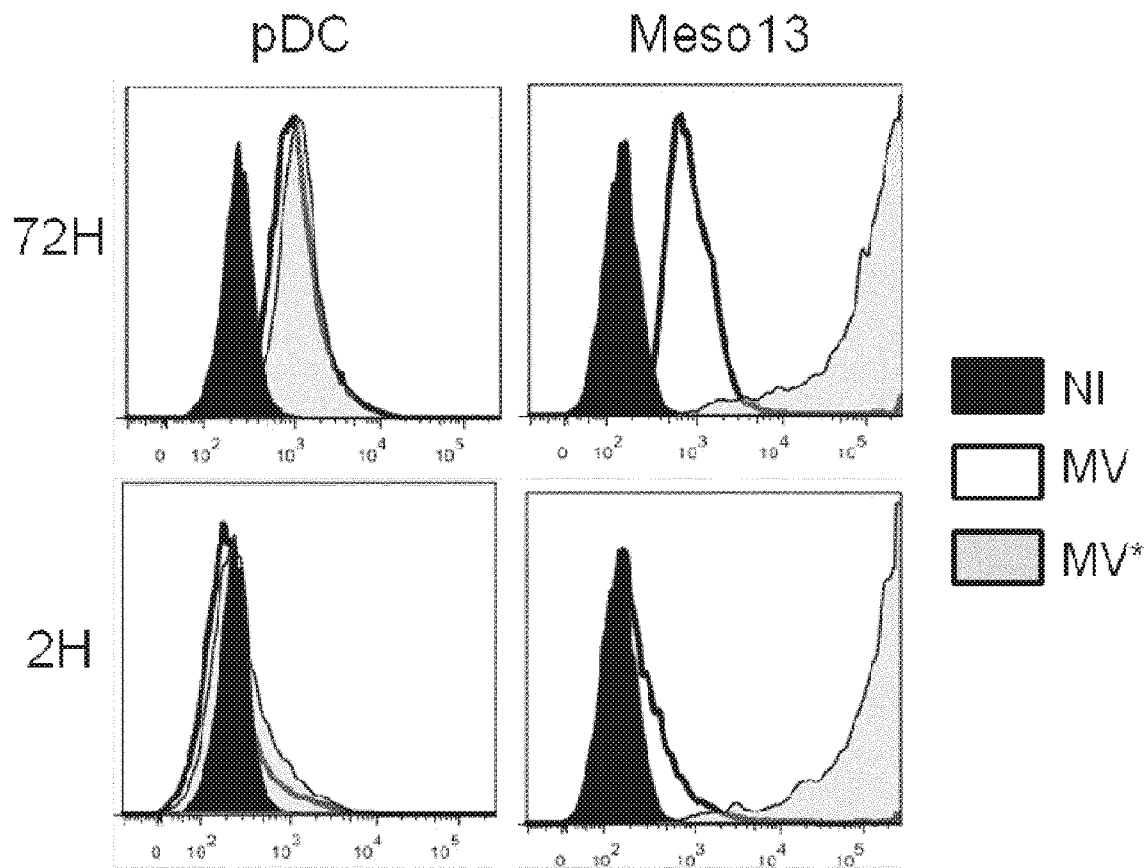

FIG. 12: Infection of pDCs by MV-eGFP or UV-irradiated MV-eGFP. pDCs in the presence of IL-3 or Meso13 cells were cultured alone (NI) or with MV-eGFP (MV) or UV-irradiated (312 nm-100 kJ/m$^2$) MV-eGFP (MV*) at MOI=50 during 72 hours (upper panel) or during 2 hours and then cultured during 70 hours (lower panel). Fluorescence was analysed by flow cytometry.

Figure 13B:
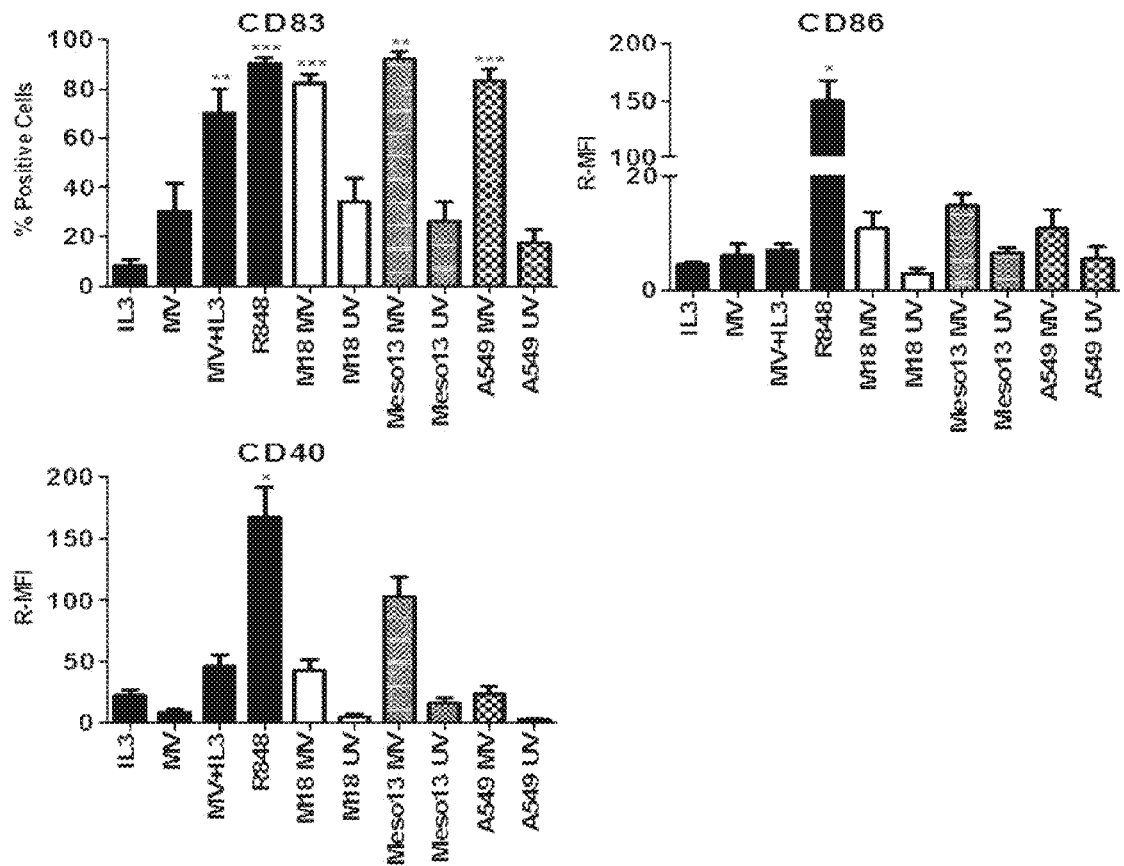

FIGS. 13A and 13B: MV-infected tumour cells induce pDC maturation. pDCs were cultured for 18 hours with either IL-3, MV (MOI=1), MV and IL-3, R848, UV-irradiated- or MV-infected tumour cells. (A) Expression of CD83, CD86 and CD40 by pDCs was measured by flow cytometry with a gate on CD123$^+$/BDCA-4$^+$ cells. (B) Histograms were obtained from three independent experiments. A nonparametric Mann Whitney comparison test was used to determine the P value, which was obtained by comparison of the sample result with the IL-3 pDC result (*p<0.05, p<0.01, *p<0.001).

FIG. 14A to 14D: Activation of pDCs in response to MV-infected tumour cells is independent of MV replication in pDCs and infection by CD46. (A) pDCs were cultured with IL-3 alone, R848, IL-3/MV-eGFP (MV), IL-3/MV-eGFP with 10 mg/mL of anti-CD46 or IL-3/UV-irradiated MV-eGFP (MV*) at MOI=1 during 18 hours. Expression of CD83, CD80 and CD86 by pDCs was determined by flow cytometry. (B) pDCs were cultured with IL-3, UV-irradiated M18, MV-infected M18 (M18MV) in presence or absence of 10 mg/mL of anti-CD46 (Hycult biotech), or MV-infected M18 irradiated by UV before exposition to pDCs (M18MV*). Expression of CD83, CD80 and CD86 by pDCs (gate on BDCA-4+/HLA-DR+ cells) was determined by flow cytometry. (C) IFN-α production by pDCs measured by ELISA. (D) MV-eGFP infection inhibition of M18 by 10 mg/mL of anti-CD46 monoclonal antibody after 72 hours of culture.

Figure 15A:
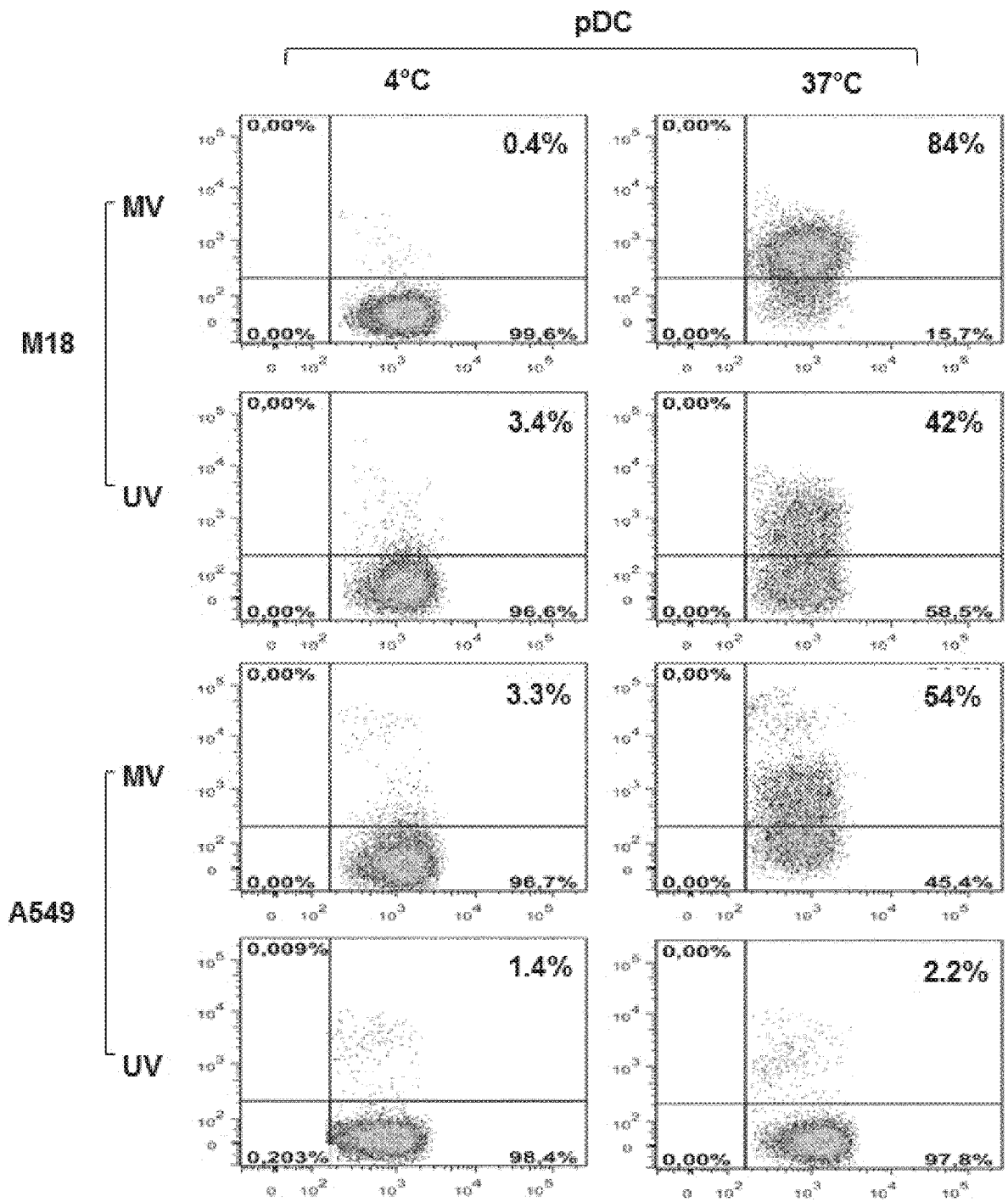
Figure 15B:
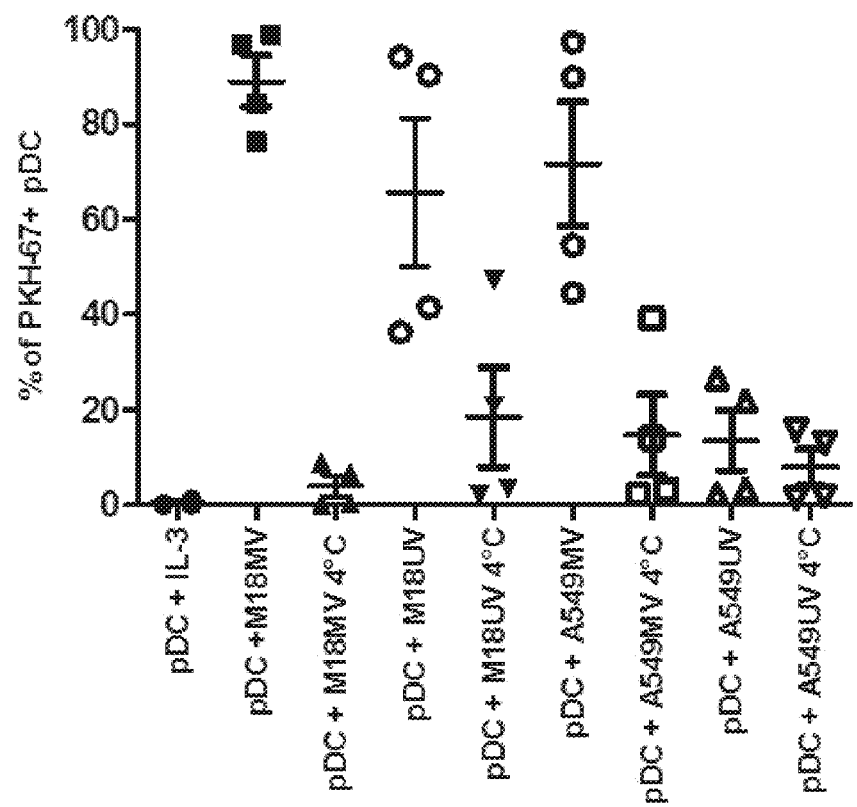
Figure 15C:
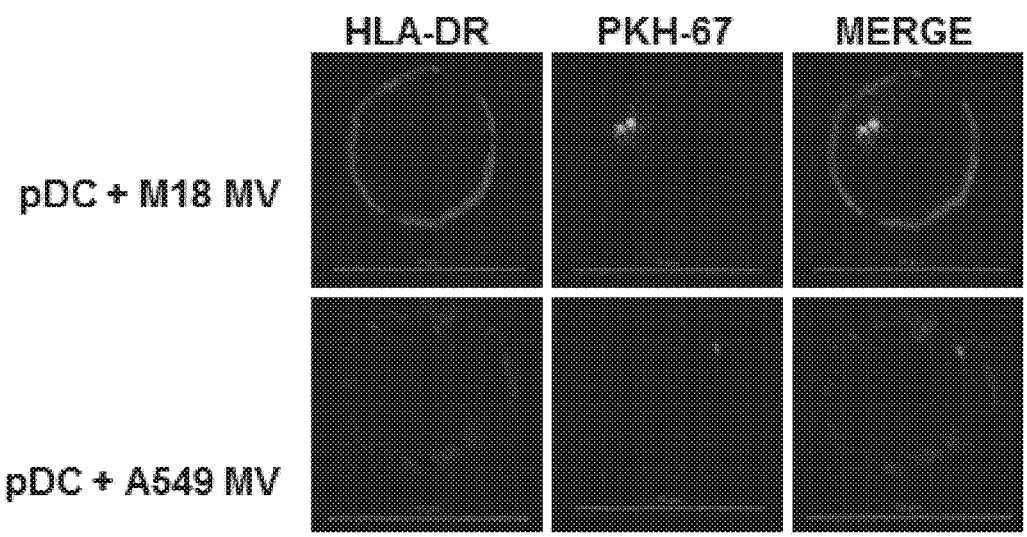

FIG. 15A to 15C: Phagocytosis of MV-infected or UV-irradiated tumour cells by pDCs. (A) MV-infected and UV-irradiated tumour cells were stained with PKH-67 and co-cultured with pDCs for 18 hours at 4° C. or 37° C. (1 DC:1 tumour cell). Cells were stained with HLA-DR-specific mAb. Fluorescence was analysed by flow cytometry. This experiment is representative of four experiments. (B) Scatter plot representation of the four phagocytosis experiments. Error bars represent the standard deviation. (C) MV-infected tumour cells were stained with PKH-67 (green) and co-cultured with pDCs for 18 hours. Cells were stained with HLA-DR-specific mAb (red). Fluorescence was analysed by confocal microscopy.

Figure 16A:
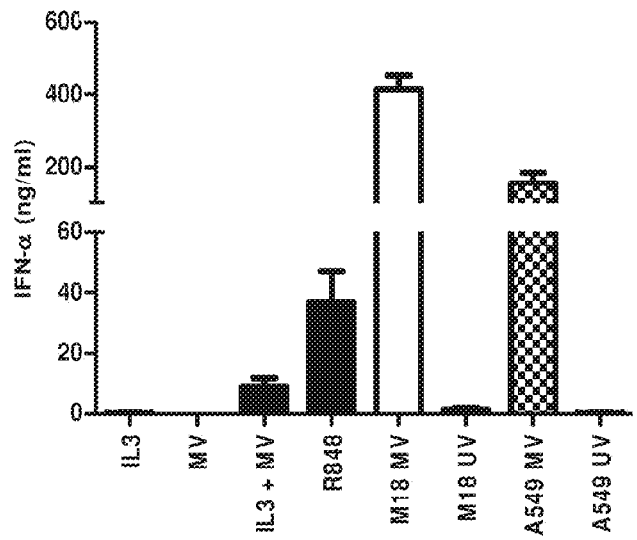
Figure 16B:
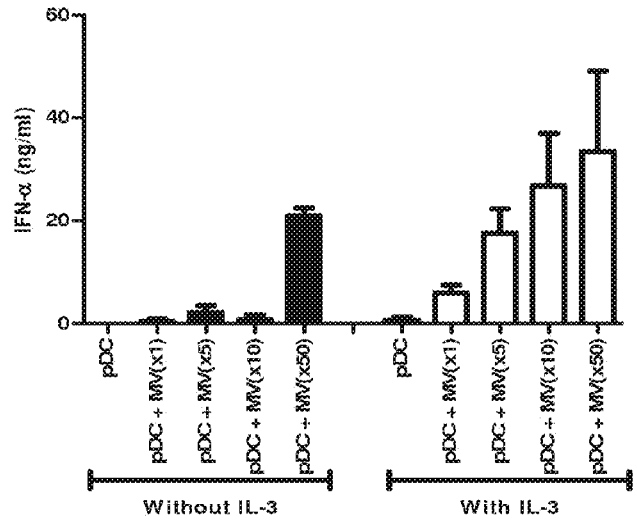
Figure 16C:
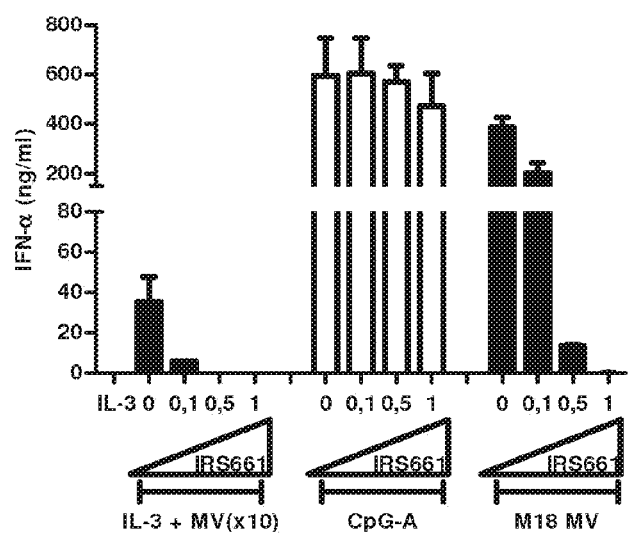

FIG. 16A to 16C: Production of IFN-α by pDCs in response to MV is TLR7 dependent. (A) pDCs were cultured for 18 hours with IL-3, MV (MOI=1), MV and IL-3, R848, UV-irradiated- or MV-infected M18 or A549 tumour cells. IFN-α production was measured by ELISA in the culture supernatants. (B) pDCs were cultured for 18 hours with or without IL-3 and increasing quantities of MV. IFN-α production was measured by ELISA in the culture supernatants. (C) pDCs were cultured for 18 hours with IL-3 and MV (MOI=10), CpG-A or MV-infected M18, in the absence or presence of different concentrations of IRS661 (TLR7 inhibitor). IFN-α production was measured by ELISA in the culture supernatants. Results were obtained from three independent experiments.

FIG. 17A to 17D: Cross-presentation of NYESO-1 by HLA-A*0201+pDC after co-culture with NYESO-1+/HLA-A*0201-M18 tumour cells infected with MV. (A) Expression of NYESO-1 by M18 and A549 tumour cell lines determined by real-time PCR (n=3). (B) pDCs were cultured for 18 hours with IL-3, R848, or UV-irradiated- or MV-infected M18 tumour cells. Some pDCs cultured with R848 were pulsed with NYESO-1(157-165) peptide for 1 hour and washed. pDCs were then co-cultured for 6 hours with the M117.167 CD8+ T cell clone specific for HLA-A*0201/NYESO-1(157-165) (defined as LT) in the presence of brefeldin A. Production of IFN-γ by the M117.167 T cell clone was analysed by flow cytometry after staining with CD8 and IFN-γ-specific mAb. (C) pDCs were cultured for 18 hours with R848, or UV-irradiated- or MV-infected M18 (NYESO-1+/HLA-A*0201$^-$) or A549 (NYESO-1$^-$/HLA-A*0201$^-$) tumour cells. Some pDCs cultured with R848 were pulsed with NYESO-1(157-165) peptide for 1 hour and washed. pDCs were then co-cultured for 6 hours with the M117.167 CD8+ T cell clone specific for HLA-A*0201/NYESO-1(157-165) in the presence of brefeldin A. The production of IFN-γ by the M117.167 T cell clone was analysed by flow cytometry after staining with CD8- and IFN-γ-specific mAb. (D) Scatter plot representation of cross-presentation experiments. "n" represents the number of experiments performed. "n" is different from one condition to another, since the inventors were not able to perform all controls in each experiment due to the limited quantity of available pDCs.

Figure 18:
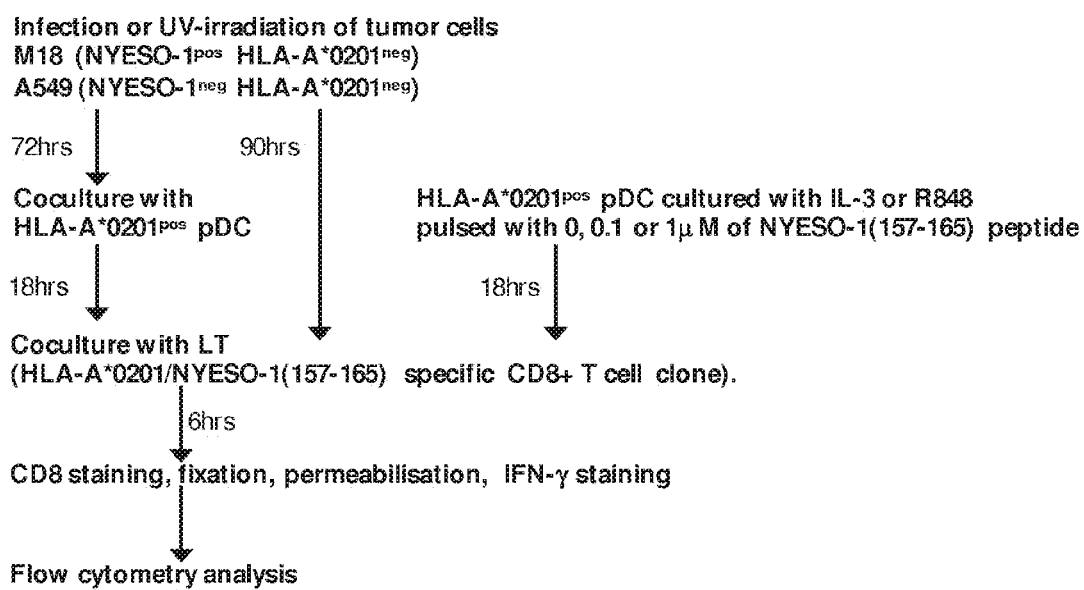

FIG. 18: Schematic of the culture conditions used in the cross-presentation experiments.

Figure 19A:
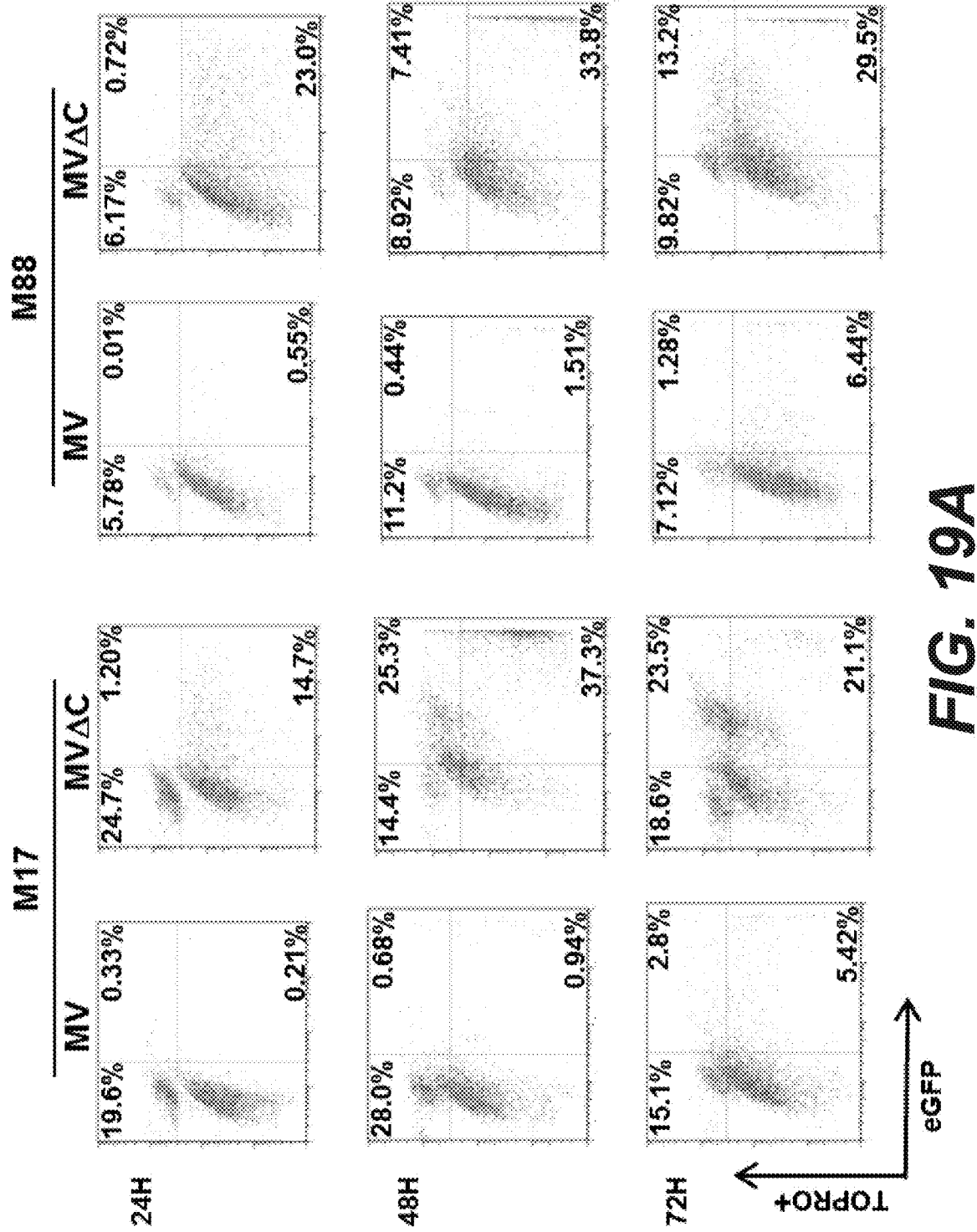
Figure 19B:
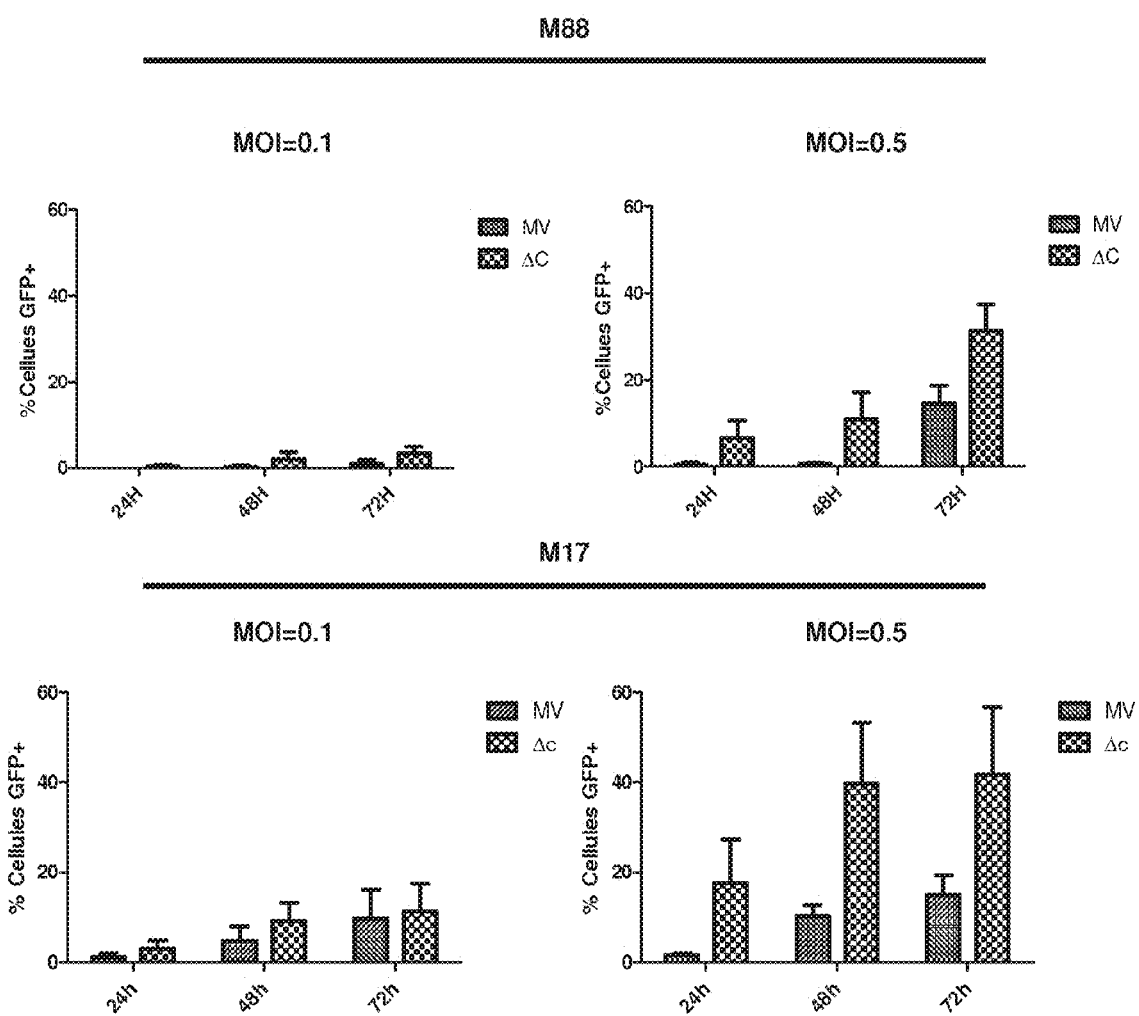

FIGS. 19A and 19B: (A) and (B) Infection and cell death of melanoma cells by unmodified MV or MV-deltaC. Sample analysis by flow cytometry for infection level and cell death induced at 24 h, 48 h and 72 h after infection with unmodified MV or MV-deltaC at an MOI of 1. The MV-deltaC vaccine strain efficiently infected tumour cells that were resistant to infection with the unmodified MV vaccine strain. The melanoma tumour cells were infected with unmodified MV-eGFP or MV-deltaC eGFP at different MOI for 2 hours.

Figure 20:
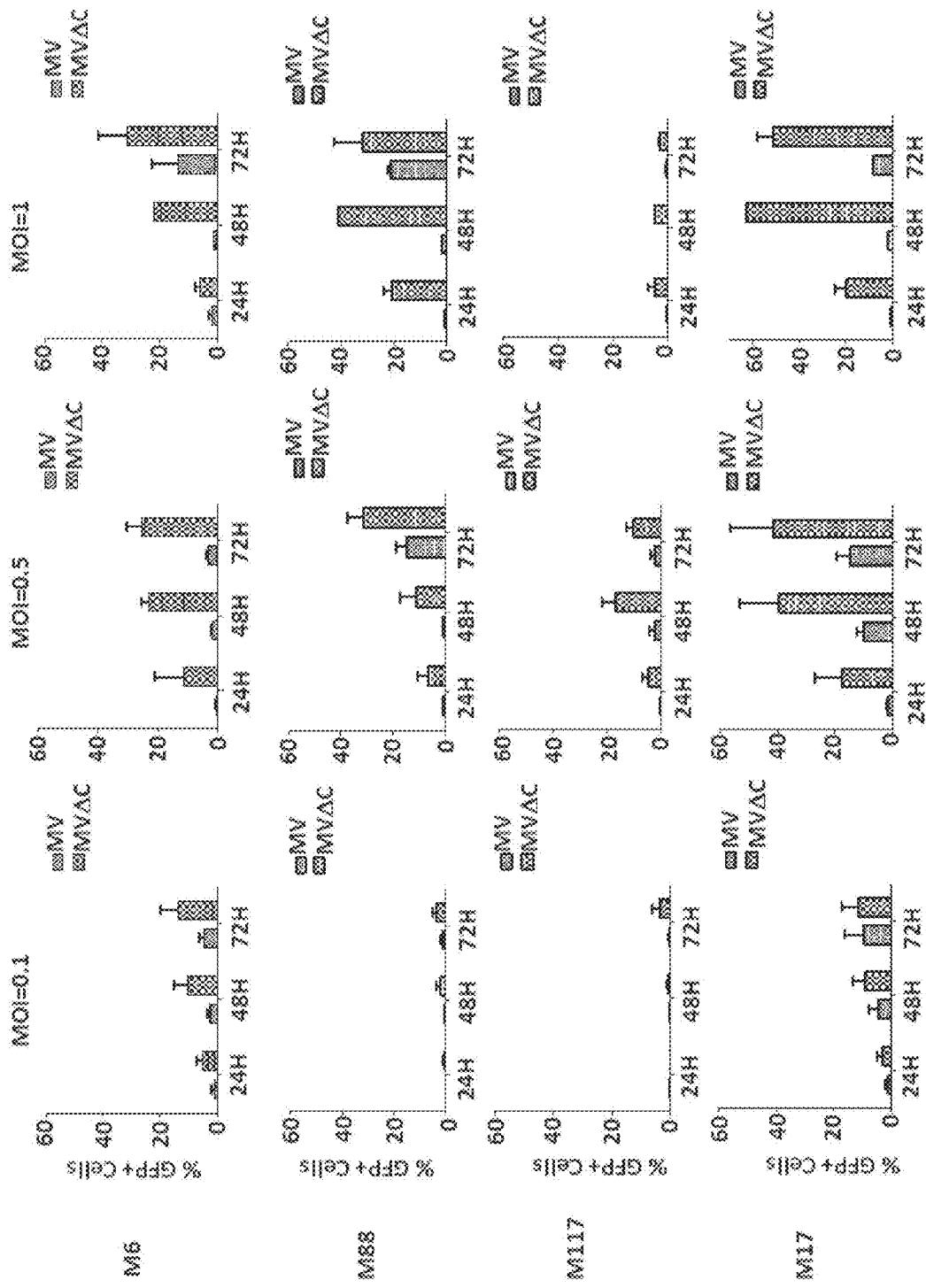

FIG. 20: Cell death of melanoma cells by unmodified MV or MV-deltaC. The melanoma tumour cells were infected with unmodified MV-eGFP or MV-deltaC eGFP at different MOI for 2 hours. The rate of cell death induced (% of Topro+ cells in uninfected cells-% of Topro+ cells in infected cells) of each cell line was determined by flow cytometry at 24 h, 48 h and 72 h post infection.

Figure 21A:
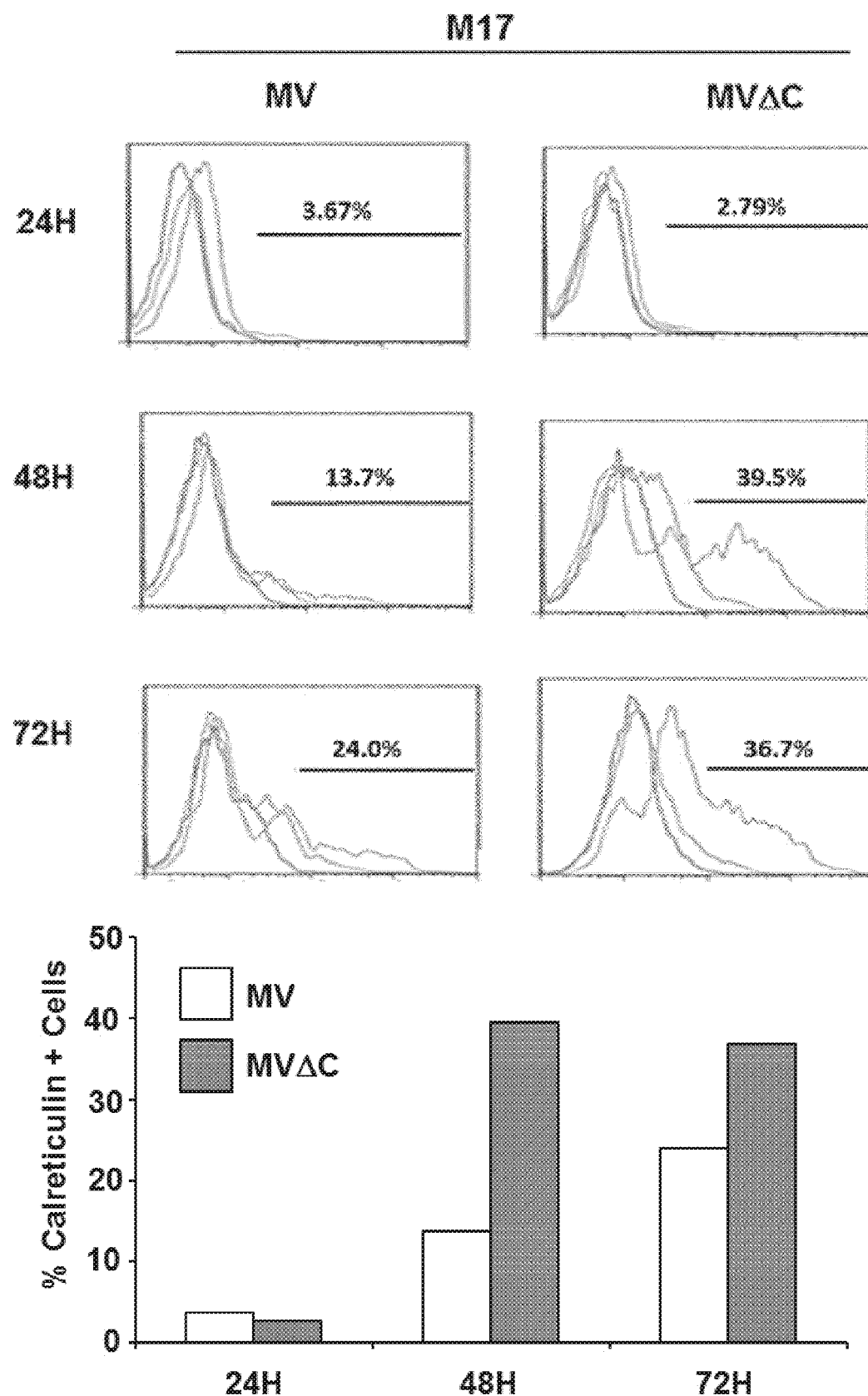
Figure 21B:
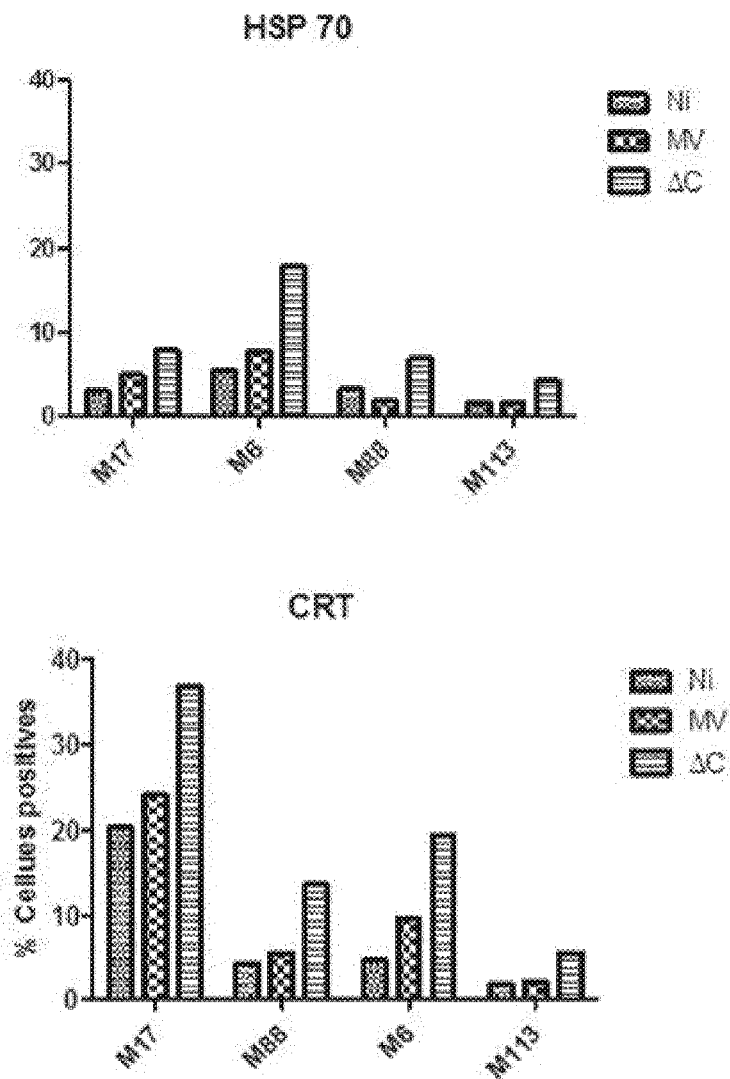

FIGS. 21A and 21B: Expression of "danger signals" after infection of melanoma cells by unmodified MV or MV-deltaC. (A) Example of flow cytometric analysis of the expression of HSP70 and with calreticulin (CRT) 24 h, 48 h and 72 h after infection by unmodified MV or MV-deltaC. (B) The membrane expression of the HSP70 protein and CRT in uninfected tumour cells and cells infected with unmodified MV and MV-deltaC (MOI=0.5) was determined at 72 h after infection by extracellular marking and flow cytometry.

Figure 22:
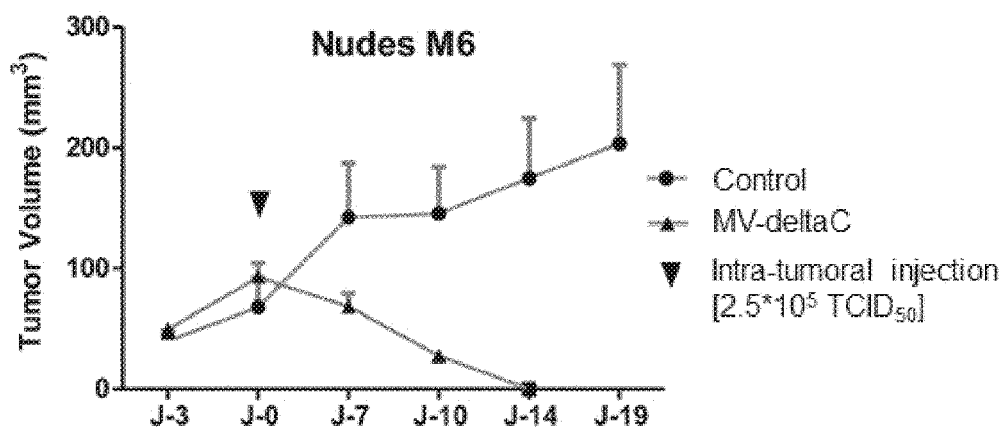

FIG. 22: In vivo melanoma tumour growth after intratumoral injection with MV-deltaC. Engrafted tumours were injected with PBS to visualize normal tumour growth as control. In these control mice, tumour volume increased from 45 mm³ to 150 mm³ within 13 days. In the group treated with MV-deltaC, a greater reduction of tumour volume was observed at 10 days after injection, which reached 25 mm³, and the tumours were eliminated at 14 days post injection.

Figure 23A:
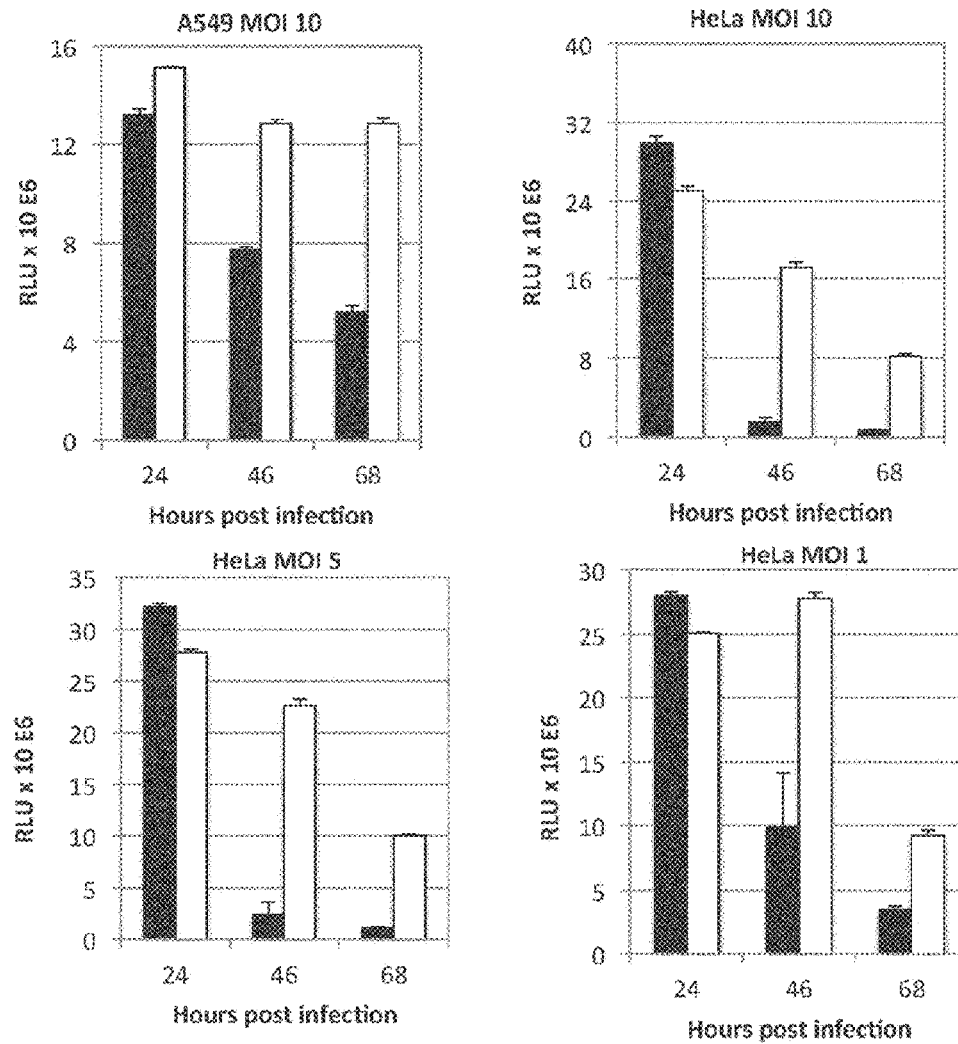
Figure 23B:
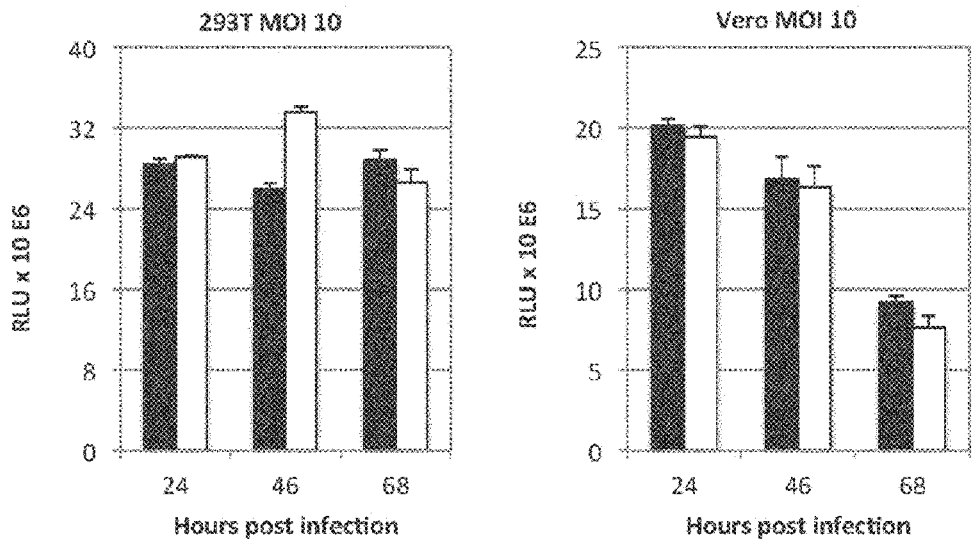

FIGS. 23A and 23B: Survival of cancer and non-cancer cells after infection with MV-deltaC or unmodified MV. Human A549 and Hela cancer cells (A) and HEK 293 and Vero non-cancer cells (B) were infected by MV-deltaC (black bars in graph) or unmodified MV (white bars in graph) at different MOI (triplicates). After 24, 46 and 68 hours of culture, the number of living cells was determined using CellTiter-GLO reagent, a luciferase-based assay that evaluates by ATP quantification the number of metabolically active cells in culture wells.

Figure 24:
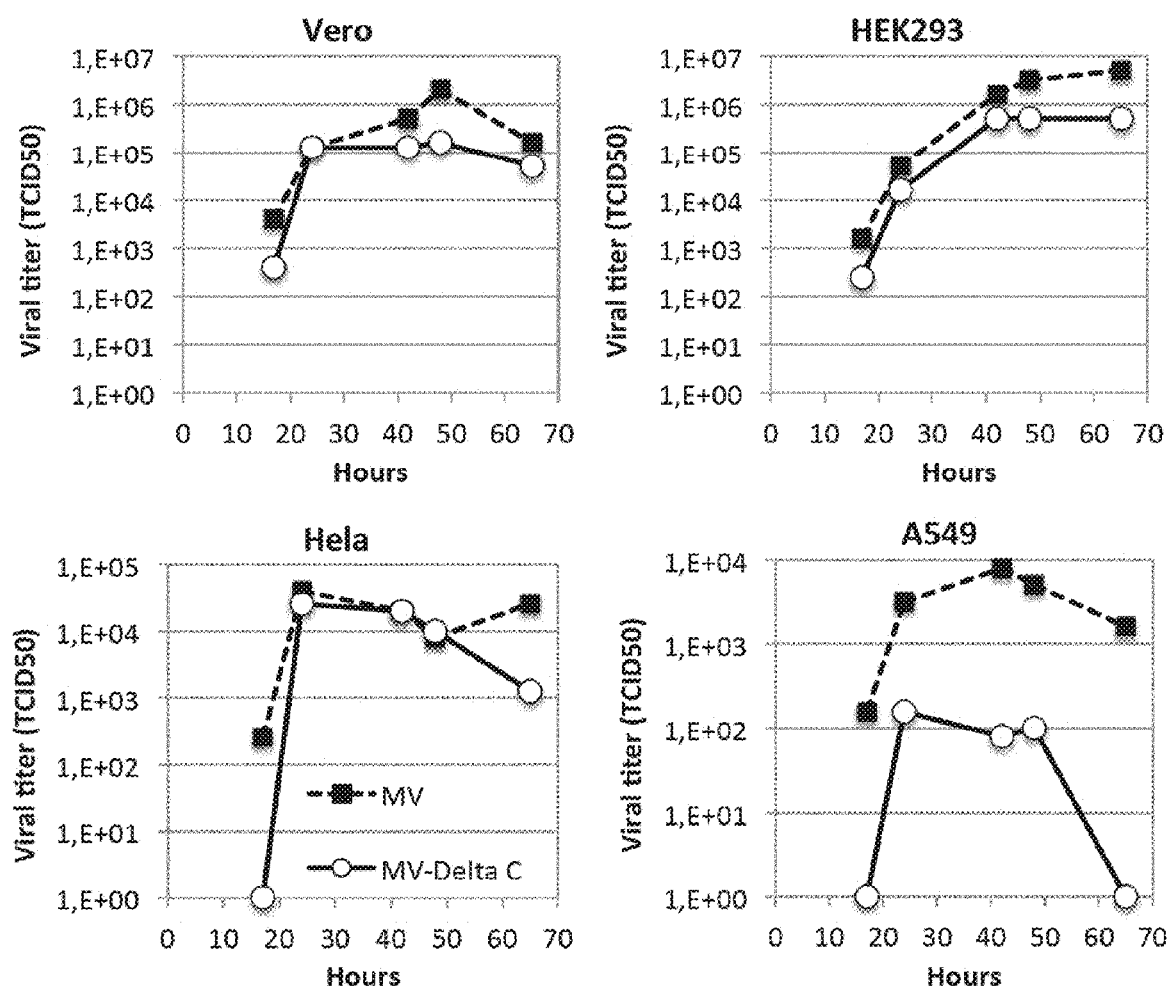

FIG. 24: Replication kinetics of unmodified MV and MV-deltaC on cancer and non-cancer cells. Human A549 and Hela cancer cells and HEK 293 and Vero non-cancer cells were infected by MV-deltaC or unmodified MV at MOI 1 (triplicates). Viral titers were determined as TCID50.

EXAMPLES

Example 1

Comparative Studies Between Unmodified MV and MV-DeltaC

In vitro infection with unmodified MV. Live-attenuated MV Schwarz strains were obtained from F. Tangy (Institut Pasteur, France). Schwarz MV was rescued from the pTM-MVSchw (deposited by Institut Pasteur at the CNCM (Paris, France) under number 1-2889 on Jun. 12, 2002) cDNA by use of the helper-cell-based rescue system described by Radecke (Radecke et al., *EMBO J.*, 1995, 14:5773-5784) and modified by Parks (Parks et al., *J. Virol.*, 1999, 73:3560-3566). Briefly, 293-3-46 helper cells were transfected with 5 μg of pTM-MVSchw and 0.02 μg of pEMC-Lschw expressing the Schwarz MV-L gene (Combredet et al., *J. Virol.*, 2003, 77:11546-11554). After an overnight incubation at 37° C., a heat shock was applied for 2 h at 43° C., and transfected cells were transferred onto a Vero cell monolayer. Syncytia that appeared in 15 days coculture were transferred to 35-mm wells and then expanded in 75-cm² and 150-cm² flasks of Vero cells culture in 5% FCS DMEM. When syncytia reached 80-90% confluence, the cells were scraped into a small volume of OptiMEM and frozen-thawed once. After low-speed centrifugation to pellet cellular debris, virus-containing supernatant was stored at −80° C. The titer of recombinant MV stock was determined by an endpoint limit-dilution assay on Vero cells. The TCID50 was calculated by use of Kärber method (Kärber, *Arch. Exp. Path. Pharmak.*, 1931, 162:480-483).

In Vitro Infection with MV-deltaC.

Figure 1B:
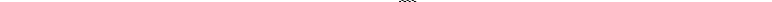

MV-deltaC was also rescued by reverse genetics on HEK293-T7-MV helper cells and amplified on Vero cells, in a similar process as the one described in WO2004/000876 for unmodified MV. The suitable cDNA clone encoding the MV-deltaC genome was accordingly prepared from purified viral particles of MV as disclosed in said application, or from plasmid pTM-MVSchw that was modified by mutation of the second "ATG" initiation codon present in the (+1) ORF at the N-terminal region of the P gene to give plasmid pTM-MVSchw-deltaC-ATU1 (eGFP). In particular, the "ATG" codon was replaced with an "ACG" codon by mutation of T to C (SEQ ID NO: 1) (FIG. 1B). Similarly a variant of MV-deltaC was also rescued by reverse genetics using a variant plasmid pTM-MVSchw-deltaC-ATU1 (eGFP) having the nucleotide sequence of SEQ ID NO: 2, wherein at position 2803 an additional substitution was carried out to replace the G nucleotide by an A nucleotide.

Characterisation of MV-DeltaC.

Figure 2:
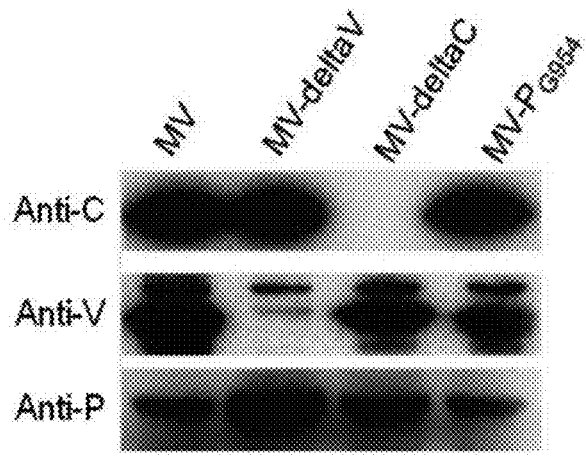
FIG. 2: Expression of the P, V and C proteins by MV, MV-deltaV, MV-deltaC and MV-P$_{G954}$. Lysates of Vero cells infected with the different viruses were fractionated on SDS-PAGE gel and the P, V, C proteins were detected by Western blot using specific monoclonal antibodies.

To confirm that the gene encoding the C protein was knocked out and that the P and V proteins were still expressed, a Western blot on lysates of infected Vero cells was carried out using specific monoclonal antibodies (anti-P; anti-V and anti-C, Takeuchi, K. Et al., *FEBS Letters*, 2003, 545 (2), 177-182) (FIG. 2).

Thus, the expression of P, V and C proteins by MVdelta-C was compared to the one obtained by MV, MV-deltaV (MV, in which the V protein was knocked out) and MV-$P_{G954}$(MV, in which the P gene was replaced by the P gene of a wild type strain (i.e. G954)). FIG. 2 shows that MV-deltaC did not express the C protein anymore, while the V and P proteins were correctly expressed. The stability of the mutation present in MV-deltaC was controlled by genome sequencing after 10 passages of the virus on Vero cells: no reversion was observed.

Growth Kinetics of MV-DeltaC.

The growth kinetics of MV-deltaC was analysed on different cell lines either competent or not for type I IFN response (FIG. 3). Vero cells (African green monkey epithelial cells) have a deletion in the IFN-β gene (Mosca, J. D., Pitha, P. M. *Mol Cell Biol.*, 1986, 6(6), 2279-2283), thus type I IFN response cannot be initiated in these cells upon viral infection. On the contrary, Hela (human carcinoma epithelial cells), Jurkat (human T lymphocytes) and U937 (human monocytes) are competent to initiate type I IFN response. As compared to other MV viruses tested on Vero cells, MV-deltaC grew rapidly during the first 24 hours, then its growth decreased suddenly. Growth arrest was confirmed on other cell types tested that are competent for type I IFN response (HeLa, Jurkat and U-937). Thus, in contrast to other studies (Takeuchi, K. Et al., *J. Virol.*, June 2005, 7838-7844; Patterson, J. B. et al., *Virology*, 2000, 267(1): 80-89), the growth deficit of MV-deltaC does not seem related to the presence or absence of IFN.

Cytopathic Effects of MV-DeltaC.

Several explanations could account for the sudden growth arrest of MV-deltaC. In fact, MV-infected Vero cells are characterised by the formation of giant syncytia (multinucleated cells) resulting from the fusion of infected cells expressing MV glycoproteins with neighbouring uninfected cells that express CD46 receptor. The inventors observed that MV-deltaC induced syncytia formation much faster than unmodified MV on Vero cells (FIG. 4) and all other cell types tested. From 24 hours of infection with a MOI of 1, Vero cells practically all merged into a giant syncytium, which broke out a few hours later. This explains the growth drop observed at 24 hours post-infection: no more naive cells remained alive in culture to support a productive infection. Premature apoptosis of infected cells is likely responsible for the observed viral growth arrest. A MV-deltaC derived from a pathogenic strain of MV (Ichinose) was previously shown to exert a higher cytopathic effect than the parental virus (Takeuchi, K. Et al., *J. Virol.*, June 2005, 7838-7844).

The exacerbated cell fusion induced by MV-deltaC could be due to a higher or earlier production of viral proteins, in particular H and F glycoproteins on the surface of infected cells that would promote rapid and massive cell fusion. The kinetics of viral hemmaglutinin (H) expression in HeLa cells infected with MV-deltaC or unmodified MV (MOI=1) was analysed using immunofluorescence. Cells were stained with a monoclonal anti-MV-H antibody coupled to FITC (FIG. 4). The result shows that at 24 hours post-infection, MV-deltaC causes a more massive infection and induces a much larger H expression than unmodified MV.

Kinetics of Viral Protein Expression in Vero Cells Infected with MV and MV-DeltaC.

Figure 5:
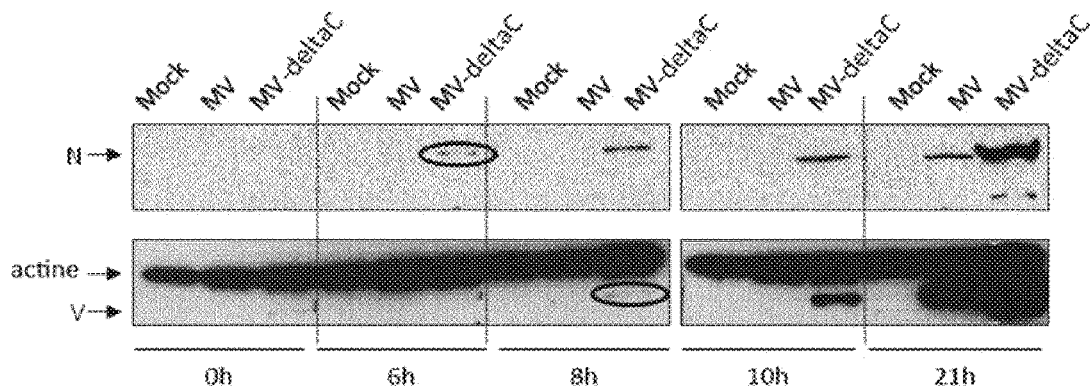
FIG. 5: Kinetics of viral protein expression in Vero cells infected with MV or MV-deltaC. Cells were infected at a MOI of 1, and then lysed at different time points. Cell lysates were analysed by Western blot, and viral proteins N and V were identified using specific monoclonal antibodies (anti-N clone 120, Naniche, D. et al., *J Gen Virol.*, 1992, 73(10): 2617-2624; anti-V, Takeuchi, K. Et al., *FEBS Letters*, 2003, 545 (2), 177-182).

To confirm the increased production of viral proteins in the absence of C protein expression, the content of viral proteins N and V in lysates of Vero cells infected with MV-deltaC or unmodified MV at an MOI of 1 was analysed over time (FIG. 5). From 6 hours of infection, the nucleoprotein N was detectable in cells infected with MV-deltaC, while it was only detectable after 21 hours of infection with unmodified MV. The same observation was made for the V protein. This result demonstrates that viral proteins are expressed much earlier and in higher amounts by MV-deltaC than by unmodified MV.

Immunogenicity of MV-DeltaC.

Figure 6A:
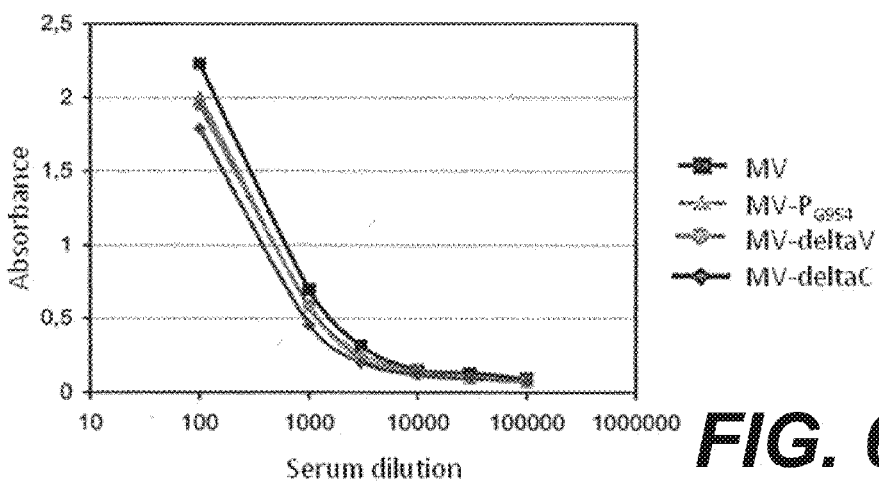
FIG. 6A to 6C: Anti-MV humoral response induced in CD46/IFNAR mice immunised with MV-P$_{G954}$, MV-deltaV or MV-deltaC. Antibody titers were determined by ELISA on sera collected 2 months after a single inoculation. (A) Limiting dilution assays of pooled sera from different groups of mice. (B) Individual titers per mouse. (C) Mean titers per group. Antibody titers were defined as the limiting dilution of tested sera giving twice the absorbance value calculated against that of sera from non-immunised mice.
Figure 6B:
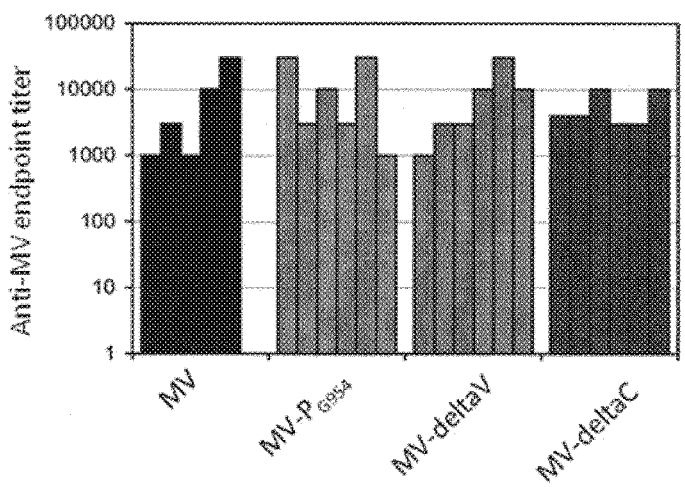
Figure 6C:
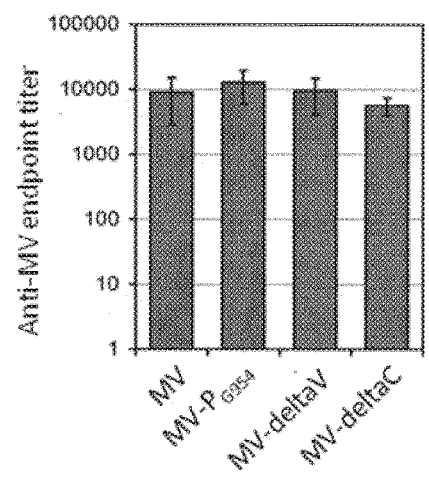

To assess the impact of the C protein expression silencing on the immunogenicity of MV vaccine vector, CD46+/−IFNAR−/− mice susceptible to MV infection were immunised (Combredet, C. et al., 2003, *J Virol*, 77(21): 11546-11554; Mrkic B. et al., *J Virol.*, 2000, 74(3):1364-1372). These mice are genetically engineered to express human CD46 receptor of MV vaccine strains and are disabled for the expression of type I IFN receptor (IFNAR). They are commonly used to assess the immunogenicity of MV vectors (Brandler, S. et al., *PLoS Neglected Tropical Diseases*, 2007, 1(3):e96; Combredet, C. et al., 2003, *J Virol*, 77(21): 11546-11554). Although IFN α/β is ineffective in these mice, this model was used to initially evaluate in vivo the impact of the C protein expression silencing. MV-deltaC was compared to unmodified MV, MV-deltaV and MV-$P_{G954}$. A single dose of $10^5$TCID50 of each virus was inoculated intraperitoneally into four groups of six mice. Sera were collected 2 months after inoculation and anti-MV antibodies were quantified by ELISA (Trinity Biotech) (FIG. 6).

In these mice incompetent to type I IFN, the antibody levels induced by modified measles vectors were comparable to those induced by unmodified vectors. This result is not surprising for MV-deltaV and MV-$P_{G954}$ vectors, which have in vitro growth kinetics similar to unmodified MV. Surprisingly, MV-deltaC vector, which has a reduced growth in vitro, induced antibody titers just barely lower than those induced by unmodified MV. This result indicates that either the inoculated dose was too high for a difference to be observed, or the minimum viral replication was sufficient to induce humoral response saturation. It was previously shown in monkeys that spread of MV-deltaC derived from a pathogenic strain of MV (Ichinose) was greatly reduced compared to wild type (Takeuchi, K. Et al., *J. Virol.*, June 2005, 7838-7844). These preliminary data indicate that in the absence of type I IFN response, silencing of the C protein does not affect the establishment of antiviral humoral response.

Example 2

Cell Death Induction by MV or MV-DeltaC

Cell Culture.

The epithelioid mesothelioma cell lines (Meso11, Meso13 and Meso56) and the lung adenocarcinoma cell lines (A549 and ADK117) were established and characterised (Gueugnon F et al., *Am J Pathol*, 2011, 178: 1033-1042) from pleural effusion collected by thoracocentesis of cancer patients, with informed consent. The melanoma cell lines (M17 and M18) were synthesised by B. Dreno and N. Labarriére (Cancer Research Centre, Nantes, France). The lung adenocarcinoma cell line (A549) was purchased from ATCC. The epithelioid mesothelioma cell lines (Meso11, Meso13 and Meso56) and the lung adenocarcinoma cell line (ADK117) were isolated and characterised by F. Tangy (Institut Pasteur, France). All cell lines were maintained in RPMI-1640 medium (Gibco-Invitrogen, Cergy-Pontoise, France) supplemented with 10% (v/v) heat-inactivated fetal calf serum (PAA Laboratories, Les Mureaux, France), 2 mM L-glutamine, 100 U/mL penicillin and 100 µg/mL streptomycin (all purchased from Gibco). Cells were cultured at 37° C. in a humidified, 5% $CO_2$ atmosphere and were routinely checked for *Mycoplasma* contamination by PCR.

Cell Death Analysis.

Cell death was determined 3 days after infection using the Apoptosis Detection Kit (BD Biosciences). Briefly, cells were double-stained with FITC-AnnexinV and propidium iodide for 15 min and analysed by flow cytometry within 1 h. MV- and MV-deltaC specific cell deaths were then determined. Cells were incubated with specific antibodies described in the following examples, for extracellular staining Cells were then washed 3 times with PBS before analysis by flow cytometry (FACSCalibur, BD Biosciences).

To compare the infection and cell death induction abilities with MV and MV-deltaC, a large panel of three epithelioid mesothelioma cell lines (Meso11, Meso13 and Meso56), two melanoma cell lines (M17 and M18) and two lung adenocarcinoma cell lines (A549 and ADK117) were infected with unmodified MV or MV-deltaC, at a Multiplicity Of Infection (MOI) of 1.0 for 2 hours, incubation at 37° C. Control cell lines were not infected with MV or MV-deltaC (FIG. 7). Tumour cells were analysed by flow cytometry after double staining with FITC-Annexin-V and propidium iodide three days after infection.

Figure 7A:
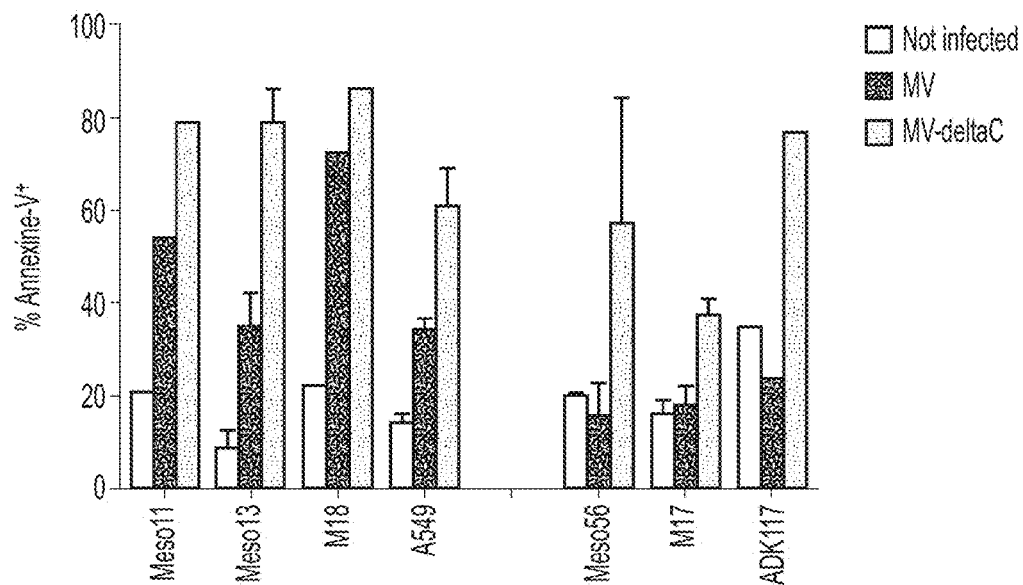
FIGS. 7A and 7B: Infection and cell death induction by MV-deltaC. A) Tumour cells were infected with MV or MV-deltaC (MOI=1, 2 h) and analysed by flow cytometry after double staining with FITC-Annexin-V and propidium iodide at 72 hours after infection. Data represent the percentages of Annexin-V cells.

Meso11 and Meso13 epithelioid mesothelioma cells, M18 melanoma cells or A549 lung adenocarcinoma cells were unmodified MV efficiently infected, while Meso56 epithelioid mesothelioma cells and ADK117 lung adenocarcinoma cells were unmodified MV weakly infected, and M17 melanoma cells were uninfected. Even if a moderate or important percentage of Annexin-V cells was observed for unmodified MV efficiently infected cells (Meso11 and Meso13 epithelioid mesothelioma cells, M18 melanoma cells and A549 lung adenocarcinoma cells), it was found that MV-deltaC was able to induce even more effectively the death of these tumour cells. While unmodified MV weakly infected (Meso56 epithelioid mesothelioma cells and ADK117 lung adenocarcinoma cells) or even uninfected (M17 melanoma cells) tumour cells showed a very low percentage of Annexin-V cells, the inventors have surprisingly discovered that infection with MV-deltaC induced a much higher cell death induction for these two cell lines (FIG. 7A).

Thus, according to these in vitro results, MV-deltaC induced a higher apoptosis in infected tumour cells than unmodified MV.

Example 3

Caspase-3 Activation After MV or MV-DeltaC Infection

Figure 7B:
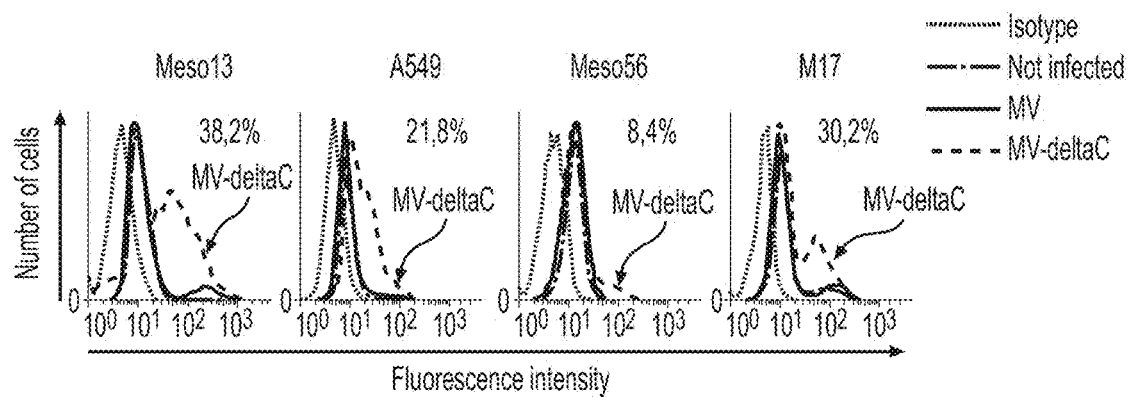

The caspase-3 activation was analysed both in tumour cells infected with unmodified MV and MV-deltaC (FIG. 7B). A panel of two epithelioid mesothelioma cell lines (Meso13 and Meso56), one melanoma cell line (M17) and one lung adenocarcinoma cell line (A549) were infected with unmodified MV or MV-deltaC, at a MOI of 1.0 for 2 hours, incubation at 37° C. Control cell lines were not infected with MV or MV-deltaC. Virus infected (MV or MV-deltaC) and uninfected tumour cells were analysed by flow cytometry after staining with an anti-caspase-3 antibody (BD Biosciences) three days after infection.

Infection with MV-deltaC induced caspase-3 activation for the two different tested cell lines: 38.2% for Meso13 epithelioid mesothelioma cells, 30.2% for M17 melanoma cells, 21.8% for A549 lung adenocarcinoma cells and 8.4% for Meso56 epithelioid mesothelioma cells. On the contrary, this caspase-3 activation was not or partially observed after infection with unmodified MV. These results suggested that unmodified MV and MV-deltaC viruses could induce the tumour cell death according to two different pathways.

Example 4

Exposure of the Hsp70 Protein to the Cell Surface After MV or MV-DeltaC Infection Tumour cell infection with oncolytic viruses can cause a cellular stress (Fabian et al., *J Virol*, 2007, 81(6): 2817-2830). Infection, but also cell death induced by these viruses, lead also to the production and release in the environment of molecules with immunogenic properties (Wang et al., *Viral Immunol*, 2006, 19(1): 3-9). These endogenous danger signals issued from infected cells can in fact be recognised by the defence cells and triggered adaptive responses. The monocyte-derived and plasmacytoid dendritic cells recognise these danger signals thanks to the expression of different receptors. The immune system is thus able to work in synergy with the direct oncolytic activity of viruses by activating a specific lymphatic response of tumour antigens.

Infection by tumour cells with the vaccine strain of the oncolytic MV virus allows for the maturing of DC and the activation of autologous T lymphocytes (WO2009/047331). In order to characterise the mechanism by which infected cells induced the immune system activation, the expression, the modification and/or the release of different cellular factors known for their involvement in cell death immunogenicity have been studied by the inventors. For example, HSP70 family proteins or calreticulin can be involved in the activation of the antitumour immune response.

Expression of the Hsp70 protein to the surface of unmodified MV and MV-deltaC infected tumour cells was analysed (FIG. 8). A panel of two epithelioid mesothelioma cell lines (Meso13 and Meso56), one melanoma cell line (M17) and one lung adenocarcinoma cell line (A549) were infected with unmodified MV or MV-deltaC, at a MOI of 1.0 for 2 hours, incubation at 37° C. Control cell lines were not infected with MV or MV-deltaC. The membrane Hsp70 protein expression was determined two days after infection for Meso13 and Meso56 epithelioid mesothelioma cells or three days after infection for A549 lung adenocarcinoma and M17 melanoma cells, by extracellular staining and flow cytometry.

A very small translocation of Hsp70 protein to the cell surface was observed both for unmodified MV efficiently infected cells (Meso13 epithelioid mesothelioma cells and A549 lung adenocarcinoma cells) and MV resistant cells (Meso56 epithelioid mesothelioma cells and M17 melanoma cells). On the contrary, MV-deltaC surprisingly induced a strong exposure of the Hsp70 protein to the outer layer of the plasma membrane for all cell lines. These results suggested that cell death induced by MV-deltaC showed immunogenic characteristics.

Example 5

Membrane Translocation of Calreticulin After MV or MV-DeltaC Infection

The impact of tumour cell infection with unmodified MV and MV-deltaC on the translocation of calreticulin to the cell surface was studied. To do so, the presence of calreticulin to the infected tumour cell surface was analysed by extracellular staining (FIG. 9). A panel of two epithelioid mesothelioma cell lines (Meso13 and Meso56), one melanoma cell line (M17) and one lung adenocarcinoma cell line (A549) were infected with unmodified MV or MV-deltaC, at a MOI of 1.0 for 2 hours, incubation at 37° C. Control cell lines were not infected with MV or MV-deltaC. Uninfected and infected (MV or MV-deltaC) tumour cells were stained with an anti-calreticulin antibody and a Cy5 conjugated anti-mouse secondary antibody two days after infection for Meso13 and Meso56 epithelioid mesothelioma cells or three days after infection for A549 lung adenocarcinoma cells and M17 melanoma cells. Cells were then analysed by flow cytometry.

Like the Hsp70 protein, infection with MV-deltaC surprisingly lead to a stronger translocation of calreticulin to the cell surface than unmodified MV, both for unmodified MV efficiently infected cells (Meso13 epithelioid mesothelioma cells and A549 lung adenocarcinoma cells) and MV resistant cells (Meso56 epithelioid mesothelioma cells and M17 melanoma cells). These results also suggest that cell death induced by MV-deltaC showed immunogenic characteristics.

Example 6

Release of HMGB-1 in the Extra-Cellular Environment After MV or MV-DeltaC Infection The release of the HMGB-1 protein in the extracellular medium after infection of tumour cells with unmodified MV or MV-deltaC was studied (FIG. 10). Two epithelioid mesothelioma cell lines (Meso13 and Meso56) were infected with unmodified MV or MV-deltaC, at a MOI of 1.0 for 2 hours, incubation at 37° C. Control cell lines were not infected with MV or MV-deltaC. Supernatants of uninfected or infected (MV or MV-deltaC) tumour cells were collected one day, two days or three days after infection and stored at −20° C. The quantity of HMGB-1 in these supernatants was then determined by ELISA.

MV-deltaC induced the effective release of HMGB-1 by infected tumour cells. Infection with MV-deltaC induced a more rapid apoptosis of the tumour cells in culture; as a consequence, MV-deltaC induced an earlier release of HMGB-1 compared to unmodified MV, as shown by the results of Meso13 epithelioid mesothelioma cells.

Example 7

Plasmacytoid Dendritic Cells

Cell Culture

Cell lines were cultured as previously described in Example 2.

MV Infection and UV Irradiation

Live-attenuated Schwarz-strain MV and recombinant MV-enhanced green fluorescent protein (MV-eGFP) were produced as previously described (Gauvrit, A. et al., *Cancer Res.*, 2008, 68: 4882-4892). MV infection of tumour cells was performed for 2 hours at 37° C. with a multiplicity of infection (MOI) of 1 unless otherwise indicated. Viral inoculum was then replaced by fresh cell medium for 72 hours. For pDC infection and maturation experiments, MV was not washed and stayed in the medium throughout the culture. Measurement of infection rate was performed by flow cytometry using MV-eGFP at 24, 48, and 72 hours post-infection. All other experiments were carried out using MV. Tumour cells were irradiated with UV-B (312 nm-100 kj/m$^2$, Stratalinker, Stratagene). Medium was renewed every 72 hours.

DC Isolation and Culture pDCs were obtained from healthy donor PBMCs (Etablissement Français du Sang, Nantes, France) as previously described (Coulais, D. et al., *Cytotherapy*, 2012, 14:887-896). Briefly, pDCs were first enriched by counterflow centrifugation and then purified by magnetic bead negative selection as recommended in the manufacturer's protocol (Stemcell Technologies, Grenoble, France). The purity of untouched pDCs was always greater than 96%. pDCs ($3 \times 10^5$ per mL) were maintained in culture with 20 ng/mL rhIL-3 (Sigma, Saint Quentin Fallavier, France) or activated in vitro with a TLR-7 agonist, R848 (InvivoGen, San Diego, USA) (5 µg/mL). pDCs were also co-cultured with MV alone, MV and IL-3 (MOI=1), or MV-infected or UV-irradiated tumour cells (pDC/tumour cell: 1/1) without rhIL-3 or maturation agent. After 18 hours, culture supernatants and pDCs were harvested for use. For the TLR-7 inhibition assay, immunoregulatory DNA sequences were used, which specifically inhibited signaling via TLR-7 [IRS 661], at concentrations ranging from 0.1 µM to 1 µM (Eurofins, Munich, Germany). As a control, CpG-A at 5 µg/mL was used to induce a TLR-9-dependent IFN-α secretion by pDC (InvivoGen, San Diego, USA).

Immunofluorescence and Flow Cytometry

The phenotypes of pDCs were determined by immunofluorescence followed by flow cytometry. pDCs were stained with monoclonal antibodies specific for CD40, CD86, HLA-DR (BD Biosciences, San Jose, Calif., USA), CD83 (BioLegend, San Diego, Calif.—USA) and BDCA-4 (Miltenyi Biotec). pDCs were gated as BDCA-4+/HLA-DR+ cells, to differentiate them from tumour cells. Tumour cell death was measured by TO-PRO®3 (Invitrogen, Saint Aubin, France) staining as recommended by the manufacturer. TO-PRO®3 is a carbocyanine monomer nucleic acid with far-red fluorescence that enters only in dead cells and stains the DNA. Fluorescence was analysed on FACSCantoll (Becton Dickinson, N.J., USA) using FlowJo software.

Phagocytosis Assay

MV-infected and UV-irradiated tumour cells were stained with PKH-67 according to the manufacturer's protocol (Sigma, Saint Quentin Fallavier, France) and co-cultured with pDCs, for 18 hours at 4° C. or 37° C. (1 DC:1 tumour cell). Co-cultures were washed with PBS-EDTA to dissociate the cell-conjugate. pDCs were stained by an HorizonV450-conjugated, anti-HLA-DR-antibody (BD Biosciences, SanJose, Calif., USA) and analysed by flow cytometry (FACSCantoll, BD). pDC phagocytosis was observed by confocal microscopy (Nikon). MV-infected and UV-irradiated tumour cells were stained with PKH-67 and then co-cultured with pDCs in 24-well plates containing poly-lysine glass slides, for 18 hours (pDC:tumour cell, ratio 1:1). pDCs were stained with uncoupled anti-HLA-DR (BD Bioscience). HLA-DR staining was revealed with a secondary anti-mouse IgG antibody coupled to AlexaFluor 568.

Cytokine Detection

IFN-α (MabTech, Cincinnati, Ohio-USA) production was measured by ELISA on pDC culture supernatants according to the manufacturer's instructions.

Cross-Presentation Assay

NYESO-1$^{pos}$/HLA-A*0201$^{neb}$ g melanoma (M18) and NYESO-1$^{neb}$/HLA-A*0201$^{neg}$ pulmonary adenocarcinoma (A549) cell lines were MV-infected or UV-B irradiated, cultured for 72 hours and then co-cultured with HLA-A*0201$^{pos}$ pDCs (pDC:tumour cell ratio 1:1). After 18 hours, pDCs were co-cultured with the HLA-A*0201/NYESO-1(156-165)-specific CD8$^+$ T cell clone, M117.167, for 6 hours in the presence of Brefeldin-A (Sigma, Saint Quentin Fallavier, France). The M117.167 clone was obtained by cloning in a limiting dilution of tumour-infiltrating lymphocytes from a melanoma patient. The clone was cultured as previously described (Fonteneau, J. F. et al., *J Immunol Methods*, 2001, 258: 111-126). As a control, the inventors used pDCs that were pulsed for 1 hour with 0.1 or 1 µM NYESO-1(156-165) peptide and washed. Cells were then fixed with PBS containing 4% paraformaldehyde, for 10 min at room temperature, and permeabilised and stained with IFN-γ and CD8-specific antibodies (BD Biosciences, SanJose, Calif., USA), as previously described (Schlender, J. et al., *J Virol.*, 2005, 79: 5507-5515). IFN-γ production was analysed by flow cytometry with a gate on CD8+ T cells.

Real-Time RT-PCR

One microgram of total RNA was reverse-transcribed using Moloney murine leukemia virus reverse transcriptase (InVitroGen, Saint Aubin, France). PCR reactions were performed using QuantiTect primers (Qiagen, Foster City-USA) and RT$^2$ Real-Time SYBR-Green/ROX PCR mastermix (Tebu-bio, Le Perray-en-Yvelines, France), according to the manufacturers' instructions.

Statistics

GraphPad Prism (Inc., San Diego, Calif.—USA) software using a nonparametric Mann Whitney comparison test was used. P values <0.05 were considered to be statistically significant.

Example 8

Sensitivity of Tumour Cells and pDC to MV Infection

Figure 11A:
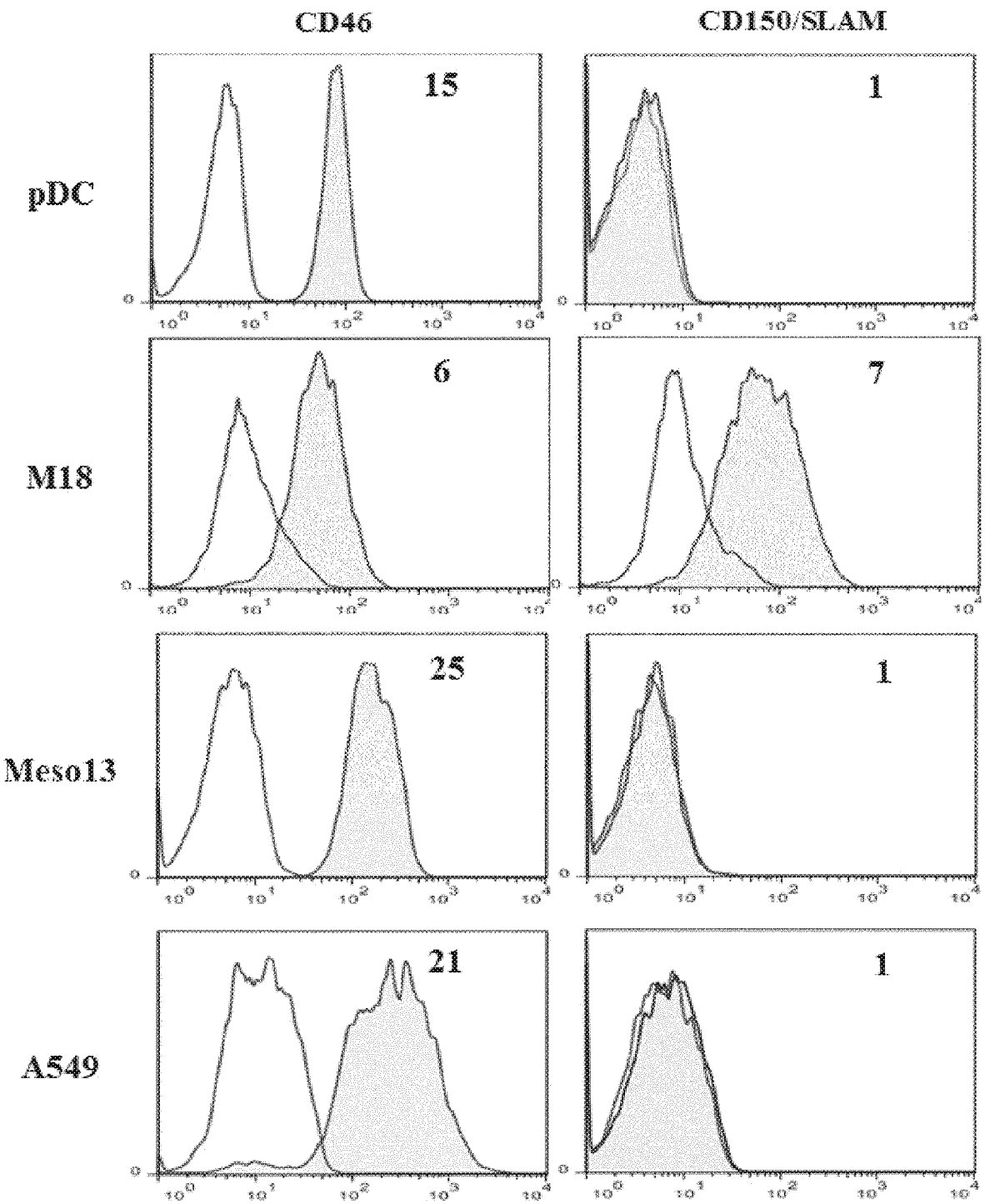

During infection, MV enters cells mainly via the CD46 and, to a lesser extent, CD150/SLAM (Anderson, B. D. et al., Cancer Res., 2004, 64: 4919-4926; Schneider, U. et al., J Virol., 2002, 76: 7460-7467). In a first experiment, the inventors studied the expression of these two major MV receptors, CD46 and CD150/SLAM, on pDC, melanoma (M18), mesothelioma (Meso13) and pulmonary adenocarcinoma (A549) cell lines (FIG. 11A). CD46 expression was observed on all cell types, with higher expression on Meso13 and A549 cell lines. Regarding CD150/SLAM expression, a positive expression on the M18 melanoma cell line was found. These results suggest that all these cell types may be sensitive to MV infection, as they all express CD46.

Figure 11B:
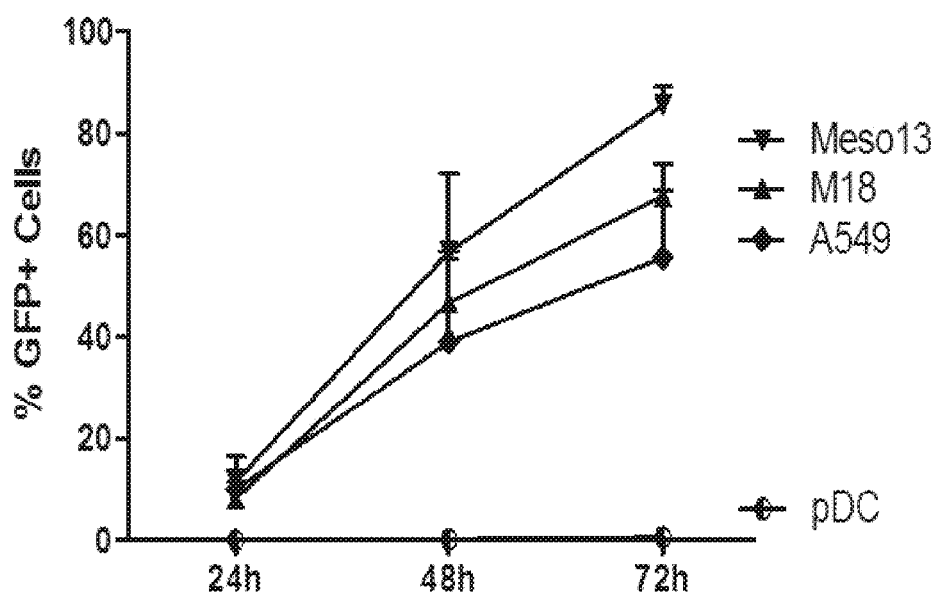
Figure 11C:
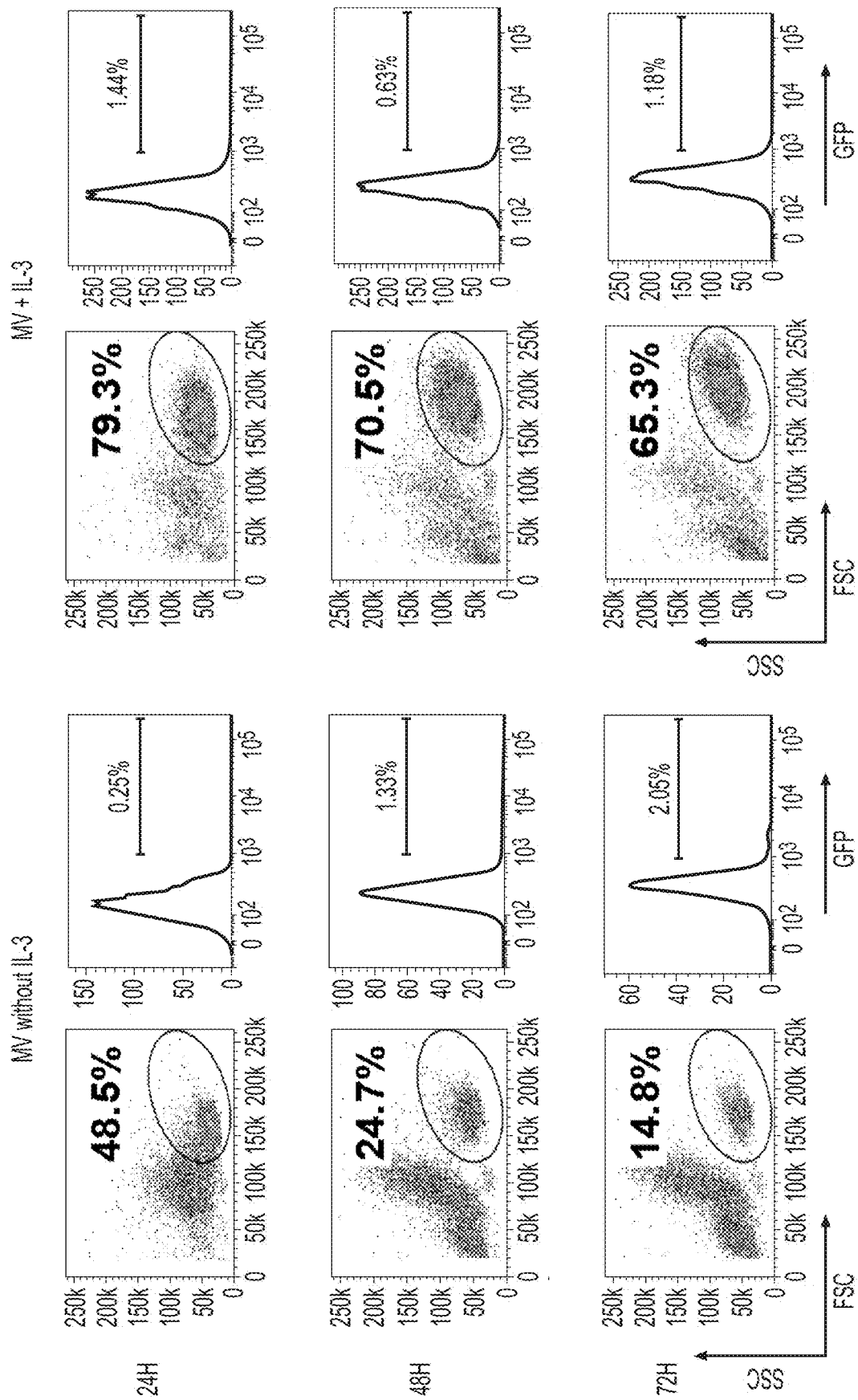
Figure 11D:
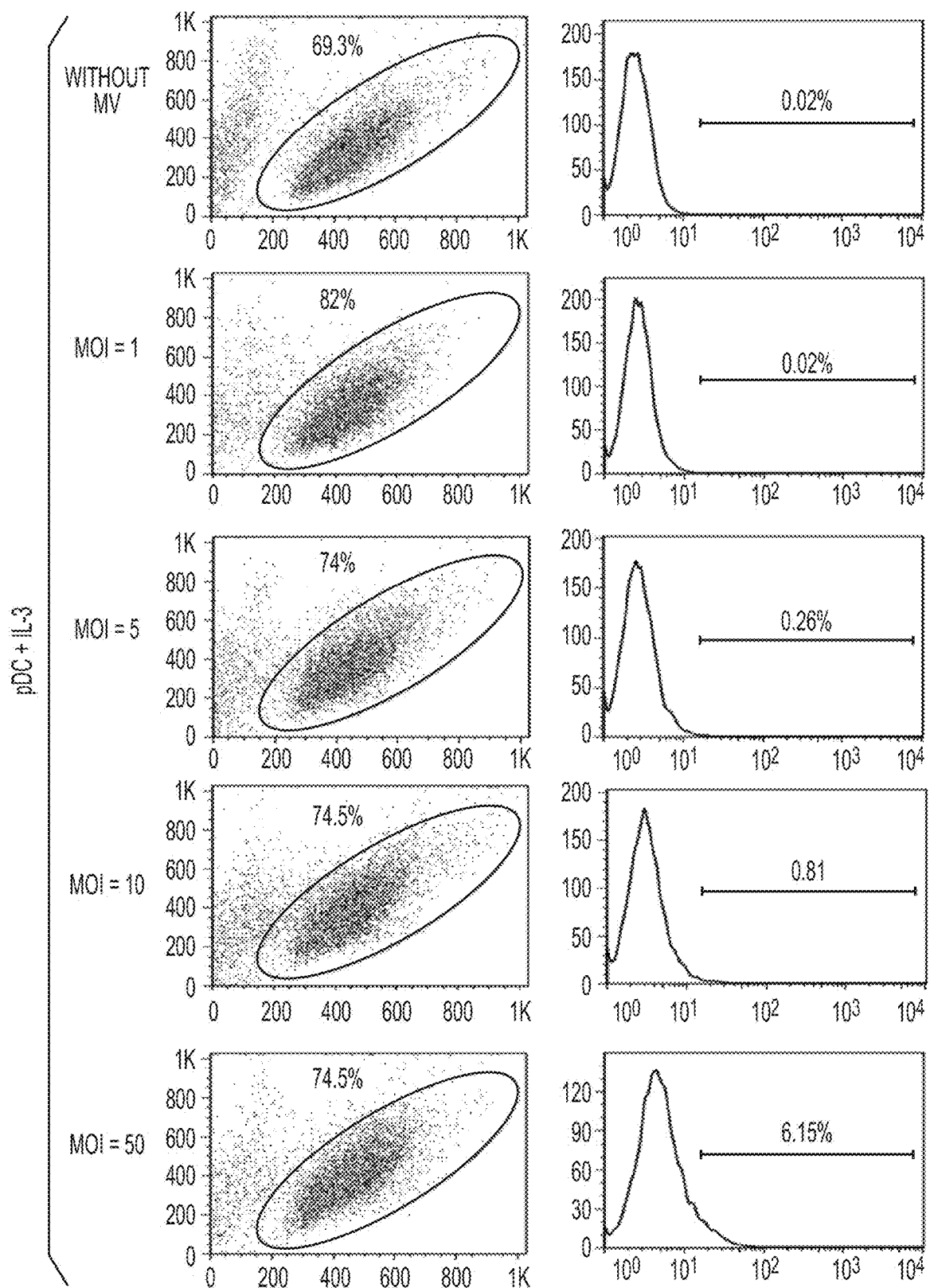

The inventors then studied the sensitivity to MV infection of these four cell types using a recombinant MV encoding the green fluorescent protein (MV-GFP). Seventy-two hours after exposure to MV with a MOI=1, the three tumour cell lines were productively infected with MV, ranging from 50% of A549 cells positive for GFP to 90% of Meso13 cells (FIG. 11B). Furthermore, syncytia formation was observed for the three tumour cell lines and pDCs were not permissive at MOI=1. Without a survival signal such as IL-3, the pDCs died during the 72 hours of culture. Thus, experiments were performed where IL-3 was added to the pDCs exposed to MV (FIG. 11C). In the presence of IL-3, the pDCs survived during the 72 hours, but were not productively infected by MV. To confirm this result, the MOI was increased up to 50 in the presence of IL-3, but the inventors still failed to detect infected pDCs (FIG. 11D). However, a small shift of fluorescence was observed at MOI=50, which was probably due to uptake of soluble GFP during the 72 hour culture, which contaminated the MV-GFP preparation. Similarly, when the inventors used UV-irradiated MV-GFP, which was not able to replicate, this slight fluorescence shift was still observed (FIG. 12). Finally, when the MV-GFP was incubated for 2 hours at MOI=50 with pDCs and washed, the inventors failed to detect the small shift of fluorescence 70 hours later (FIG. 12).

Figure 11E:
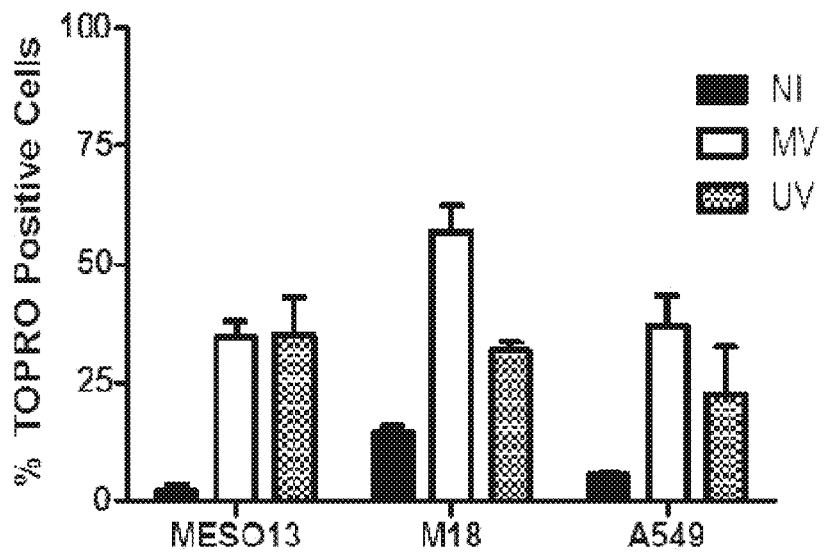

The inventors then measured tumour cell death 72 hours after infection and found that nearly half of MV-infected tumour cells were TO-PRO+ after 72 hours (FIG. 11E). A similar level of cell death was observed by irradiating the tumour cells with UV-B. Thus, MV infection induces tumour cell death for approximately half of the tumour cells 72 hours after infection.

Example 9

MV-Infected Tumour Cells Induce Maturation of pDCs

The inventors next investigated the effects of MV alone and MV-infected cells on pDC maturation (FIG. 13). In these experiments, they evaluated how MV infection of tumour cells in comparison with UV irradiation, another inducer of tumour cell death, affects pDC maturation. As a control for maturation, pDCs were exposed to the TLR7/8 agonist, R848 (FIGS. 13A and 13B).

It has been previously demonstrated that the MV-infected malignant pleural mesothelioma (MPM) tumour cell line, Meso13, induced maturation of monocyte-derived DCs, without additional adjuvants, whereas the virus alone or UV-irradiated Meso13 did not (Gauvrit, A. et al., Cancer Res., 2008, 68:4882-4892). The inventors performed a set of experiments on pDCs to determine the effects of MV alone, MV-infected or UV-irradiated tumour cells on pDC maturation status. The effect of MV-infected and UV-irradiated tumour cells was compared on the maturation status of pDCs (FIG. 13). Maturation of pDCs co-cultured with MV-infected tumour cells was observed, whereas UV-irradiated tumour cells failed to activate pDCs. Indeed, CD83 maturation marker expression was induced by MV-infected cells to a similar level as the one observed when the pDCs were exposed to R848. The inventors observed an induction of the expression of the costimulation molecules, CD40 and CD86, on pDCs exposed to MV-infected tumour cells, although this induction was low compared with the levels triggered by R848 alone.

Two studies have been reported which describe conflicting results on the ability of MV alone to trigger pDC maturation (Duhen, T. et al., Virus Res., 2010, 152: 115-125; Schlender, J. et al., J Virol., 2005, 79: 5507-5515). However, the study from Duhen et al., reporting that MV activates pDCs, was performed in the presence of IL-3, a pDC survival factor, whereas the other study from Schlender et al., who observed that pDCs cultured with MV does not induce pDC maturation, was carried out without IL-3. Thus, the inventors performed and compared the two conditions and found similar results to those described by these two authors. Indeed, MV at MOI=1 induced pDC maturation only in the presence of IL-3 (FIG. 13). As observed for R848 alone, MV in the presence of IL3 induced pDC maturation, mainly characterised by a significant increase of CD83 and, to a lesser extent, CD40 and CD86 expression. The inventors also observed survival and maturation of pDCs in the absence of IL-3 only when they were exposed to a high quantity of MV (MOI=50). At a lower viral concentration in the absence of IL-3, the pDCs died.

Figure 14A:
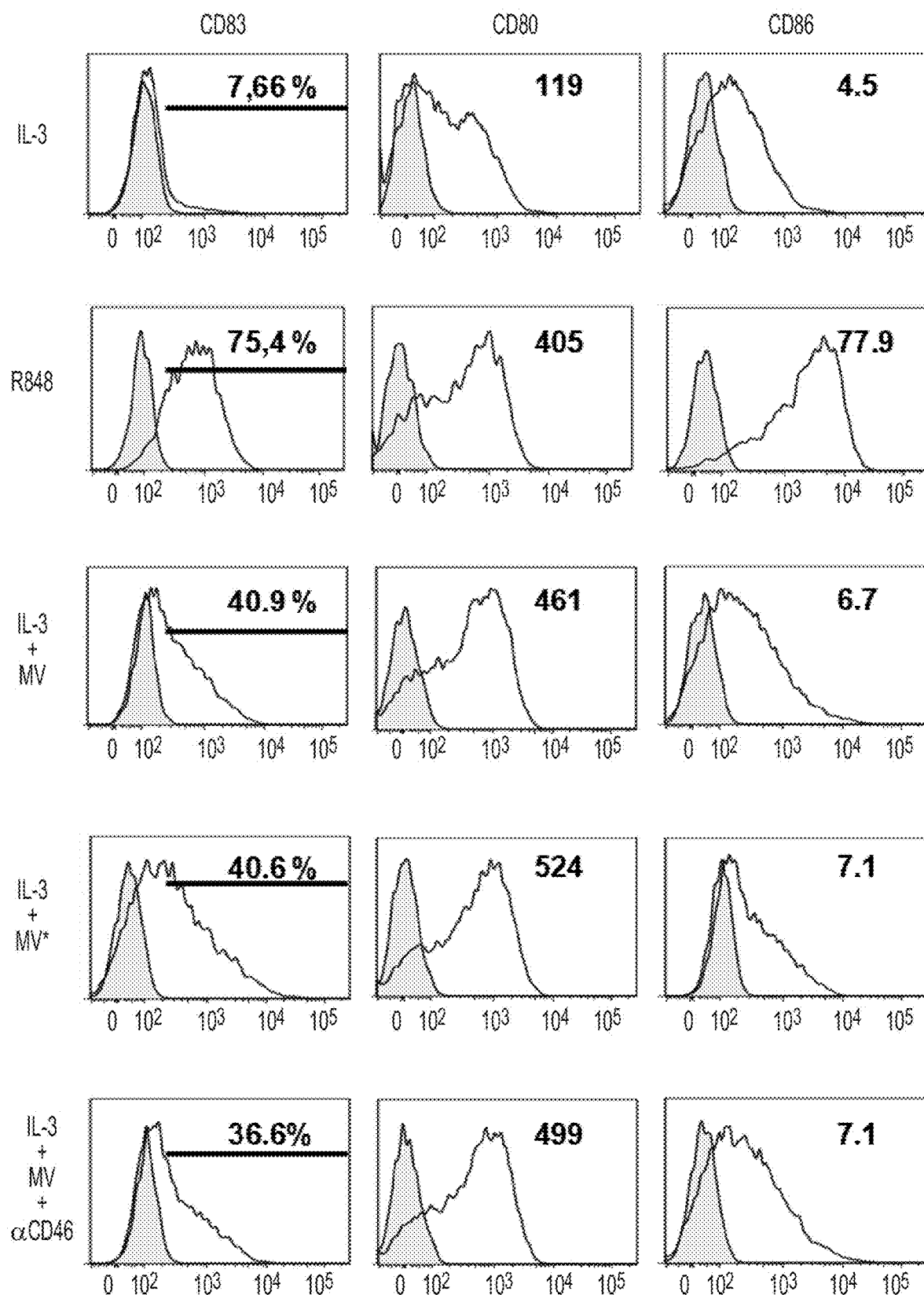
Figure 14B:
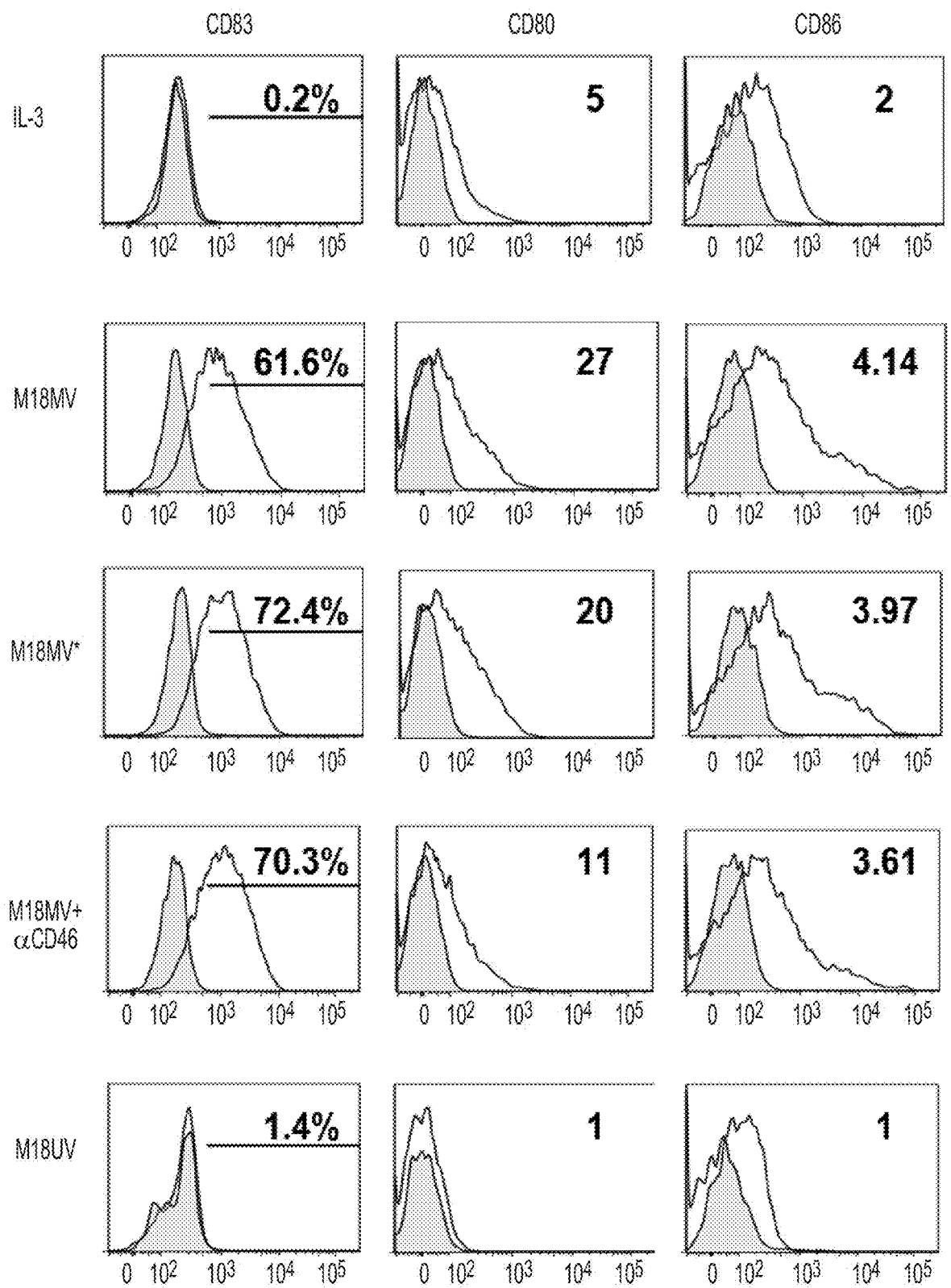
Figure 14C:
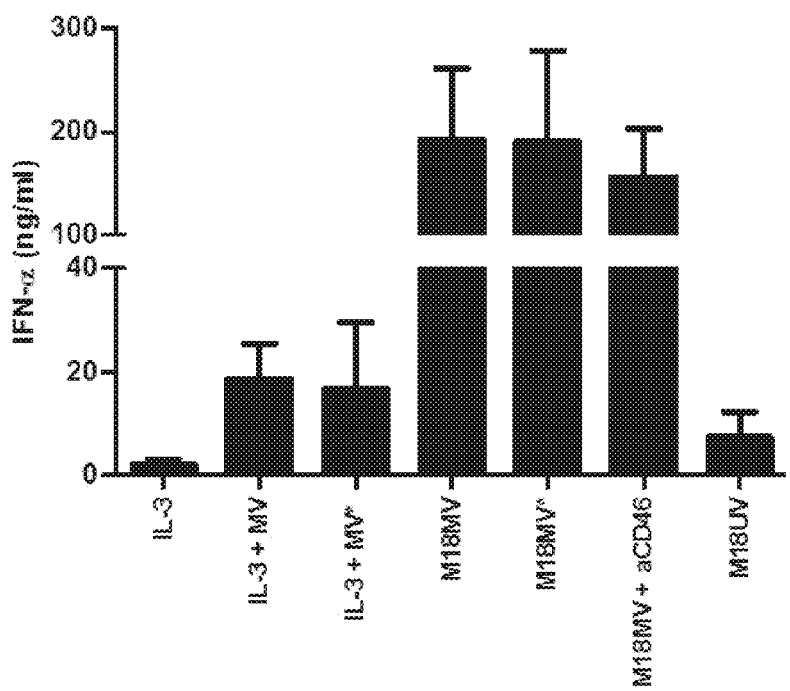
Figure 14D:
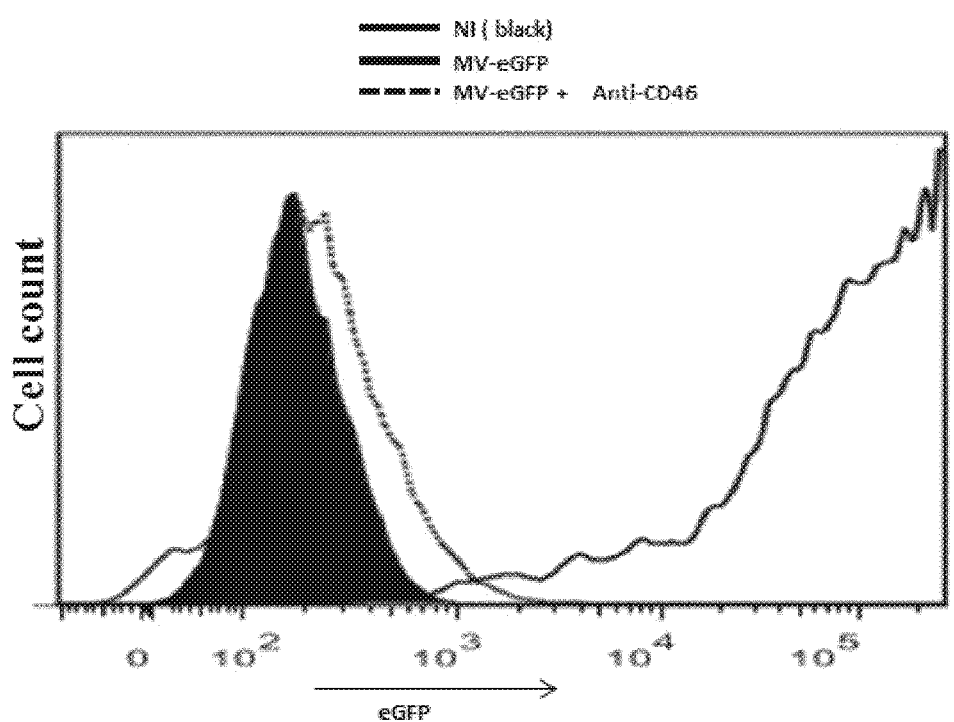

In the last set of experiments, the inventors tested whether MV infection and replication in pDCs were needed to induce their activation. pDCs were exposed to UV-irradiated MV (MV*), which is unable to replicate, and a similar level of maturation (CD83, CD80 and CD86 expressions) and IFN-α production was observed as with non-irradiated MV (FIGS. 14A and 14C). The presence of a blocking anti-CD46-specific antibody in the culture of pDCs exposed to IL-3 and MV did not affect maturation of pDCs (FIG. 14A). The same experiment was performed with pDCs exposed to MV-infected tumour cells. Maturation and IFN-α production were still observed when MV-infected tumour cells were UV-irradiated before exposure to pDCs (FIGS. 14B and 14C). Finally, the inventors tested whether a CD46-specific monoclonal antibody was able to inhibit pDC maturation in response to MV-infected tumour cells (FIGS. 14B and 14C). Inhibition was not observed, whereas the anti-CD46 antibody completely inhibited infection of Meso13 as a control (FIG. 14D). Altogether, these results suggest that MV infection and replication in pDCs are not necessary for pDC activation in response to MV.

Example 10 pDC Capture Cellular Components from MV-Infected Tumour Cells

Due to endo/lysosomal expression of TLR-7 and TLR-9, pDCs are specialised in viral nucleic acid detection (Gilliet, M. et al., Nat Rev Immunol., 2008, 8: 594-606). These two receptors are the major innate receptors that activate pDCs (Reizis, B. et al., *Nat Rev Immunol.*, 2011, 11: 558-565). Since MV, in the presence of IL-3 or MV-infected tumour cells, are able to induce pDC maturation, it is likely that the maturation stimulus is MV ssRNA, which activates TLR7 in the endo/lysosomal compartment. This hypothesis is strengthened by the fact that MV alone does not induce DC maturation, as these cells do not express TLR7 in humans. This implies that some MV particles are endocytosed by pDCs when they are cultured with MV and IL-3 or with MV-infected cancer cells. The inventors then investigated whether pDCs efficiently took up cellular material from MV-infected and UV-irradiated tumour cells (FIG. 15). MV-infected and UV-irradiated M18 and A549 tumour cells were labeled with PKH67 and co-cultured with pDCs. The inventors observed that pDCs efficiently took up MV-infected tumour cells at 37° C., whereas UV-irradiated tumour cells were less efficiently taken up (FIGS. 15A and 15B). In two additional experiments, the inventors observed that the presence of the CD46 monoclonal antibody in the culture did not inhibit phagocytosis of MV-infected tumour cells.

These results were confirmed by confocal microscopy (FIG. 15C). pDCs were co-cultured for 18 hours with PKH-67-labeled, MV-infected tumour cells. The optical sections showed fluorescent fragments of MV-infected tumour cells inside the pDCs, confirming the internalisation of MV-infected tumour cell pieces by pDCs. Interestingly, the inventors never observed syncitia formation between pDCs and tumour cells. Altogether, these results suggest that some MV particles contained in infected tumour cells could access compartments where TLR7 is located.

Example 11

MV-Infected Tumour Cells Induce Strong Type-I IFN Secretion by Triggering TLR7 pDCs are known to be the strongest producers of type-I IFN, notably against virus, upon TLR-7 or TLR-9 activation (Gilliet, M. et al., *Nat Rev Immunol.* 2008, 8:594-606). Thus, the inventors measured IFN-α production by pDCs following exposure to MV, MV-infected or UV-irradiated tumour cells, by ELISA (FIG. 16A). Direct exposure to MV induced IFN-α secretion by pDCs only in the presence of IL-3, matching the cell maturation observed earlier in FIG. 13. The amount of IFN-α produced in response to MV in the presence of IL-3 was comparable with the amount induced by R848 alone, a potent TLR7/8 agonist. Strikingly, the inventors found high amounts of IFN-α in co-culture supernatants after exposure of pDCs to MV-infected tumour cells (20-40 times more than what was observed in response to MV in the presence of IL-3 or R848 alone). These high quantities of IFN-α were produced by the pDCs, since tumour cells did not produce IFN-α or a very low amount (pg/mL range) after MV infection. UV-irradiated A549 or M18 tumour cells did not induce IFN-α production by pDCs. These results show that MV-infected tumour cells are able to trigger the production of high levels of IFN-α by pDCs, considerably higher than the levels produced by pDCs exposed to MV in the presence of IL-3 or to R848 alone.

The inventors have previously shown that, three days after infection of the Meso13 tumour cell line, a large amount of virus was produced, reaching $1 \times 10^8 TCID_{50}/mL$ corresponding to an MOI greater than 100 from a starting dose of virus of $1 \times 10^6 TCID_{50}/mL$, corresponding to an MOI=1 (Gauvrit, A. et al., *Cancer Res.*, 2008, 68: 4882-4892). It was thus likely that the huge quantity of IFN-α produced by pDCs in response to MV-infected tumour cells was the result of the intense MV replication in these tumour cells. To test this hypothesis, pDCs were cultured in the presence of increasing MOI ranging from 1 to 50, with or without IL-3 (FIG. 16B). In the presence of IL-3, the inventors observed that IFN-α production by pDCs increased with the MOI. On the contrary, pDCs did not produce IFN-α in the absence of IL-3, except for the highest MOI (MOI=50). These results suggest that the level of IFN-α production by pDCs is dependent on the quantity of MV and the presence of either IL-3 or other survival signals, explaining the huge quantity of IFN-α produced in response to the high titer of virus after infection of tumour cells.

Since MV and MV-infected tumour cells contain viral ssRNA, it is likely that IFN-α production by pDCs is mainly due to the triggering of TLR-7. Thus, an inhibition of TLR7 was carried out. Specific immunoregulatory DNA sequences (IRS) that inhibit IFN-α expression mediated by TLR-7 (IRS661) were used (Barrat, F. J. et al., *J Exp Med.*, 2005, 202: 1131-1139). The inventors showed that IFN-α production by pDCs cultured in the presence of MV and IL-3 was inhibited when the IRS661 was added (FIG. 16C). A similar IFN-α inhibition was also observed when IRS661 was added to pDCs exposed to MV-infected tumour cells. As a control, it was showed that IRS661 did not inhibit the CpG-A-induced IFN-α production by pDCs, which is TLR9 dependent. Altogether, these results demonstrate that IFN-α production induced by MV or MV-infected cells is TLR7 dependent.

Figure 17A:
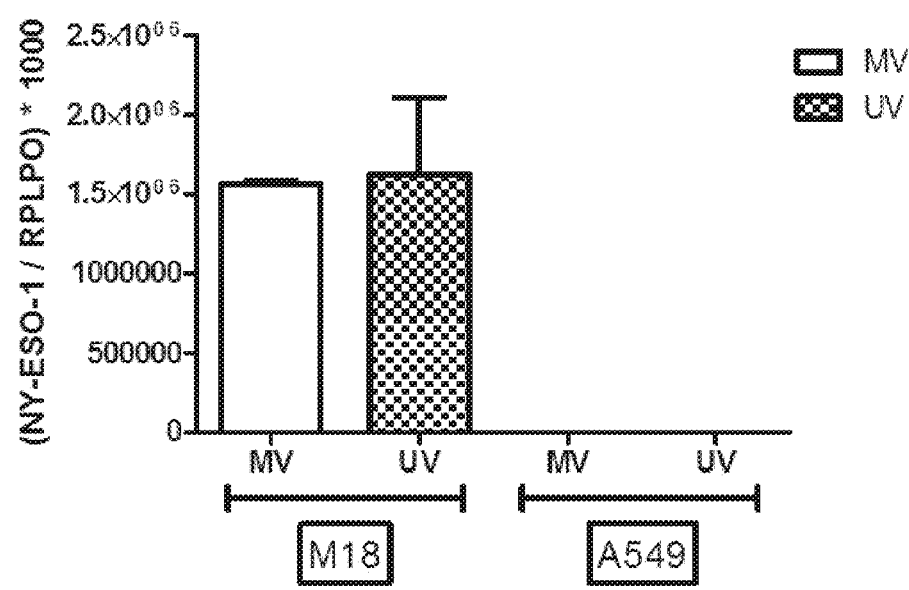

Example 12 pDCs are Able to Cross-Present a Tumour-Associated Antigen from MV-Infected Tumour Cells The capacity of human pDCs to cross-present viral antigens has been reported (Di Pucchio, T. et al., *Nat Immunol.*, 2008, 9: 551-557; Hoeffel, G. et al. *Immunity*, 2007, 27:481-492; Lui, G. et al., *PLoS One*, 2009, 4: e7111), but cross-presentation of tumour-associated antigens (TAAs) has not yet been described. The inventors wondered whether human pDCs exposed to MV-infected tumour cells would be able to cross-present a human TAA spontaneously expressed by tumour cells. They showed by RT-PCR that the HLA-A*0201$^{neg}$ M18 melanoma cell line expressed the cancer testis antigen, NYESO-1, whereas the A549 lung adenocarcinoma cell line did not (FIG. 17A).

Figure 17B:
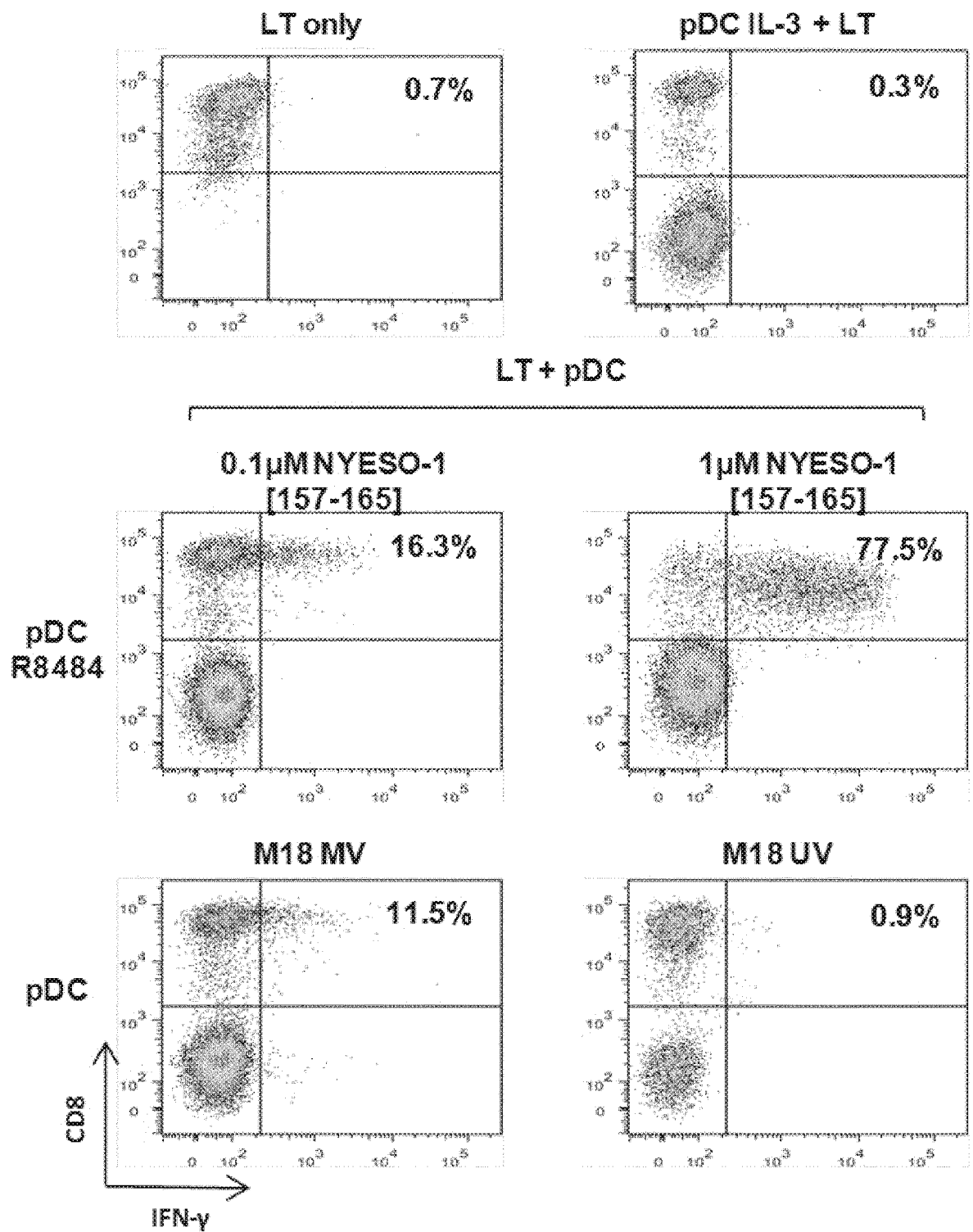
Figure 17C:
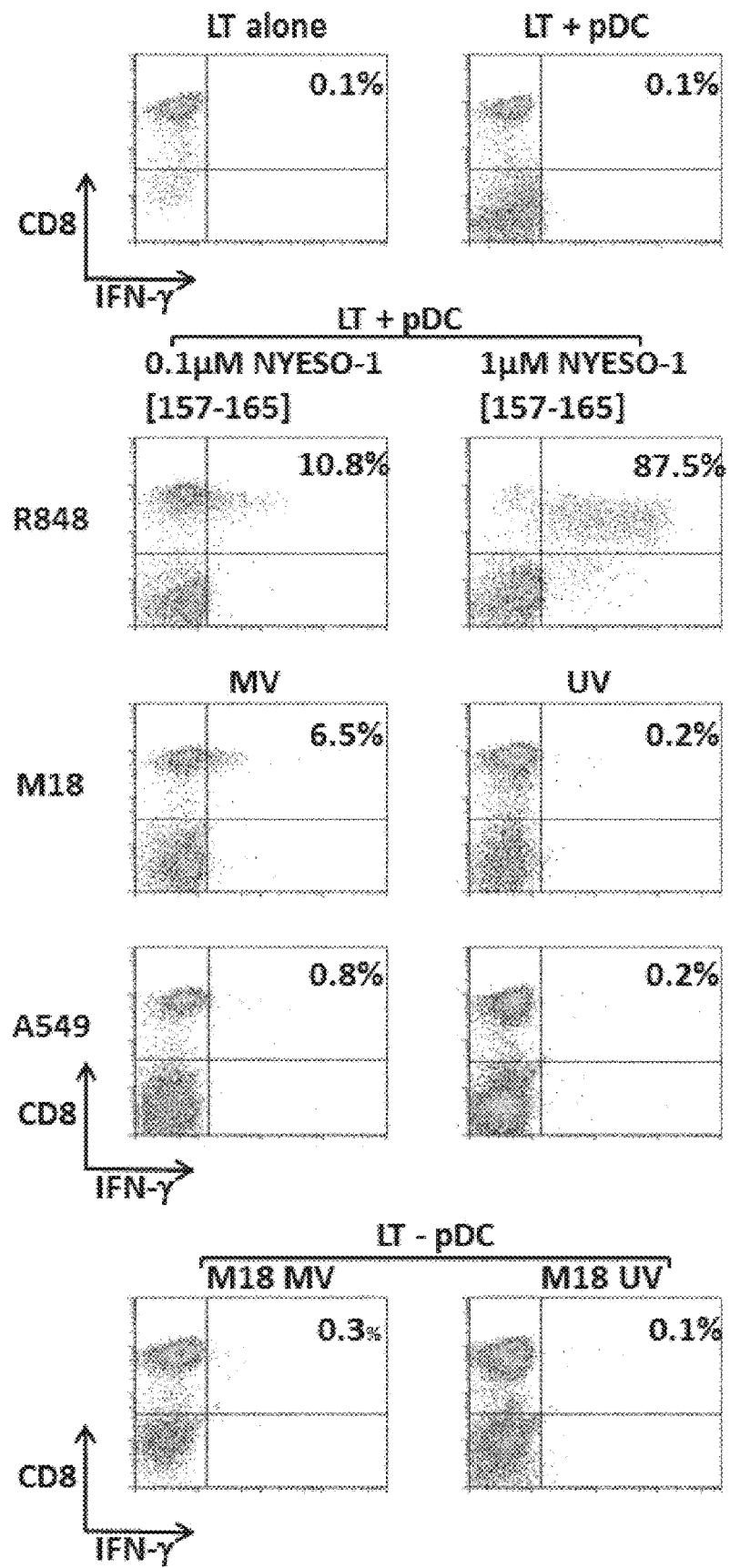
Figure 17D:
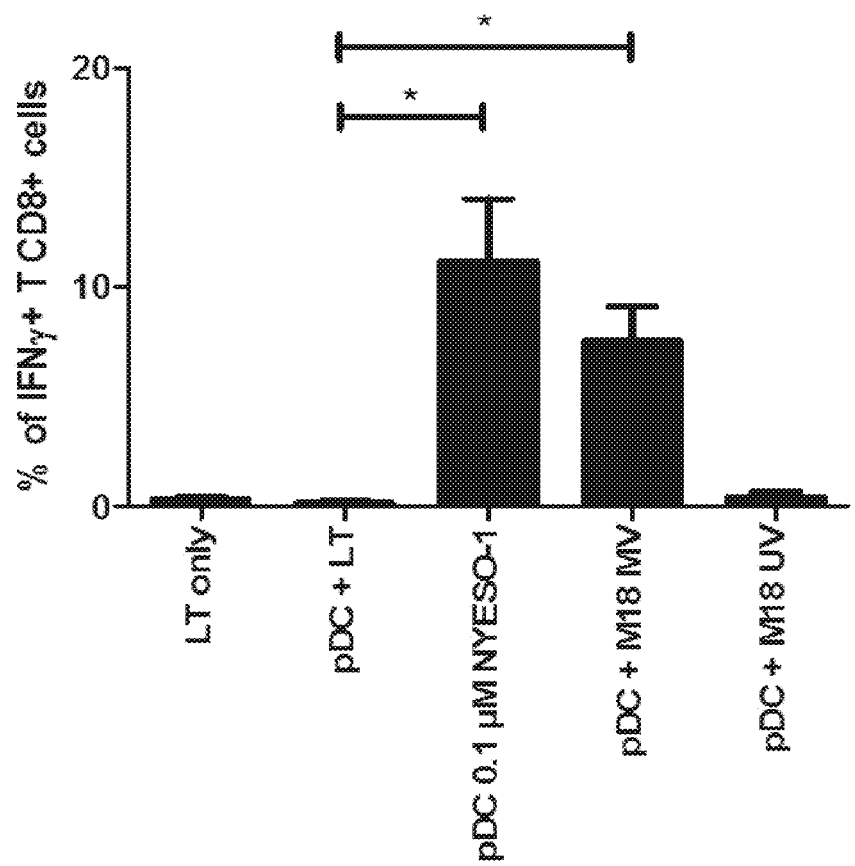

To determine whether HLA-A*0201$^{pos}$ pDCs were able to cross-present this TAA after exposure to an MV-infected or UV-irradiated HLA-A*0201$^{neg}$/NYESO-1$^{pos}$ M18 tumour cell line, the CD8+ T cell clone, M117.167, which is specific for HLA-A*0201/NYESO-1(157-165) complexes was used (FIGS. 17B-D). A schematic of this experiment is shown in FIG. 18. The M117.167 T cell clone did not produce IFN-γ, alone or in the presence of IL-3 pDCs, but was activated in the presence of pDCs pulsed with NYESO-1 [157-161] peptides (FIG. 17B). The clone was activated as soon as 0.1 µM peptide was loaded onto pDCs (16.3% IFN-γ+ cells) and was more intensely activated by pDCs pulsed with 1 µM peptide (77.5%). In the presence of pDCs cultured with MV-infected M18 tumour cells, 11.5% of the clone population was activated, whereas the clone did not produce IFN-γ in response to pDCs cultured with UV-irradiated M18 tumour cells (FIG. 17B). In response to pDCs co-cultured with MV-infected M18, the clone had an IFN-γ production profile comparable with that observed in response to pDCs pulsed with 0.1 µM NYESO-1(157-165) peptide.

As a control, the inventors failed to detect activation of the MI 17.167 T cell clone in response to MV-infected or UV-irradiated M18 tumour cells alone (FIG. 17C). This result was expected, as the M18 tumour cell line was HLA-A*0201$^{neg}$, thus unabled to directly present NYESO-1(157-165) peptide to the clone. This demonstrates that IFN-γ production by the clone in response to HLA-A*0201$^{pos}$ pDCs co-cultured with MV-infected M18 tumour cells is due to cross-presentation. The inventors also did not observe IFN-γ production in response to pDCs co-cultured with MV-infected NYESO-1$^{neg}$ A549 tumour cells. In this representative experiment, the clone produced IFN-γ in response to pDCs co-cultured with MV-infected M18 (6.5% IFN-γ$^+$ cells), a production rate close to the one observed in response to pDCs pulsed with 0.1 μM NYESO-1(157-165) peptide (10.8% IFN-γ$^+$ cells).

Altogether, these results show that pDCs are able to cross-present tumour antigen such as NYESO-1 from MV-infected tumour cells, but not from UV-irradiated ones. Thus, MV-based antitumour virotherapy should be able to hire pDCs in the antitumour immune response by activating their ability to produce high quantities of IFN-α and to cross-present TAA from MV-infected tumour cells to tumour-specific CD8+ T lymphocytes.

The inventors characterised, in vitro, the consequences of MV-based antitumour virotherapy on human pDC functions. Firstly, they showed that pDCs were not sensitive to MV infection despite expression of CD46. However, pDCs were able to detect the virus by producing IFN-α in response to high virus quantity in the absence of a survival signal, and to low virus quantity when a survival signal, such as IL-3, was added to the culture. Secondly, when the pDCs were co-cultured with MV-infected tumour cells, the pDCs underwent a maturation characterised by the induction of CD83 expression and strong production of IFN-α, with a slightly increased expression of costimulatory molecules. Conversely, the pDCs co-cultured with UV-irradiated tumour cells retained an immature phenotype similar to that observed when they were co-cultured with IL-3 alone. The inventors then identified TLR7 as the pDC receptor responsible for their activation, probably due to the presence of single-stranded viral RNA in the endocytic compartment of pDCs following internalisation of MV-infected tumour cell fragments. Finally, using an HLA-A*0201/NYESO-1(157-165)-specific CD8+ T cell clone, the inventors showed that HLA-A*0201$^+$ pDCs were able to cross-present this tumour-associated antigen (TAA) from NYESO-1$^+$ HLA-A*0201$^{neg}$ MV-infected tumour cells, but not from UV-irradiated ones. For the first time, the inventors showed the capacity of human pDCs to cross-present a TAA from dead tumour cells to CD8+ T cells. Altogether, these results suggested that MV-based antitumour virotherapy, in addition to its direct lysis of infected tumour cells, was able to recruit pDCs in the antitumour immune response, to activate their ability to produce high levels of type-I IFN and to cross-present TAA.

Firstly, the inventors showed that human pDCs exposed in vitro to MV at an MOI=1 did not undergo maturation without IL-3. In this condition, with no survival signal, pDCs underwent apoptosis and failed to acquire MV in the endosomal compartment to engage in a maturation process by the ligation of viral ssRNA to TLR7. When pDCs were exposed to MV in the presence of IL-3, they survived and maturation was observed (low IFN-α production and induction of CD83 expression). The inventors observed the activation of pDCs by MV in the absence of IL-3, only when they used a high quantity of MV (MOI=50). At this high MV concentration, the inventors thought that enough MV reached the endocytic compartment of pDCs to provide a survival/maturation signal, before their apoptosis program was engaged. Thus, when pDCs were exposed to MV in the presence of IL-3, the pDCs survived and MV was internalised and allowed triggering of TLR7 by the viral ssRNA. When pDCs were exposed to MV in the absence of IL-3, they underwent apoptosis unless enough MV reached the endocytic compartment to activate and mature them. These results explained the contradictory reports in the literature, due to differences in experimental settings. Indeed, the inventors obtained similar results to Schlender et al. who reported that a low quantity of MV Schwarz failed to induce IFN-α by pDCs cultured in the absence of IL-3 (Schlender, J. et al., *J Virol.*, 2005, 79:5507-5515), and to Duhen et al. who claimed that MV Schwarz induced high quantities of IFN-α production by pDCs in the presence of IL-3 (Duhen et al., *Virus Res.*, 2010, 152:115-125). However, the inventors did not observe that MV Schwarz inhibited IFN-α production by pDCs (31), as pDCs produced IFN-α in the presence of IL-3. Finally, both groups described staining of pDCs by a monoclonal antibody to MV hemagglutinin (H), but interpreted the result differently. One group claimed that pDCs were infected and amplified the virus (Schlender, J. et al., *J Virol.*, 2005, 79:5507-5515), while the other group concluded that, despite the H protein staining on pDCs, MV replication was low (Duhen et al., *Virus Res.*, 2010, 152: 115-125). The results of the present invention support this latter conclusion, as the inventors did not observe productive infection using MV-eGFP, even at high MOI, in the absence nor presence of IL-3.

The inventors also showed that, in the presence of MV or MV-infected tumour cells, pDCs underwent maturation characterised by the upregulation of CD83 molecule expression at the cell surface. In the presence of MV or MV-infected tumour cells, the pDCs produced higher quantities of IFN-α in response to high viral load than pDCs stimulated with R848 alone. However, these cells did not express as much of the CD40 and CD86 costimulatory molecules. Thus, this maturation phenotype resembled the maturation phenotype induced by HIV infection (Fonteneau, J. F. et al., *J Virol.*, 2004, 78:5223-5232; O'Brien, M. et al., *J Clin Invest.*, 2011, 121:1088-1101), which activated pDCs by the TLR7, as did MV (Beignon, A. S. et al., *J Clin Invest.*, 2005, 115:3265-3275). Indeed, it was now clear that, depending on the nature of the TLR agonist used, two main pathways of activation could be triggered in human pDCs. This dichotomy was first reported by Kerkmann et al., who showed that two TLR9 agonists, CpG-A and CpG-B, activated pDC maturation using two different pathways (Kerkmann, M. et al., *J Immunol.* 2003, 170:4465-4474). More recently, the same dichotomy was observed for TLR7 agonists (O'Brien, M. et al., *J Clin Invest.*, 2011, 121:1088-1101). Indeed, HIV behaved like CpG-A by triggering TLR7 and the IRF7 signaling pathway in the early endosome of pDCs, and by inducing strong production of IFN-α. The inventors showed that the maturation induced by MV+IL-3 or MV-infected cells was similar to the activation induced by HIV, suggesting an early endosomal triggering of TLR7 by MV ssRNA. This early endosome activation pathway was compatible with antigen cross-presentation expressed by virus-infected cells, as cross-presentation of viral antigens from infected cells has been demonstrated (Hoeffel, G. et al., *Immunity,* 2007, 27:481-492) and cross-presentation of the TAA from MV-infected cells, as described herein. Conversely, Schnurr et al. reported that, in vitro, pDCs, on the contrary to myeloid DCs, were not able to cross-present a TAA from a full-length protein alone or as an immune complex form (Schnurr, M. et al., *Blood*, 2005, 105:2465-2472). However, these authors used a soluble protein and did not use NYESO-1-expressing tumour cells as the antigen source. In vivo, antigen cross-presentation by pDCs was also controversial. Salio et al. reported that murine pDCs stimulated by CpG were not able to cross-present antigens, whereas they could mount a T cell response against endogenous antigens (Salio, M. et al., *J Exp Med.*, 2004, 199:567-579). Mouries et al. showed, in vivo and in vitro, also in a murine model, that soluble OVA protein and TLR agonists (CpG or R848) activated pDCs to cross-prime OVA to specific CD8+ T cells (Mouries, J. et al., *Blood*, 2008, 112:3713-3722). Similarly, presentation and cross-presentation of soluble OVA peptide or whole protein, following TLR9 stimulation by CpG or by infection with influenza virus containing OVA epitopes, was confirmed recently, in vitro, by Kool et al. (Kool et al., *J Leukoc Biol.*, 2011, 90:1177-1190). Finally, Liu et al. reported that intratumoral injection of CpG-A-stimulated pDCs to mice bearing B16 melanoma induced a tumour antigen cross-priming, but this cross-priming was performed by CD11c+ DCs, not by pDCs (Liu et al., *J Clin Invest.*, 2008, 118:1165-1175). The inventors have shown that, in vitro, human pDCs exposed to MV-infected tumour cells were able to cross-present NYESO-1 to a CD8+ T cell clone specific for this TAA. The inventors demonstrated that MV-infected tumour cells underwent cell death and were then phagocytosed by pDCs. These MV-infected cells were capable of activating pDCs without the addition of adjuvants or TLR agonists. The efficiency of MV-based antitumour virotherapy has been demonstrated in vivo in different models of human tumour xenografts in immunodeficient mice (Peng, K. W. et al., *Cancer Res.*, 2002, 62:4656-4662; McDonald, C. J. et al., *Breast Cancer Res Treat.*, 2006, 99:177-184; Blechacz, B. et al., *Hepatology*, 2006, 44:1465-1477). The first clinical trials of MV-based virotherapy have shown encouraging results (Heinzerling, L. et al., *Blood*, 2005, 106:2287-2294; Galanis, E. et al., *Cancer Res.*, 2010, 70:875-882). The efficiency of MV-based virotherapy is likely due to the lysis of tumour cells by the virus. However, a part of its efficiency may also be due to the capacity of MV-infected tumour cells to activate cells of the immune system, notably pDCs. Indeed, activation of pDCs by TLR agonist in tumour-bearing mice has been shown to induce an antitumour immune response and tumour regression (Drobits, B; et al., *J Clin Invest.*, 2012, 122:575-585; Liu, C. et al., *J Clin Invest.*, 2008, 118:1165-1175; Palamara, F. et al., *J Immunol.*, 2004, 173: 3051-3061). Liu et al. showed that murine pDCs stimulated by a TLR9 agonist induced NK cell activation and recruitment to the tumour, triggering tumour antigen cross-presentation by CD11c+ DCs (Liu, C. et al., *J Clin Invest.*, 2008, 118:1165-1175). Drobits et al. showed that topical treatment of melanoma tumours in mice with the TLR7 agonist, imiquimod, induced activation and recruitment of pDCs into the tumour and caused tumour regression (Drobits, B; et al., *J Clin Invest.*, 2012, 122:575-585). Drobits et al. demonstrated that pDCs acquired a cytotoxic activity against tumour cells by secreting TRAIL and granzyme B, in an IFNAR1-dependent mechanism. IFN-α secretion by pDCs not only induced an antitumour cytotoxic activity on pDCs by an autocrine loop, but could also act directly on tumour cells to induce apoptosis (Thyrell, L. et al., *Oncogene*, 2002, 21:1251-1262). Type-I IFN also played a role in the NK activation and was required in a mouse model of NK-cell-dependent tumor rejection (Swann, J. B. et al., *J Immunol.*, 2007, 178:7540-7549). Finally, these NK cells probably also participated in the initiation of the antitumour response by stimulating myeloid DCs, since in IFNAR1- and STAT1-deficient mice the antitumour T cell response failed to develop (Diamond, M. S. et al., *J Exp Med.*, 2011, 208: 1989-2003; Fuentes, M. B. et al., *J Exp Med.*, 2011, 208: 2005-2016). Thus, the inventors showed that MV-infected tumour cells induced a high quantity of IFN-α by pDCs, which might be favorable for the development of multicell subsets involved in an antitumour immune response. Furthermore, other oncolytic viruses known to activate pDCs are used in clinical trials of antitumour virotherapy, such as vaccinia (Kim, J. H. et al., *Mol Ther.*, 2006, 14:361-370), Herpes Simplex Virus (Kaufman, H. L. et al., *Future Oncol.*, 2010, 6:941-949) and adenovirus (Ramesh, N. et al., *Clin Cancer Res.*, 2006, 12:305-313). Tumour cells infected by these viruses may also be able to induce IFN-α production and tumour antigen cross-presentation by pDCs.

MV-based antitumour virotherapy is a promising approach for treating cancer through the oncolytic activity of the virus. Furthermore, the inventors showed that MV-infected tumour cells activated the maturation and tumour antigen cross-presentation capacities of human pDCs. Thus, MV-based antitumour virotherapy may represent an interesting approach to the recruitment of pDCs in the antitumour immune response.

Example 13

Comparative Studies Between Unmodified MV and MV-DeltaC Using Different Melanoma Cell Lines Material and Methods Cell Culture.

Tested tumour cell lines were cell lines derived from melanoma: M6, M17, M117, M88 and M113. The cells were cultured in RPMI 1640 medium supplemented with 10% fetal calf serum (FCS), 1% L-glutamine and 1% penicillin G/streptomycin. The cells were cultured at an initial concentration of $3 \cdot 10^6$ cells in 75 cm² flasks and were maintained at 37° C. in 5% $CO_2$. The cells were routinely tested and found negative for *Mycoplasma* infection.

Infection of Tumour Cells.

The cells were seeded 24 hours before infection in 12-well plates as a result of $200 \cdot 10^3$ cells per well in 1 ml of 10% FCS RPMI medium in order to allow them to adhere. Two viruses were used to infect tumour cells: (I) MV-eGFP: a recombinant live-attenuated measles virus (MV Schwarz) containing the gene encoding the fluorescent protein GFP for investigating infection of tumour cells; (II) MV-deltaC-eGFP: a recombinant modified vaccine strain of MV containing the gene encoding GFP.

The efficiency of infection was different for the two viruses unmodified MV versus MV-deltaC and between different melanoma cell lines. The inventors observed that MV-deltaC was capable of infecting tumour cells more efficiently than unmodified MV at 24 h post infection (FIGS. 19 and 20).

In addition, it was shown that tumour cells expressed more "danger signals" such as HSP 70 and CRT to the membrane following infection by MV-deltaC compared to unmodified MV (FIG. 21). This suggested a greater efficiency to induce immune responses, via the maturation and activation of dendritic cells after they phagocyte the apoptotic cells.

In vivo injection of MV-deltaC vaccines inside the melanoma tumours evidenced the enhanced effect of MV-deltaC to induce a quick response compared to a control (FIG. 22).

In conclusion, the MV-deltaC vaccine strain displayed interesting and better pro-apoptotic properties compared to conventional unmodified MV vaccine strain.

Example 14

Comparison of Cell Death Induction in Cancer and Non-Cancer Cells by Unmodified MV and MV-DeltaC To evaluate whether the stronger cell death induction by MV-deltaC relative to unmodified MV was specific to cancer cells, the inventors compared their activity on human cancer cell lines (A549 human lung adenocarcinoma and Hela cervical cancer) and on immortalized cells non-originating from cancers (HEK 293 human embryonic kidney cells and Vero African Green monkey kidney cells). A549 and Hela are commonly used prototype human cancer cells. On the contrary, as experimentally transformed with Ad5, HEK 293 cells are not cancer cells. The Vero cell lineage is continuous and aneuploid, i.e. can be replicated through many cycles of division and not become senescent.

Cells (40 000 per well in 96-well plates) were cultured together with MV-deltaC or unmodified MV viruses at different MOI (0.1, 1, 5, 10). Infections were performed on non-adherent cells in DMEM (0.2 ml). After 0, 24, 46 and 68 hours of culture, the number of living cells was determined using CellTiter-GLO reagent (Promega). This luciferase-based assay evaluated by ATP quantification the number of metabolically active cells in culture wells.

This analysis confirmed that MV-deltaC induced a much higher and earlier cell death than unmodified MV on both A549 and Hela human cancer cells, even at low MOI (FIG. 23A). Thus, the better oncolytic capacity of MV-deltaC extended from mesothelioma, melanoma and lung to cervical cancer cells. On the contrary, no difference was observed between the two viruses in cell death induction on Vero cells, and no cell death was observed on HEK 293 cells after 68 hours of infection (FIG. 23B). This suggested that the mechanism by which MV-deltaC accelerated cell death as compared to unmodified MV, or reactivated senescence pathways, was specific to human cancer cells. The observation that Vero cells were not more sensitive to MV-deltaC than to unmodified MV was crucial because MV is commonly manufactured on this cell line.

Viral growth kinetics of both viruses was evaluated simultaneously on the same cell lines (FIG. 24). Vero, HEK293, Hela and A549 cells were infected at MOI 1 with unmodified MV or MV-deltaC in 35 mm culture wells. Viral titers were determined as TCID50 at different time points after infection. A high rate of replication was observed for both viruses in Vero and HEK293 non-cancer cells. On the contrary, replication titers were lower in Hela and A549 cancer cells and MV-deltaC replicated at very low level in A549 cells. This indicated that cell death induction in cancer cells resulted in a lower production of viral progeny, which was a safety advantage for an oncolytic virus.

The invention claimed is:

1. A method for preparing vaccinal plasmacytoid dendritic cells (pDCs), comprising:
   a. providing malignant tumor or cancer cells collected from a patient;
   b. in vitro infecting the malignant tumor or cancer cells with an infectious live attenuated MV strain to yield a cell lysate, wherein the gene encoding the viral accessory C protein has been knocked out in the infectious live-attenuated MV (MV-deltaC); and
   c. contacting pDCs with the cell lysate of b. to yield vaccinal pDCs.

2. The method of claim 1, wherein the pDCs are provided by leukapheresis.

3. The method of claim 1, wherein the malignant tumor or cancer is selected from aggressive malignant tumor, aggressive cancer, malignant mesothelioma, melanoma and lung adenocarcinoma.

4. The method of to claim 1, wherein the live-attenuated MV strain is the Schwarz strain or the Moraten strain.

5. A method of inducing cell death of malignant cancer cells in a subject in need thereof, comprising:
   (A) providing vaccinal pDCs prepared by the method of claim 1; and
   (B) administering the pDCs to the subject.

6. The method of claim 5, wherein the malignant cancer cells are selected from the group consisting of malignant mesothelioma cells, melanoma cells and lung adenocarcinoma cells.

7. A pharmaceutical composition for treating an aggressive malignant tumor or aggressive cancer, comprising:

(A) an infectious live-attenuated MV strain in which the gene encoding the viral accessory C protein has been knocked out (MV-deltaC); and
   (B) a pharmaceutically acceptable vehicle.

8. An assembly of active ingredients for treating an aggressive malignant tumor or aggressive cancer, comprising
   (i) an infectious live-attenuated MV strain in which the gene encoding the viral accessory C protein has been knocked out (MV-deltaC),
   (ii) a chemotherapeutic agent, and
   (iii) a pharmaceutically acceptable vehicle.

9. The assembly of active ingredients of claim 8, further comprising vaccinal pDCs prepared by a method comprising:
   a. providing malignant tumor or cancer cells collected from a patient;
   b. in vitro infecting the malignant tumor or cancer cells with an infectious live attenuated MV strain to yield a cell lysate, wherein the gene encoding the viral accessory C protein has been knocked out in the infectious live-attenuated MV (MV-deltaC); and
   c. contacting pDCs with the cell lysate of b. to yield vaccinal pDCs.

10. An assembly of active ingredients for treating an aggressive malignant tumor or aggressive cancer, comprising:
   (i) an infectious live-attenuated MV strain in which the gene encoding the viral accessory C protein has been knocked out (MV-deltaC), and
   (ii) vaccinal pDCs prepared by the method of claim 1.

* * * * *

SEQUENCE LISTING

```
<160> NUMBER OF SEQ ID NOS: 5

<210> SEQ ID NO 1
<211> LENGTH: 19843
<212> TYPE: DNA
<213> ORGANISM: Artificial Sequence
<220> FEATURE:
<223> OTHER INFORMATION: pTM-MVSchw-deltaC-ATU1 (eGFP)
<220> FEATURE:
<221> NAME/KEY: mutation
<222> LOCATION: (2788)..(2788)
<223> OTHER INFORMATION: The T nucleotide of native MVSchw genome cDNA
      is replaced by a C nucleotide

<400> SEQUENCE: 1
gcggccgcta atacgactca ctatagggcc aactttgttt ggtctgatga gtccgtgagg      60
acgaaacccg gagtcccggg tcaccaaaca aagttgggta aggatagttc aatcaatgat     120
catcttctag tgcacttagg attcaagatc ctattatcag ggacaagagc aggattaggg     180
atatccgaga cgcgtacgat ggtgagcaag ggcgaggagc tgttcaccgg ggtggtgccc     240
atcctggtcg agctggacgg cgacgtaaac ggccacaagt tcagcgtgtc cggcgagggc     300
gagggcgatg ccacctacgg caagctgacc ctgaagttca tctgcaccac cggcaagctg     360
cccgtgccct ggcccaccct cgtgaccacc ctgacctacg gcgtgcagtg cttcagccgc     420
taccccgacc acatgaagca gcacgacttc ttcaagtccg ccatgcccga aggctacgtc     480
caggagcgca ccatcttctt caaggacgac ggcaactaca agacccgcgc cgaggtgaag     540
ttcgagggcg acacccgtggt gaaccgcatc gagctgaagg gcatcgactt caaggaggac     600
ggcaacatcc tggggcacaa gctggagtac aactacaaca gccacaacgt ctatatcatg     660
gccgacaagc agaagaacgg catcaaggtg aacttcaaga tccgccacaa catcgaggac     720
ggcagcgtgc agctcgccga ccactaccag cagaacaccc ccatcggcga cggccccgtg     780
```

```
ctgctgcccg acaaccacta cctgagcacc cagtccgccc tgagcaaaga ccccaacgag    840
aagcgcgatc acatggtcct gctggagttc gtgaccgccg ccgggatcac tctcggcatg    900
gacgagctgt acaagtaggc gcgcagcgct tagacgtctc gcgatcgatt agtgcgagag    960
gccgagggcc agaacaacat ccgcctacca tccatcattg ttataaaaaa cttaggattc   1020
aagatcctat tatcagggac aagagcagga ttagggatat ccgagatggc cacactttta   1080
aggagcttag cattgttcaa aagaaacaag gacaaaccac ccattacatc aggatccggt   1140
ggagccatca gaggaatcaa acacattatt atagtaccaa tccctggaga ttcctcaatt   1200
accactcgat ccagacttct ggaccggttg gtgaggttaa ttggaaaccc ggatgtgagc   1260
gggcccaaac taacaggggc actaataggt atattatcct tatttgtgga gtctccaggt   1320
caattgattc agaggatcac cgatgaccct gacgttagca taaggctgtt agaggttgtc   1380
cagagtgacc agtcacaatc tggccttacc ttcgcatcaa gaggtaccaa catggaggat   1440
gaggcggacc aatacttttc acatgatgat ccaattagta gtgatcaatc caggttcgga   1500
tggttcggga acaaggaaat ctcagatatt gaagtgcaag accctgaggg attcaacatg   1560
attctgggta ccatcctagc ccaaatttgg gtcttgctcg caaaggcggt tacggcccca   1620
gacacggcag ctgattcgga gctaagaagg tggataaagt acacccaaca agaagggta    1680 gttggtgaat ttagattgga gagaaaatgg ttggatgtgg tgaggaacag gattgccgag   1740
gacctctcct tacgccgatt catggtcgct ctaatcctgg atatcaagag aacacccgga   1800
aacaaaccca ggattgctga atgatatgt gacattgata catatatcgt agaggcagga    1860
ttagccagtt ttatcctgac tattaagttt gggatagaaa ctatgtatcc tgctcttgga   1920
ctgcatgaat ttgctggtga gttatccaca cttgagtcct tgatgaacct ttaccagcaa   1980
atgggggaaa ctgcacccta catggtaatc ctggagaact caattcagaa caagttcagt   2040
gcaggatcat accctctgct ctggagctat gccatgggag taggagtgga acttgaaaac   2100
tccatgggag gtttgaactt tggccgatct tactttgatc cagcatattt tagattaggg   2160
caagagatgg taaggaggtc agctggaaag gtcagttcca cattggcatc tgaactcggt   2220
atcactgccg aggatgcaag gcttgtttca gagattgcaa tgcatactac tgaggacaag   2280
atcagtagag cggttggacc cagacaagcc caagtatcat ttctacacgg tgatcaaagt   2340
gagaatgagc taccgagatt gggggggcaag gaagatagga gggtcaaaca gagtcgagga   2400
gaagccaggg agagctacag agaaaccggg cccagcagag caagtgatgc gagagctgcc   2460
catcttccaa ccggcacacc cctagacatt gacactgcaa cggagtccag ccaagatccg   2520
caggacagtc gaaggtcagc tgacgccctg cttaggctgc aagccatggc aggaatctcg   2580
gaagaacaag gctcagacac ggacacccct atagtgtaca atgacagaaa tcttctagac   2640
taggtgcgag aggccgaggg ccagaacaac atccgcctac catccatcat tgttataaaa   2700
aacttaggaa ccaggtccac acagccgcca gcccatcaac catccactcc cacgattgga   2760
gccaatggca gaagcaggc acgccacgt caaaaacgga ctggaatgca tccgggctct    2820
caaggccgag cccatcggct cactggccat cgaggaagct atggcagcat ggtcagaaat   2880
atcagacaac caggacagg agcgagccac ctgcagggaa gagaaggcag gcagttcggg    2940
tctcagcaaa ccatgcctct cagcaattgg atcaactgaa ggcggtgcac ctcgcatccg   3000
cggtcaggga cctggagaga gcgatgacga cgctgaaact ttgggaatcc ccccaagaaa   3060
tctccaggca tcaagcactg ggttacagtg ttattacgtt tatgatcaca gcggtgaagc   3120
ggttaaggga atccaagatg ctgactctat catggttcaa tcaggccttg atggtgatag   3180
```

```
caccctctca ggaggagaca atgaatctga aaacagcgat gtggatattg gcgaacctga   3240
taccgaggga tatgctatca ctgaccgggga atctgctccc atctctatgg ggttcagggc   3300
ttctgatgtt gaaactgcag aaggagggga gatccacgag ctcctgagac tccaatccag   3360
aggcaacaac tttccgaagc ttgggaaaac tctcaatgtt cctccgcccc cggacccgg    3420 tagggccagc acttccggga cacccattaa aaagggcaca gacgcgagat tagcctcatt   3480
tggaacggag atcgcgtctt tattgacagg tggtgcaacc caatgtgctc gaaagtcacc   3540
ctcggaacca tcagggccag gtgcacctgc ggggaatgtc ccgagtgtg tgagcaatgc    3600 cgcactgata caggagtgga cacccgaatc tggtaccaca atctccccga gatcccagaa   3660
taatgaagaa gggggagact attatgatga tgagctgttc tctgatgtcc aagatattaa   3720
aacagccttg gccaaaatac acgaggataa tcagaagata atctccaagc tagaatcact   3780
gctgttattg aagggagaag ttgagtcaat taagaagcag atcaacaggc aaaatatcag   3840
catatccacc ctggaaggac acctctcaag catcatgatc gccattcctg acttgggaa    3900 ggatcccaac gaccccactg cagatgtcga aatcaatccc gacttgaaac ccatcatagg   3960
cagagattca ggccgagcac tggccgaagt tctcaagaaa cccgttgcca gccgacaact   4020
ccaaggaatg acaaatggac ggaccagttc cagaggacag ctgctgaagg aatttcagct   4080
aaagccgatc gggaaaaaga tgagctcagc cgtcgggttt gttcctgaca ccggccctgc   4140
atcacgcagt gtaatccgct ccattataaa atccagccgg ctagaggagg atcggaagcg   4200
ttacctgatg actctccttg atgatatcaa aggagccaat gatcttgcca agttccacca   4260
gatgctgatg aagataataa tgaagtagct acagctcaac ttacctgcca accccatgcc   4320
agtcgaccca actagtacaa cctaaatcca ttataaaaaa cttaggagca aagtgattgc   4380
ctcccaaggt ccacaatgac agagacctac gacttcgaca agtcggcatg ggacatcaaa   4440
gggtcgatcg ctccgataca acccaccacc tacagtgatg gcaggctggt gccccaggtc   4500
agagtcatag atcctggtct aggcgacagg aaggatgaat gctttatgta catgtttctg   4560
ctgggggttg ttgaggacag cgattcccta gggcctccaa tcgggcgagc atttgggttc   4620
ctgcccttag gtgttggcag atccacagca aagcccgaaa aactcctcaa agaggccact   4680
gagcttgaca tagttgttag acgtacagca gggctcaatg aaaaactggt gttctacaac   4740
aacaccccac taactctcct cacaccttgg agaaaggtcc taacaacagg gagtgtcttc   4800
aacgcaaacc aagtgtgcaa tgcggttaat ctgataccgc tcgataccc gcagaggttc    4860 cgtgttgttt atatgagcat cacccgtctt tcggataacg ggtattacac cgttcctaga   4920
agaatgctgg aattcagatc ggtcaatgca gtggccttca acctgctggt gacccttagg   4980
attgacaagc gataggccc tgggaagatc atcgacaata cagagcaact tcctgaggca    5040
acatttatgg tccacatcgg gaacttcagg agaaagaaga gtgaagtcta ctctgccgat   5100
tattgcaaaa tgaaaatcga aaagatgggc ctggttttg cacttggtgg gatagggggc    5160
accagtcttc acattagaag cacaggcaaa atgagcaaga ctctccatgc acaactcggg   5220
ttcaagaaga ccttatgtta cccgctgatg gatatcaatg aagaccttaa tcgattactc   5280
tggaggagca gatgcaagat agtaagaatc caggcagttt tgcagccatc agttcctcaa   5340
gaattccgca tttacgacga cgtgatcata aatgatgacc aaggactatt caaagttctg   5400
tagaccgtag tgcccagcaa tgcccgaaaa cgacccccct cacaatgaca gccagaaggc   5460
ccggacaaaa aagcccccctc cgaaagactc cacggaccaa gcgagaggcc agccagcagc   5520
```

```
cgacggcaag cgcgaacacc aggcggcccc agcacagaac agccctgaca caaggccacc      5580
accagccacc ccaatctgca tcctcctcgt gggaccccg aggaccaacc cccaaggctg       5640
cccccgatcc aaaccaccaa ccgcatcccc accaccccg ggaaagaaac ccccagcaat       5700
tggaaggccc ctccccctct tcctcaacac aagaactcca caaccgaacc gcacaagcga      5760
ccgaggtgac ccaaccgcag gcatccgact ccctagacag atcctctctc cccggcaaac     5820
taaacaaaac ttagggccaa ggaacataca cacccaacag aacccagacc ccggcccacg     5880
gcgccgcgcc cccaacccc gacaaccaga gggagcccc aaccaatccc gccggctccc       5940
ccggtgccca caggcaggga caccaacccc cgaacagacc cagcacccaa ccatcgacaa     6000
tccaagacgg gggggccccc ccaaaaaaag gccccaggg gccgacagcc agcaccgcga     6060
ggaagcccac ccaccccaca cacgaccacg gcaaccaaac cagaacccag accaccctgg    6120
gccaccagct cccagactcg gccatcaccc cgcagaaagg aaaggccaca acccgcgcac    6180
cccagccccg atccggcggg gagccaccca acccgaacca gcaccaagag gcgatccccg    6240 aaggacccc gaaccgcaaa ggacatcagt atcccacagc ctctccaagt cccccggtct     6300
cctcctcttc tcgaagggac caaaagatca atccaccaca cccgacgaca ctcaactccc    6360 caccccctaaa ggagacaccg ggaatcccag aatcaagact catccaatgt ccatcatggg  6420
tctcaaggtg aacgtctctg ccatattcat ggcagtactg ttaactctcc aaacacccac    6480
cggtcaaatc cattgggca atctctctaa gataggggtg gtaggaatag gaagtgcaag    6540
ctacaaagtt atgactcgtt ccagccatca atcattagtc ataaaattaa tgcccaatat    6600
aactctcctc aataactgca cgagggtaga gattgcagaa tacaggagac tactgagaac   6660
agttttggaa ccaattagag atgcacttaa tgcaatgacc cagaatataa gaccggttca    6720
gagtgtagct tcaagtagga gacacaagag atttgcggga gtagtcctgg caggtgcggc    6780
cctaggcgtt gccacagctg ctcagataac agccggcatt gcacttcacc agtccatgct   6840
gaactctcaa gccatcgaca atctgagagc gagcctggaa actactaatc aggcaattga   6900
gacaatcaga caagcagggc aggagatgat attggctgtt caggggtgtcc aagactacat  6960 caataatgag ctgataccgt ctatgaacca actatcttgt gatttaatcg gccagaagct    7020
cgggctcaaa ttgctcagat actatacaga aatcctgtca ttatttggcc ccagtttacg   7080
ggaccccata tctgcggaga tatctatcca ggctttgagc tatgcgcttg gaggagacat    7140
caataaggtg ttagaaaagc tcggatacag tggaggtgat ttactgggca tcttagagag    7200
cggaggaata aaggcccgga taactcacgt cgacacagag tcctacttca ttgtcctcag   7260
tatagcctat ccgacgctgt ccgagattaa gggggtgatt gtccaccggc tagaggggt    7320 ctcgtacaac ataggctctc aagagtggta taccactgtg cccaagtatg ttgcaaccca   7380
agggtacctt atctcgaatt ttgatgagtc atcgtgtact ttcatgccag aggggactgt    7440
gtgcagccaa aatgccttgt acccgatgag tcctctgctc caagaatgcc tccggggta    7500 caccaagtcc tgtgctcgta cactcgtatc cgggtctttt gggaaccggt tcattttatc    7560
acaagggaac ctaatagcca attgtgcatc aatcctttgc aagtgttaca caacaggaac    7620
gatcattaat caagaccctg caagatcct aacatacatt gctgccgatc actgcccggt   7680
agtcgaggtg aacggcgtga ccatccaagt cgggagcagg aggtatccag acgctgtgta   7740
cttgcacaga attgacctcg gtcctcccat atcattggag aggttggacg tagggacaaa    7800
tctggggaat gcaattgcta agttggagga tgccaaggaa ttgttggagt catcggacca  7860
gatattgagg agtatgaaag gtttatcgag cactagcata gtctacatcc tgattgcagt   7920
```

```
gtgtcttgga gggttgatag ggatccccgc tttaatatgt tgctgcaggg ggcgttgtaa   7980
caaaaaggga gaacaagttg gtatgtcaag accaggccta agcctgatc ttacgggaac   8040 atcaaaatcc tatgtaaggt cgctctgatc ctctacaact cttgaaacac aaatgtccca   8100
caagtctcct cttcgtcatc aagcaaccac cgcacccagc atcaagccca cctgaaatta   8160
tctccggctt ccctctggcc gaacaatatc ggtagttaat caaaacttag ggtgcaagat   8220
catccacaat gtcaccacaa cgagaccgga taaatgcctt ctacaaagat aaccccatc    8280 ccaagggaag taggatagtc attaacagag aacatcttat gattgataga ccttatgttt   8340
tgctggctgt tctgtttgtc atgtttctga gcttgatcgg gttgctagcc attgcaggca   8400
ttagacttca tcgggcagcc atctacaccg cagagatcca taaaagcctc agcaccaatc   8460
tagatgtaac taactcaatc gagcatcagg tcaggacgt gctgacacca ctcttcaaaa    8520
tcatcggtga tgaagtgggc ctgaggacac ctcagagatt cactgaccta gtgaaattaa   8580
tctctgacaa gattaaattc cttaatccgg atagggagta cgacttcaga gatctcactt   8640
ggtgtatcaa cccgccagag agaatcaaat tggattatga tcaatactgt gcagatgtgg   8700
ctgctgaaga gctcatgaat gcattggtga actcaactct actggagacc agaacaacca   8760
atcagttcct agctgtctca aagggaaact gctcagggcc cactacaatc agaggtcaat   8820
tctcaaacat gtcgctgtcc ctgttagact tgtatttagg tcgaggttac aatgtgtcat   8880
ctatagtcac tatgacatcc cagggaatgt atgggggaac ttacctagtg gaaaagccta   8940
atctgagcag caaaaggtca gagttgtcac aactgagcat gtaccgagtg tttgaagtag   9000
gtgttatcag aaatccgggt ttgggggctc cggtgttcca tatgacaaac tatcttgagc   9060
aaccagtcag taatgatctc agcaactgta tggtggcttt ggggagctc aaactcgcag    9120 cccttttgtca cggggaagat tctatcacaa ttccctatca gggatcaggg aaaggtgtca   9180
gcttccagct cgtcaagcta ggtgtctgga atccccaac cgacatgcaa tcctgggtcc    9240
ccttatcaac ggatgatcca gtgatagaca ggctttacct ctcatctcac agaggtgtta   9300
tcgctgacaa tcaagcaaaa tgggctgtcc cgacaacacg aacagatgac aagttgcgaa   9360
tggagacatg cttccaacag gcgtgtaagg gtaaaatcca agcactctgc gagaatcccg   9420
agtgggcacc attgaaggat aacaggattc cttcatacgg ggtcttgtct gttgatctga   9480
gtctgacagt tgagcttaaa atcaaaattg cttcgggatt cgggccattg atcacacacg   9540
gttcagggat ggacctatac aaatccaacc acaacaatgt gtattggctg actatcccgc   9600
caatgaagaa cctagcctta ggtgtaatca acacattgga gtggataccg agattcaagg   9660
ttagtcccta cctcttcact gtcccaatta aggaagcagg cgaagactgc catgccccaa   9720
catacctacc tgcggaggtg gatggtgatg tcaaactcag ttccaatctg gtgattctac   9780
ctggtcaaga tctccaatat gttttggcaa cctacgatac ttccagggtt gaacatgctg   9840
tggtttatta cgtttacagc ccaagccgct cattttctta cttttatcct tttaggttgc   9900
ctataaaggg ggtccccatc gaattacaag tggaatgctt cacatgggac caaaaactct   9960
ggtgccgtca cttctgtgtg cttgcggact cagaatctgg tggacatatc actcactctg  10020
ggatggtggg catgggagtc agctgcacag tcacccggga agatggaacc aatcgcagat  10080
agggctgcta gtgaaccaat cacatgatgt cacccagaca tcaggcatac ccactagtgt  10140
gaaatagaca tcagaattaa gaaaacgta gggtccaagt ggttcccgt tatggactcg    10200 ctatctgtca accagatctt ataccctgaa gttcacctag atagcccgat agttaccaat  10260
```

```
aagatagtag ccatcctgga gtatgctcga gtccctcacg cttacagcct ggaggaccct    10320
acactgtgtc agaacatcaa gcaccgccta aaaaacggat tttccaacca aatgattata    10380
aacaatgtgg aagttgggaa tgtcatcaag tccaagctta ggagttatcc ggcccactct    10440
catattccat atccaaattg taatcaggat ttatttaaca tagaagacaa agagtcaacg    10500
aggaagatcc gtgaactcct caaaaagggg aattcgctgt actccaaagt cagtgataag    10560
gttttccaat gcttaaggga cactaactca cggcttggcc taggctccga attgagggag    10620
gacatcaagg agaaagttat taacttggga gtttacatgc acagctccca gtggtttgag    10680 cccttctgt tttggtttac agtcaagact gagatgaggt cagtgattaa atcacaaacc    10740
catacttgcc ataggaggag acacacacct gtattcttca ctggtagttc agttgagttg    10800
ctaatctctc gtgaccttgt tgctataatc agtaaagagt ctcaacatgt atattacctg    10860
acatttgaac tggttttgat gtattgtgat gtcatagagg ggaggttaat gacagagacc    10920
gctatgacta ttgatgctag gtatacagag cttctaggaa gagtcagata catgtggaaa    10980
ctgatagatg gtttcttccc tgcactcggg aatccaactt atcaaattgt agccatgctg    11040
gagcctcttt cacttgctta cctgcagctg agggatataa cagtagaact cagaggtgct    11100
ttccttaacc actgctttac tgaaatacat gatgttcttg accaaaacgg ttttctgat    11160 gaaggtactt atcatgagtt aactgaagct ctagattaca ttttcataac tgatgacata    11220
catctgacag gggagatttt ctcattttc agaagtttcg ccacccag acttgaagca    11280 gtaacggctg ctgaaaatgt taggaaatac atgaatcagc ctaaagtcat tgtgtatgag    11340
actctgatga aaggtcatgc catatttgt ggaatcataa tcaacggcta tcgtgacagg    11400
cacggaggca gttggccacc gctgaccctc ccctgcatg ctgcagacac aatccggaat    11460
gctcaagctt caggtgaagg gttaacacat gagcagtgcg ttgataactg gaaatctttt    11520
gctggagtga aatttggctg ctttatgcct cttagcctgg atagtgatct gacaatgtac    11580
ctaaaggaca aggcacttgc tgctctccaa agggaatggg attcagttta cccgaaagag    11640
ttcctgcgtt acgaccctcc caagggaacc gggtcacgga ggcttgtaga tgttttcctt    11700
aatgattcga gctttgaccc atatgatgtg ataatgtatg ttgtaagtgg agcttacctc    11760
catgaccctg agttcaacct gtcttacagc ctgaaagaaa aggagatcaa ggaaacaggt    11820 agacttttg ctaaaatgac ttacaaaatg agggcatgcc aagtgattgc tgaaaatcta    11880
atctcaaacg ggattggcaa atattttaag gacaatggga tggccaagga tgagcacgat    11940
ttgactaagg cactccacac tctagctgtc tcaggagtcc ccaaagatct caaagaaagt    12000 cacaggggg ggccagtctt aaaaacctac tcccgaagcc cagtccacac aagtaccagg    12060
aacgtgagag cagcaaaagg gtttataggg ttccctcaag taattcggca ggaccaagac    12120
actgatcatc cggagaatat ggaagcttac gagacagtca gtgcatttat cacgactgat    12180
ctcaagaagt actgccttaa ttggagatat gagaccatca gcttgtttgc acagaggcta    12240
aatgagattt acgattgcc ctcatttttc cagtggctgc ataagaggct tgagacctct    12300
gtcctgtatg taagtgaccc tcattgcccc cccgaccttg acgcccatat cccgttatat    12360
aaagtcccca tgatcaaat cttcattaag taccctatgg gaggtataga agggtattgt    12420
cagaagctgt ggaccatcag caccattccc tatctatacc tggctgctta tgagagcgga    12480
gtaaggattg cttcgttagt gcaaggggac aatcagacca tagccgtaac aaaaagggta    12540
cccagcacat ggccctacaa ccttaagaaa cgggaagctg ctagagtaac tagagattac    12600
tttgtaattc ttaggcaaag gctacatgat attggccatc acctcaaggc aaatgagaca    12660
```

```
attgtttcat cacattttt tgtctattca aaaggaatat attatgatgg gctacttgtg   12720
tcccaatcac tcaagagcat cgcaagatgt gtattctggt cagagactat agttgatgaa   12780
acaagggcag catgcagtaa tattgctaca acaatggcta aaagcatcga gagaggttat   12840
gaccgttacc ttgcatattc cctgaacgtc ctaaaagtga tacagcaaat tctgatctct   12900
cttggcttca caatcaattc aaccatgacc cgggatgtag tcatacccct cctcacaaac   12960
aacgacctct taataaggat ggcactgttg cccgctccta ttgggggat gaattatctg   13020
aatatgagca ggctgtttgt cagaaacatc ggtgatccag taacatcatc aattgctgat   13080
ctcaagagaa tgattctcgc ctcactaatg cctgaagaga ccctccatca agtaatgaca   13140
caacaaccgg gggactcttc attcctagac tgggctagcg accctactc agcaaatctt   13200
gtatgtgtcc agagcatcac tagactcctc aagaacataa ctgcaaggtt tgtcctgatc   13260
catagtccaa acccaatgtt aaaaggatta ttccatgatg acagtaaaga agaggacgag   13320
ggactggcgg cattcctcat ggacaggcat attatagtac ctagggcagc tcatgaaatc   13380
ctggatcata gtgtcacagg ggcaagagag tctattgcag gcatgctgga taccacaaaa   13440
ggcttgattc gagccagcat gaggaagggg gggttaacct ctcgagtgat aaccagattg   13500
tccaattatg actatgaaca attcagagca gggatggtgc tattgacagg aagaaagaga   13560
aatgtcctca ttgacaaaga gtcatgttca gtgcagctgg cgagagctct aagaagccat   13620
atgtgggcga ggctagctcg aggacggcct atttacggcc ttgaggtccc tgatgtacta   13680
gaatctatgc gaggccacct tattcggcgt catgagacat gtgtcatctg cgagtgtgga   13740
tcagtcaact acggatggtt ttttgtcccc tcgggttgcc aactggatga tattgacaag   13800
gaaacatcat ccttgagagt cccatatatt ggttctacca ctgatgagag aacagacatg   13860
aagcttgcct tcgtaagagc cccaagtcga tccttgcgat ctgctgttag aatagcaaca   13920
gtgtactcat gggcttacgg tgatgatgat agctcttgga acgaagcctg gttgttggct   13980
aggcaaaggg ccaatgtgag cctggaggag ctaagggtga tcactcccat ctcaacttcg   14040
actaatttag cgcataggtt gagggatcgt agcactcaag tgaaatactc aggtacatcc   14100
cttgtccgag tggcgaggta taccacaatc tccaacgaca atctctcatt tgtcatatca   14160
gataagaagg ttgatactaa ctttatatac caacaaggaa tgcttctagg gttgggtgtt   14220
ttagaaacat tgtttcgact cgagaaagat accggatcat ctaacacggt attacatctt   14280
cacgtcgaaa cagattgttg cgtgatcccg atgatagatc atcccaggat acccagctcc   14340
cgcaagctag agctgagggc agagctatgt accaacccat tgatatatga taatgcacct   14400
ttaattgaca gagatgcaac aaggctatac acccagagcc ataggaggca ccttgtggaa   14460
tttgttacat ggtccacacc ccaactatat cacatttag ctaagtccac agcactatct   14520
atgattgacc tggtaacaaa atttgagaag gaccatatga atgaaatttc agctctcata   14580
ggggatgacg atatcaatag tttcataact gagtttctgc tcatagagcc aagattattc   14640
actatctact gggccagtg tgcggccatc aattgggcat tgatgtaca ttatcataga   14700
ccatcaggga aatatcagat gggtgagctg ttgtcatcgt tcctttctag aatgagcaaa   14760
ggagtgttta aggtgcttgt caatgctcta agccacccaa agatctacaa gaaattctgg   14820
cattgtggta ttatagagcc tatccatggt ccttcacttg atgctcaaaa cttgcacaca   14880
actgtgtgca acatggtta cacatgctat atgacctacc tcgacctgtt gttgaatgaa   14940
gagttagaag agttcacatt tctccttgtgt gaaagcgacg aggatgtagt accggacaga   15000
```

-continued

```
ttcgacaaca tccaggcaaa acacttatgt gttctggcag atttgtactg tcaaccaggg    15060
acctgcccac caattcgagg tctaagaccg gtagagaaat gtgcagttct aaccgaccat    15120
atcaaggcag aggctatgtt atctccagca ggatcttcgt ggaacataaa tccaattatt    15180
gtagaccatt actcatgctc tctgacttat ctccggcgag gatcgatcaa acagataaga    15240
ttgagagttg atccaggatt cattttcgac gccctcgctg aggtaaatgt cagtcagcca    15300
aagatcggca gcaacaacat ctcaaatatg agcatcaagg cttccagacc cccacacgat    15360
gatgttgcaa aattgctcaa agatatcaac acaagcaagc acaatcttcc catttcaggg    15420
ggcaatctcg ccaattatga aatccatgct ttccgcagaa tcggttgaa ctcatctgct     15480
tgctacaaag ctgttgagat atcaacatta attaggagat gccttgagcc agggaggac     15540
ggcttgttct tgggtgaggg atcggttct atgttgatca cttataaaga gatacttaaa     15600
ctaaacaagt gcttctataa tagtggggtt tccgccaatt ctagatctgg tcaaagggaa    15660
ttagcaccct atccctccga agttggcctt gtcgaacaca gaatgggagt aggtaatatt    15720
gtcaaagtgc tctttaacgg gaggcccgaa gtcacgtggg taggcagtgt agattgcttc    15780
aatttcatag ttagtaatat ccctacctct agtgtggggt ttatccattc agatatagag    15840
accttgcctg acaaagatac tatagagaag ctagaggaat tggcagccat cttatcgatg    15900
gctctgctcc tgggcaaaat aggatcaata ctggtgatta agcttatgcc tttcagcggg    15960
gattttgttc agggatttat aagttatgta gggtctcatt atagagaagt gaaccttgta    16020
taccctagat acagcaactt catctctact gaatcttatt tggttatgac agatctcaag    16080
gctaaccggc taatgaatcc tgaaaagatt aagcagcaga taattgaatc atctgtgagg    16140
acttcacctg gacttatagg tcacatccta tccattaagc aactaagctg catacaagca    16200
attgtgggag acgcagttag tagaggtgat atcaatccta ctctgaaaaa acttacacct    16260
atagagcagg tgctgatcaa ttgcgggttg gcaattaacg gacctaagct gtgcaaagaa    16320
ttgatccacc atgatgttgc ctcagggcaa gatggattgc ttaattctat actcatcctc    16380
tacagggagt tggcaagatt caaagacaac caaagaagtc aacaagggat gttccacgct    16440
taccccgtat tggtaagtag caggcaacga gaacttatat ctaggatcac ccgcaaattc    16500
tgggggcaca ttcttctta ctccgggaac aaaaagttga taaataagtt tatccagaat     16560
ctcaagtccg gctatctgat actagactta caccagaata tcttcgttaa gaatctatcc    16620
aagtcagaga aacagattat tatgacgggg ggtttgaaac gtgagtgggt ttttaaggta    16680
acagtcaagg agaccaaaga atggtataag ttagtcggat acagtgccct gattaaggac    16740
taattggttg aactccggaa ccctaatcct gccctaggtg gttaggcatt atttgcaata    16800
tattaaagaa aactttgaaa atacgaagtt tctattccca gctttgtctg gtggccggca    16860
tggtcccagc ctcctcgctg gcgccggctg ggcaacattc gaggggacc gtcccctcgg     16920
taatggcgaa tgggacgcgg ccgatccggc tgctaacaaa gcccgaaagg aagctgagtt    16980
ggctgctgcc accgctgagc aataactagc ataaccccctt ggggcctcta acgggtctt    17040
gaggggtttt ttgctgaaag gaggaactat atccggatgc ggccgcgggc cctatggtac    17100
ccagcttttg ttcccttag tgaggttaa ttccagctt ggcgtaatca tggtcatagc       17160
tgtttcctgt gtgaaattgt tatccgctca caattccaca caacatagga gccggaagca    17220
taaagtgtaa agcctggggt gcctaatgag tgaggtaact cacattaatt gcgttgcgct    17280
cactgcccgc tttccagtcg ggaaacctgt cgtgccagct gcattaatga atcggccaac    17340
gcgcggggag aggcggtttg cgtattgggc gctcttccgc ttcctcgctc actgactcgc    17400
```

```
tgcgctcggt cgttcggctg cggcgagcgg tatcagctca ctcaaaggcg gtaatacggt   17460
tatccacaga atcaggggat aacgcaggaa agaacatgtg agcaaaaggc cagcaaaagg   17520
ccaggaaccg taaaaaggcc gcgttgctgg cgtttttcca taggctcggc ccccctgacg   17580
agcatcacaa aaatcgacgc tcaagtcaga ggtggcgaaa cccgacagga ctataaagat   17640
accaggcgtt ccccctgga agctccctcg tgcgctctcc tgttccgacc ctgccgctta   17700
ccggatacct gtccgccttt ctcccttcgg aagcgtggc gctttctcaa tgctcacgct   17760
gtaggtatct cagttcggtg taggtcgttc gctccaagct gggctgtgtg cacgaacccc   17820
ccgttcagcc cgaccgctgc gccttatccg gtaactatcg tcttgagtcc aacccggtaa   17880
gacacgactt atcgccactg gcagcagcca ctggtaacag gattagcaga gcgaggtatg   17940
taggcggtgc tacagagttc ttgaagtggt ggcctaacta cggctacact agaaggacag   18000
tatttggtat ctgcgctctg ctgaagccag ttaccttcgg aaaaagagtt ggtagctctt   18060
gatccggcaa acaaaccacc gctggtagcg gtggttttt tgtttgcaag cagcagatta   18120
cgcgcagaaa aaaaggatct caagaagatc ctttgatctt ttctacgggg tctgacgctc   18180
agtggaacga aaactcacgt taagggattt tggtcatgag attatcaaaa aggatcttca   18240
cctagatcct tttaaattaa aaatgaagtt ttaaatcaat ctaaagtata tatgagtaaa   18300
cttggtctga cagttaccaa tgcttaatca gtgaggcacc tatctcagcg atctgtctat   18360
ttcgttcatc catagttgcc tgactgcccg tcgtgtagat aactacgata cgggagggct   18420
taccatctgg ccccagtgct gcaatgatac cgcgagaccc acgctcaccg gctccagatt   18480
tatcagcaat aaaccagcca gccggaaggg ccgagcgcag aagtggtcct gcaactttat   18540
ccgcctccat ccagtctatt aattgttgcc gggaagctag agtaagtagt tcgccagtta   18600
atagtttgcg caacgttgtt gccattgcta caggcatcgt ggtgtcacgc tcgtcgtttg   18660
gtatggcttc attcagctcc ggttcccaac gatcaaggcg agttacatga tcccccatgt   18720
tgtgaaaaaa agcggttagc tccttcggtc ctccgatcgt tgtcagaagt aagttggccg   18780
cagtgttatc actcatgctt atggcagcac tgcataattc tcttactgtc atgccatccg   18840
taagatgctt ttctgtgact ggtgagtact caaccaagtc attctgagaa tagtgtatgc   18900
ggcgaccgag ttgctcttgc ccggcgtcaa tacgggataa taccgcgcca catagcagaa   18960
ctttaaaagt gctcatcatt ggaaaacgtt cttcggggcg aaaactctca aggatcttac   19020
cgctgttgag atccagttcg atgtaaccca ctcgtgcacc caactgatct tcagcatctt   19080
ttactttcac cagcgtttct gggtgagcaa aaacaggaag gcaaaatgcc gcaaaaaagg   19140
gaataagggc gacacggaaa tgttgaatac tcatactctt cctttttcaa tattattgaa   19200
gcatttatca gggttattgt ctcatgagcg gatacatatt tgaatgtatt tagaaaaata   19260
aacaaatagg ggttccgcgc acatttcccc gaaaagtgcc acctgaaatt gtaaacgtta   19320
atattttgtt aaaattcgcg ttaaattttt gttaaatcag ctcatttttt aaccaatagg   19380
ccgaaatcgg caaaatccct tataaatcaa aagaatagac cgagataggg ttgagtgttg   19440
ttccagtttg gaacaagagt ccactattaa agaacgtgga ctccaacgtc aaagggcgaa   19500
aaaccgtcta tcagggcgat ggcccactac gtgaaccatc accctaatca agttttttgg   19560
ggtcgaggtg ccgtaaagca ctaaatcgga acccctaaagg gagcccccga tttagagctt   19620
gacggggaaa gccggcgaac gtggcgagaa aggaagggaa gaaagcgaaa ggagcgggcg   19680
ctagggcgct ggcaagtgta gcggtcacgc tgcgcgtaac caccacaccc gccgcgctta   19740
```

-continued

```
atgcgccgct acagggcgcg tcccattcgc cattcaggct gcgcaactgt tgggaagggc  19800
gatcggtgcg ggcctcttcg ctattacgcc agccaccgcg gtg                     19843

<210> SEQ ID NO 2
<211> LENGTH: 19843
<212> TYPE: DNA
<213> ORGANISM: Artificial Sequence
<220> FEATURE:
<223> OTHER INFORMATION: Variant of pTM-MVSchw-deltaC-ATU1 (eGFP)
<220> FEATURE:
<221> NAME/KEY: mutation
<222> LOCATION: (2788)..(2788)
<223> OTHER INFORMATION: The T nucleotide of native MVSchw genome cDNA
      is replaced by a C nucleotide
<220> FEATURE:
<221> NAME/KEY: mutation
<222> LOCATION: (2803)..(2803)
<223> OTHER INFORMATION: The G nucleotide of native MVSchw genome cDNA
      is replaced by an A nucleotide

<400> SEQUENCE: 2
gcggccgcta atacgactca ctatagggcc aactttgttt ggtctgatga gtccgtgagg     60
acgaaacccg gagtcccggg tcaccaaaca aagttgggta aggatagttc aatcaatgat    120
catcttctag tgcacttagg attcaagatc ctattatcag ggacaagagc aggattaggg    180
atatccgaga cgcgtacgat ggtgagcaag ggcgaggagc tgttcaccgg ggtggtgccc    240
atcctggtcg agctggacgg cgacgtaaac ggccacaagt tcagcgtgtc cggcgagggc    300
gagggcgatg ccacctacgg caagctgacc ctgaagttca tctgcaccac cggcaagctg    360
cccgtgccct ggcccaccct cgtgaccacc ctgacctacg gcgtgcagtg cttcagccgc    420
taccccgacc acatgaagca gcacgacttc ttcaagtccg ccatgcccga aggctacgtc    480
caggagcgca ccatcttctt caaggacgac ggcaactaca agacccgcgc cgaggtgaag    540
ttcgagggcg acaccctggt gaaccgcatc gagctgaagg gcatcgactt caaggaggac    600
ggcaacatcc tggggcacaa gctggagtac aactacaaca gccacaacgt ctatatcatg    660
gccgacaagc agaagaacgg catcaaggtg aacttcaaga tccgccacaa catcgaggac    720
ggcagcgtgc agctcgccga ccactaccag cagaacaccc ccatcggcga cggccccgtg    780
ctgctgcccg acaaccacta cctgagcacc cagtccgccc tgagcaaaga ccccaacgag    840
aagcgcgatc acatggtcct gctggagttc gtgaccgccg ccgggatcac tctcggcatg    900
gacgagctgt acaagtaggc gcgcagcgct tagacgtctc gcgatcgatt agtgcgagag    960
gccgagggcc agaacaacat ccgcctacca tccatcattg ttataaaaaa cttaggattc   1020
aagatcctat tatcagggac aagagcagga ttagggatat ccgagatggc cacactttta   1080
aggagcttag cattgttcaa aagaaacaag gacaaaccac ccattacatc aggatccggt   1140
ggagccatca gaggaatcaa acacattatt atagtaccaa tccctggaga ttcctcaatt   1200
accactcgat ccagacttct ggaccggttg gtgaggttaa ttggaaaccc ggatgtgagc   1260
gggcccaaac taacaggggc actaataggt atattatcct tatttgtgga gtctccaggt   1320
caattgattc agaggatcac cgatgaccct gacgttagca taaggctgtt agaggttgtc   1380
cagagtgacc agtcacaatc tggccttacc ttcgcatcaa gaggtaccaa catggaggat   1440
gaggcggacc aatacttttc acatgatgat ccaattagta gtgatcaatc caggttcgga   1500
tggttcggga acaaggaaat ctcagatatt gaagtgcaag accctgaggg attcaacatg   1560
attctgggta ccatcctagc ccaaatttgg gtcttgctcg caaaggcggt tacggcccca   1620
gacacggcag ctgattcgga gctaagaagg tggataaagt acacccaaca aagaagggta   1680
```

```
gttggtgaat ttagattgga gagaaaatgg ttggatgtgg tgaggaacag gattgccgag    1740
gacctctcct tacgccgatt catggtcgct ctaatcctgg atatcaagag aacacccgga    1800
aacaaaccca ggattgctga aatgatatgt gacattgata catatatcgt agaggcagga    1860
ttagccagtt ttatcctgac tattaagttt gggatagaaa ctatgtatcc tgctcttgga    1920
ctgcatgaat tgctggtga gttatccaca cttgagtcct tgatgaacct ttaccagcaa     1980
atgggggaaa ctgcacccta catggtaatc tggagaaact caattcagaa caagttcagt    2040
gcaggatcat accctctgct ctggagctat gccatgggag taggagtgga acttgaaaac    2100
tccatgggag gtttgaactt tggccgatct tactttgatc cagcatattt tagattaggg    2160
caagagatgg taaggaggtc agctggaaag gtcagttcca cattggcatc tgaactcggt    2220
atcactgccg aggatgcaag gcttgtttca gagattgcaa tgcatactac tgaggacaag    2280
atcagtagag cggttggacc cagacaagcc caagtatcat ttctacacgg tgatcaaagt    2340
gagaatgagc taccgagatt gggggcaag gaagatagga gggtcaaaca gagtcgagga     2400
gaagccaggg agagctacag agaaaccggg cccagcagag caagtgatgc gagagctgcc    2460
catcttccaa ccggcacacc cctagacatt gacactgcaa cggagtccag ccaagatccg    2520
caggacagtc gaaggtcagc tgacgccctg cttaggctgc aagccatggc aggaatctcg    2580
gaagaacaag gctcagacac ggacacccct atagtgtaca atgacagaaa tcttctagac    2640
taggtgcgag aggccgaggg ccagaacaac atccgcctac catccatcat tgttataaaa    2700
aacttaggaa ccaggtccac acagccgcca gcccatcaac catccactcc cacgattgga    2760
gccaatggca gaagagcagg cacgccacgt caaaaacgga ctagaatgca tccgggctct    2820
caaggccgag cccatcggct cactggccat cgaggaagct atggcagcat ggtcagaaat    2880
atcagacaac ccaggacagg agcgagccac ctgcagggaa gagaaggcag gcagttcggg    2940
tctcagcaaa ccatgcctct cagcaattgg atcaactgaa ggcggtgcac ctcgcatccg    3000
cggtcaggga cctggagaga gcgatgacga cgctgaaact ttgggaatcc ccccaagaaa    3060
tctccaggca tcaagcactg ggttacagtg ttattacgtt tatgatcaca gcggtgaagc    3120
ggttaaggga atccaagatg ctgactctat catggttcaa tcaggccttg atggtgatag    3180
caccctctca ggaggagaca atgaatctga aaacagcgat gtggatattg gcgaacctga    3240
taccgaggga tatgctatca ctgaccgggg atctgctccc atctctatgg ggttcagggc    3300
ttctgatgtt gaaactgcag aaggagggga gatccacgag ctcctgagac tccaatccag    3360
aggcaacaac tttccgaagc ttgggaaaac tctcaatgtt cctccgcccc ggacccccgg    3420
tagggccagc acttccggga cacccattaa aaagggcaca gacgcgagat tagcctcatt    3480
tggaacggag atcgcgtctt tattgacagg tggtgcaacc caatgtgctc gaaagtcacc    3540
ctcggaacca tcagggccag gtgcacctgc ggggaatgtc cccgagtgtg tgagcaatgc    3600
cgcactgata caggagtgga cacccgaatc tggtaccaca atctcccga gatcccagaa     3660 taatgaagaa gggggagact attatgatga tgagctgttc tctgatgtcc aagatattaa    3720
aacagccttg gccaaaatac acgaggataa tcagaagata atctccaagc tagaatcact    3780
gctgttattg aaggagaag ttgagtcaat taagaagcag atcaacaggc aaaatatcag     3840
catatccacc ctggaaggac acctctcaag catcatgatc gccattcctg acttgggaa     3900 ggatcccaac gaccccactg cagatgtcga aatcaatccc gacttgaaac ccatcatagg    3960
cagagattca ggccgagcac tggccgaagt tctcaagaaa cccgttgcca gccgacaact    4020
```

```
ccaaggaatg acaaatggac ggaccagttc cagaggacag ctgctgaagg aatttcagct    4080
aaagccgatc gggaaaaaga tgagctcagc cgtcgggttt gttcctgaca ccggccctgc    4140
atcacgcagt gtaatccgct ccattataaa atccagccgg ctagaggagg atcggaagcg    4200
ttacctgatg actctccttg atgatatcaa aggagccaat gatcttgcca agttccacca    4260
gatgctgatg aagataataa tgaagtagct acagctcaac ttacctgcca accccatgcc    4320
agtcgaccca actagtacaa cctaaatcca ttataaaaaa cttaggagca aagtgattgc    4380
ctcccaaggt ccacaatgac agagacctac gacttcgaca agtcggcatg ggacatcaaa    4440
gggtcgatcg ctccgataca acccaccacc tacagtgatg gcaggctggt gccccaggtc    4500
agagtcatag atcctggtct aggcgacagg aaggatgaat gctttatgta catgtttctg    4560 ctggggggttg ttgaggacag cgattcccta gggcctccaa tcgggcgagc atttgggttc    4620
ctgcccttag gtgttggcag atccacagca aagcccgaaa aactcctcaa agaggccact    4680
gagcttgaca tagttgttag acgtacagca gggctcaatg aaaaactggt gttctacaac    4740 aacacccccac taactctcct cacaccttgg agaaaggtcc taacaacagg gagtgtcttc    4800
aacgcaaacc aagtgtgcaa tgcggttaat ctgataccgc tcgataccc gcagaggttc    4860 cgtgttgttt atatgagcat cacccgtctt tcggataacg ggtattacac cgttcctaga    4920
agaatgctgg aattcagatc ggtcaatgca gtggccttca acctgctggt gacccttagg    4980
attgacaagg cgataggccc tgggaagatc atcgacaata cagagcaact tcctgaggca    5040
acatttatgg tccacatcgg gaacttcagg agaaagaaga gtgaagtcta ctctgccgat    5100
tattgcaaaa tgaaaatcga aaagatgggc ctggtttttg cacttggtgg atagggggc    5160 accagtcttc acattagaag cacaggcaaa atgagcaaga ctctccatgc acaactcggg    5220
ttcaagaaga ccttatgtta cccgctgatg gatatcaatg aagaccttaa tcgattactc    5280
tggaggagca gatgcaagat agtaagaatc caggcagttt tgcagccatc agttcctcaa    5340
gaattccgca tttacgacga cgtgatcata aatgatgacc aaggactatt caaagttctg    5400
tagaccgtag tgcccagcaa tgcccgaaaa cgaccccct cacaatgaca gccagaaggc    5460
ccggacaaaa aagcccctc cgaaagactc cacggaccaa gcgagaggcc agccagcagc    5520
cgacggcaag cgcgaacacc aggcggcccc agcacagaac agccctgaca caaggccacc    5580
accagccacc ccaatctgca tcctcctcgt gggaccccg aggaccaacc cccaaggctg    5640
cccccgatcc aaaccaccaa ccgcatcccc accaccccg ggaaagaaac cccagcaat    5700 tggaaggccc ctccccctct tcctcaacac aagaactcca caaccgaacc gcacaagcga    5760
ccgaggtgac ccaaccgcag gcatccgact ccctagacag atcctctctc cccggcaaac    5820
taaacaaaac ttagggccaa ggaacataca cacccaacag aacccagacc ccggcccacg    5880
gcgccgcgcc cccaaccccc gacaaccaga gggagccccc aaccaatccc gccggctccc    5940
ccggtgccca caggcaggga caccaacccc gaacagacc cagcacccaa ccatcgacaa    6000
tccaagacgg gggggccccc ccaaaaaaag gcccccaggg gccgacagcc agcaccgcga    6060
ggaagcccac ccaccccaca cacgaccacg gcaaccaaac cagaacccag accaccctgg    6120
gccaccagct cccagactcg gccatcaccc cgcagaaagg aaaggccaca acccgcgcac    6180
cccagccccg atccggcggg gagccaccca acccgaacca gcacccaaga gcgatccccg    6240 aaggacccc gaaccgcaaa ggacatcagt atcccacagc ctctccaagt cccccggtct    6300
cctcctcttc tcgaagggac caaaagatca atccaccaca cccgacgaca ctcaactccc    6360 caccccctaaa ggagacaccg ggaatcccag aatcaagact catccaatgt ccatcatggg    6420
```

```
tctcaaggtg aacgtctctg ccatattcat ggcagtactg ttaactctcc aaacacccac    6480
cggtcaaatc cattggggca atctctctaa gataggggtg gtaggaatag gaagtgcaag    6540
ctacaaagtt atgactcgtt ccagccatca atcattagtc ataaaattaa tgcccaatat    6600
aactctcctc aataactgca cgagggtaga gattgcagaa tacaggagac tactgagaac    6660
agttttggaa ccaattagag atgcacttaa tgcaatgacc cagaatataa gaccggttca    6720
gagtgtagct tcaagtagga gacacaagag atttgcggga gtagtcctgg caggtgcggc    6780
cctaggcgtt gccacagctg ctcagataac agccggcatt gcacttcacc agtccatgct    6840
gaactctcaa gccatcgaca atctgagagc gagcctggaa actactaatc aggcaattga    6900
gacaatcaga caagcagggc aggagatgat attggctgtt cagggtgtcc aagactacat    6960
caataatgag ctgataccgt ctatgaacca actatcttgt gatttaatcg gccagaagct    7020
cgggctcaaa ttgctcagat actatacaga aatcctgtca ttatttggcc ccagtttacg    7080
ggaccccata tctgcggaga tatctatcca ggctttgagc tatgcgcttg gaggagacat    7140
caataaggtg ttagaaaagc tcggatacag tggaggtgat ttactgggca tcttagagag    7200
cggaggaata aaggcccgga taactcacgt cgacacagag tcctacttca ttgtcctcag    7260
tatagcctat ccgacgctgt ccgagattaa ggggtgatt gtccaccggc tagaggggt    7320 ctcgtacaac ataggctctc aagagtggta taccactgtg cccaagtatg ttgcaaccca    7380
agggtacctt atctcgaatt ttgatgagtc atcgtgtact ttcatgccag aggggactgt    7440
gtgcagccaa aatgccttgt acccgatgag tcctctgctc caagaatgcc tccgggggta    7500
caccaagtcc tgtgctcgta cactcgtatc cgggtctttt gggaaccggt tcattttatc    7560
acaagggaac ctaatagcca attgtgcatc aatccttgc aagtgttaca caacaggaac    7620
gatcattaat caagaccctg acaagatcct aacatacatt gctgccgatc actgcccggt    7680
agtcgaggtg aacggcgtga ccatccaagt cgggagcagg aggtatccag acgctgtgta    7740
cttgcacaga attgacctcg gtcctcccat atcattggag aggttggacg tagggacaaa    7800
tctggggaat gcaattgcta agttggagga tgccaaggaa ttgttggagt catcggacca    7860
gatattgagg agtatgaaag gtttatcgag cactagcata gtctacatcc tgattgcagt    7920
gtgtcttgga gggttgatag ggatccccgc tttaatatgt tgctgcaggg ggcgttgtaa    7980
caaaaaggga gaacaagttg gtatgtcaag accaggccta aagcctgatc ttacgggaac    8040
atcaaaatcc tatgtaaggt cgctctgatc ctctacaact cttgaaacac aaatgtccca    8100
caagtctcct cttcgtcatc aagcaaccac cgcacccagc atcaagccca cctgaaatta    8160
tctccggctt ccctctggcc gaacaatatc ggtagttaat caaaacttag ggtgcaagat    8220
catccacaat gtcaccacaa cgagaccgga taaatgcctt ctacaaagat aacccccatc    8280
ccaagggaag taggatagtc attaacagag aacatcttat gattgataga ccttatgttt    8340
tgctggctgt tctgtttgtc atgtttctga gcttgatcgg gttgctagcc attgcaggca    8400
ttagacttca tcgggcagcc atctacaccg cagagatcca taaagccctc agcaccaatc    8460
tagatgtaac taactcaatc gagcatcagg tcaaggacgt gctgacacca ctcttcaaaa    8520
tcatcggtga tgaagtgggc ctgaggacac ctcgagatt cactgaccta gtgaaattaa    8580
tctctgacaa gattaaattc cttaatccgg atagggagta cgacttcaga gatctcactt    8640
ggtgtatcaa cccgccagag agaatcaaat tggattatga tcaatactgt gcagatgtgg    8700
ctgctgaaga gctcatgaat gcattggtga actcaactct actggagacc agaacaacca    8760
```

```
atcagttcct agctgtctca aagggaaact gctcagggcc cactacaatc agaggtcaat    8820
tctcaaacat gtcgctgtcc ctgttagact tgtatttagg tcgaggttac aatgtgtcat    8880
ctatagtcac tatgacatcc cagggaatgt atggggaac ttacctagtg gaaaagccta     8940
atctgagcag caaaaggtca gagttgtcac aactgagcat gtaccgagtg tttgaagtag    9000
gtgttatcag aaatccgggt ttgggggctc cggtgttcca tatgacaaac tatcttgagc    9060
aaccagtcag taatgatctc agcaactgta tggtggcttt ggggagctc aaactcgcag     9120
cccttttgtca cggggaagat tctatcacaa ttccctatca gggatcaggg aaaggtgtca   9180
gcttccagct cgtcaagcta ggtgtctgga atccccaac cgacatgcaa tcctgggtcc     9240
ccttatcaac ggatgatcca gtgatagaca ggctttacct ctcatctcac agaggtgtta   9300
tcgctgacaa tcaagcaaaa tgggctgtcc cgacaacacg aacagatgac aagttgcgaa   9360
tggagacatg cttccaacag gcgtgtaagg gtaaaatcca agcactctgc gagaatcccg   9420
agtgggcacc attgaaggat aacaggattc cttcatacgg ggtcttgtct gttgatctga   9480
gtctgacagt tgagcttaaa atcaaaattg cttcgggatt cgggccattg atcacacacg   9540
gttcagggat ggacctatac aaatccaacc acaacaatgt gtattggctg actatcccgc   9600
caatgaagaa cctagcctta ggtgtaatca acacattgga gtggataccg agattcaagg   9660
ttagtcccta cctcttcact gtcccaatta aggaagcagg cgaagactgc catgccccaa   9720
catacctacc tgcggaggtg gatggtgatg tcaaactcag ttccaatctg gtgattctac   9780
ctggtcaaga tctccaatat gttttggcaa cctacgatac ttccagggtt gaacatgctg   9840
tggtttatta cgtttacagc ccaagccgct cattttctta cttttatcct tttaggttgc   9900
ctataaaggg ggtccccatc gaattacaag tggaatgctt cacatgggac caaaaactct   9960
ggtgccgtca cttctgtgtg cttgcggact cagaatctgg tggacatatc actcactctg  10020
ggatggtggg catgggagtc agctgcacag tcacccggga agatggaacc aatcgcagat  10080
agggctgcta gtgaaccaat cacatgatgt cacccagaca tcaggcatac ccactagtgt   10140
gaaatagaca tcagaattaa gaaaaacgta gggtccaagt ggttccccgt tatggactcg  10200
ctatctgtca accagatctt ataccctgaa gttcacctag atagcccgat agttaccaat  10260
aagatagtag ccatcctgga gtatgctcga gtccctcacg cttacagcct ggaggaccct  10320
acactgtgtc agaacatcaa gcaccgccta aaaaacggat tttccaacca aatgattata  10380
aacaatgtgg aagttgggaa tgtcatcaag tccaagctta ggagttatcc ggcccactct   10440
catattccat atccaaattg taatcaggat ttatttaaca tagaagacaa agagtcaacg   10500
aggaagatcc gtgaactcct caaaaagggg aattcgctgt actccaaagt cagtgataag  10560
gttttccaat gcttaaggga cactaactca cggcttggcc taggctccga attgagggag  10620
gacatcaagg agaaagttat taacttggga gtttacatgc acagctccca gtggtttgag  10680
cccttttctgt tttggtttac agtcaagact gagatgaggt cagtgattaa atcacaaacc  10740
catacttgcc ataggaggag acacacacct gtattcttca ctggtagttc agttgagttg  10800
ctaatctctc gtgaccttgt tgctataatc agtaaagagt ctcaacatgt atattacctg  10860
acatttgaac tggttttgat gtattgtgat gtcatagagg ggaggttaat gacagagacc  10920
gctatgacta ttgatgctag gtatacagag cttctaggaa gagtcagata catgtggaaa  10980
ctgatagatg gtttcttccc tgcactcggg aatccaactt atcaaattgt agccatgctg  11040
gagcctcttt cacttgctta cctgcagctg aggggatataa cagtagaact cagaggtgct  11100
ttccttaacc actgctttac tgaaatacat gatgttcttg accaaaacgg gttttctgat  11160
```

```
gaaggtactt atcatgagtt aactgaagct ctagattaca ttttcataac tgatgacata   11220
catctgacag gggagatttt ctcatttttc agaagtttcg gccacccag acttgaagca    11280
gtaacggctg ctgaaaatgt taggaaatac atgaatcagc ctaaagtcat tgtgtatgag   11340
actctgatga aaggtcatgc catattttgt ggaatcataa tcaacggcta tcgtgacagg   11400
cacggaggca gttggccacc gctgaccctc ccctgcatg ctgcagacac aatccggaat    11460
gctcaagctt caggtgaagg gttaacacat gagcagtgcg ttgataactg gaaatctttt   11520
gctggagtga aatttggctg ctttatgcct cttagcctgg atagtgatct gacaatgtac   11580
ctaaaggaca aggcacttgc tgctctccaa agggaatggg attcagttta cccgaaagag   11640
ttcctgcgtt acgaccctcc caagggaacc gggtcacgga ggcttgtaga tgttttcctt   11700
aatgattcga gctttgaccc atatgatgtg ataatgtatg ttgtaagtgg agcttacctc   11760
catgaccctg agttcaacct gtcttacagc ctgaaagaaa aggagatcaa ggaaacaggt   11820
agacttttg ctaaaatgac ttacaaaatg agggcatgcc aagtgattgc tgaaaatcta    11880
atctcaaacg ggattggcaa atattttaag gacaatggga tggccaagga tgagcacgat   11940
ttgactaagg cactccacac tctagctgtc tcaggagtcc ccaaagatct caaagaaagt   12000
cacaggggg ggccagtctt aaaaacctac tcccgaagcc cagtccacac aagtaccagg    12060
aacgtgagag cagcaaaagg gtttataggg ttccctcaag taattcggca ggaccaagac   12120
actgatcatc cggagaatat ggaagcttac gagacagtca gtgcatttat cacgactgat   12180
ctcaagaagt actgccttaa ttggagatat gagaccatca gcttgtttgc acagaggcta   12240
aatgagattt acggattgcc ctcattttc cagtggctgc ataagaggct tgagacctct     12300
gtcctgtatg taagtgaccc tcattgcccc cccgaccttg acgcccatat cccgttatat   12360
aaagtcccca atgatcaaat cttcattaag taccctatgg gaggtataga agggtattgt   12420
cagaagctgt ggaccatcag caccattccc tatctatacc tggctgctta tgagagcgga   12480
gtaaggattg cttcgttagt gcaagggac aatcagacca tagccgtaac aaaaagggta    12540
cccagcacat ggccctacaa ccttaagaaa cgggaagctg ctagagtaac tagagattac   12600
tttgtaattc ttaggcaaag gctacatgat attggccatc acctcaaggc aaatgagaca   12660
attgtttcat cacatttttt tgtctattca aaaggaatat attatgatgg gctacttgtg   12720
tcccaatcac tcaagagcat cgcaagatgt gtattctggt cagagactat agttgatgaa   12780
acaagggcag catgcagtaa tattgctaca acaatggcta aaagcatcga gagaggttat   12840
gaccgttacc ttgcatattc cctgaacgtc ctaaaagtga tacagcaaat tctgatctct   12900
cttggcttca caatcaattc aaccatgacc cgggatgtag tcatacccct cctcacaaac   12960
aacgacctct taataaggat ggcactgttg cccgctccta ttgggggat gaattatctg    13020
aatatgagca ggctgtttgt cagaaacatc ggtgatccag taacatcatc aattgctgat   13080
ctcaagagaa tgattctcgc ctcactaatg cctgaagaga ccctccatca agtaatgaca   13140
caacaaccgg gggactcttc attcctagac tgggctagcg accttactc agcaaatctt    13200
gtatgtgtcc agagcatcac tagactcctc aagaacataa ctcaaggtt tgtcctgatc    13260
catagtccaa acccaatgtt aaaaggatta ttcatgatg acagtaaaga agaggacgag    13320
ggactggcgg cattcctcat ggacaggcat attatagtac ctagggcagc tcatgaaatc   13380
ctggatcata tgtcacagg gcaagagag tctattgcag gcatgctgga taccacaaaa    13440
ggcttgattc gagccagcat gaggaagggg gggttaacct ctcgagtgat aaccagattg   13500
```

```
tccaattatg actatgaaca attcagagca gggatggtgc tattgacagg aagaaagaga    13560
aatgtcctca ttgacaaaga gtcatgttca gtgcagctgg cgagagctct aagaagccat    13620
atgtgggcga ggctagctcg aggacggcct atttacggcc ttgaggtccc tgatgtacta    13680
gaatctatgc gaggccacct tattcggcgt catgagacat gtgtcatctg cgagtgtgga    13740
tcagtcaact acggatggtt ttttgtcccc tcggttgcc aactggatga tattgacaag     13800
gaaacatcat ccttgagagt cccatatatt ggttctacca ctgatgagag aacagacatg    13860
aagcttgcct tcgtaagagc cccaagtcga tccttgcgat ctgctgttag aatagcaaca    13920
gtgtactcat gggcttacgg tgatgatgat agctcttgga acgaagcctg gttgttggct    13980
aggcaaaggg ccaatgtgag cctggaggag ctaagggtga tcactcccat ctcaacttcg    14040
actaatttag cgcataggtt gagggatcgt agcactcaag tgaaatactc aggtacatcc    14100
cttgtccgag tggcgaggta taccacaatc tccaacgaca atctctcatt tgtcatatca    14160
gataagaagg ttgatactaa ctttatatac caacaaggaa tgcttctagg gttgggtgtt    14220
ttagaaacat tgtttcgact cgagaaagat accggatcat ctaacacggt attacatctt    14280
cacgtcgaaa cagattgttg cgtgatcccg atgatagatc atcccaggat acccagctcc    14340
cgcaagctag agctgagggc agagctatgt accaacccat tgatatatga taatgcacct    14400
ttaattgaca gagatgcaac aaggctatac acccagagcc ataggaggca ccttgtggaa    14460
tttgttacat ggtccacacc ccaactatat cacattttag ctaagtccac agcactatct    14520
atgattgacc tggtaacaaa atttgagaag gaccatatga atgaaatttc agctctcata    14580
ggggatgacg atatcaatag tttcataact gagtttctgc tcatagagcc aagattattc    14640
actatctact tgggccagtg tgcggccatc aattgggcat tgatgtaca ttatcataga     14700 ccatcaggga aatatcagat gggtgagctg ttgtcatcgt tccttttctag aatgagcaaa    14760 ggagtgttta aggtgcttgt caatgctcta agccacccaa agatctacaa gaaattctgg    14820
cattgtggta ttatagagcc tatccatggt ccttcacttg atgctcaaaa cttgcacaca    14880
actgtgtgca acatggttta cacatgctat atgacctacc tcgacctgtt gttgaatgaa    14940
gagttagaag agttcacatt tctcttgtgt gaaagcgacg aggatgtagt accggacaga    15000
ttcgacaaca tccaggcaaa acacttatgt gttctggcag atttgtactg tcaaccaggg    15060
acctgcccac caattcgagg tctaagaccg gtagagaaat gtgcagttct aaccgaccat    15120
atcaaggcag aggctatgtt atctccagca ggatcttcgt ggaacataaa tccaattatt    15180
gtagaccatt actcatgctc tctgacttat ctccggcgag gatcgatcaa acagataaga    15240
ttgagagttg atccaggatt catttttcgac gccctcgctg aggtaaatgt cagtcagcca    15300
aagatcggca gcaacaacat ctcaaatatg agcatcaagg ctttcagacc cccacacgat    15360
gatgttgcaa aattgctcaa agatatcaac acaagcaagc acaatcttcc catttcaggg    15420
ggcaatctcg ccaattatga atccatgct ttccgcagaa tcgggttgaa ctcatctgct     15480
tgctacaaag ctgttgagat atcaacatta attaggagat gccttgagcc aggggaggac    15540
ggcttgttct tgggtgaggg atcgggttct atgttgatca cttataaaga gatacttaaa    15600
ctaaacaagt gcttctataa tagtgggggtt tccgccaatt ctagatctgg tcaaagggaa    15660
ttagcaccct atccctccga agttggcctt gtcgaacaca gaatgggagt aggtaatatt    15720
gtcaaagtgc tctttaacgg gagggcccgaa gtcacgtggg taggcagtgt agattgcttc    15780
aatttcatag ttagtaatat ccctacctct agtgtggggt ttatccattc agatatagag    15840
accttgcctg acaaagatac tatagagaag ctagaggaat tggcagccat cttatcgatg    15900
```

```
gctctgctcc tgggcaaaat aggatcaata ctggtgatta agcttatgcc tttcagcggg   15960
gattttgttc agggatttat aagttatgta gggtctcatt atagagaagt gaaccttgta   16020
taccctagat acagcaactt catctctact gaatcttatt tggttatgac agatctcaag   16080
gctaaccggc taatgaatcc tgaaaagatt aagcagcaga taattgaatc atctgtgagg   16140
acttcacctg gacttatagg tcacatccta tccattaagc aactaagctg catacaagca   16200
attgtgggag acgcagttag tagaggtgat atcaatccta ctctgaaaaa acttacacct   16260
atagagcagg tgctgatcaa ttgcgggttg gcaattaacg gacctaagct gtgcaaagaa   16320
ttgatccacc atgatgttgc ctcagggcaa gatggattgc ttaattctat actcatcctc   16380
tacagggagt tggcaagatt caaagacaac caagaagtc aacaagggat gttccacgct    16440 tacccccgtat tggtaagtag caggcaacga gaacttatat ctaggatcac ccgcaaattc   16500
tgggggcaca ttcttcttta ctccgggaac aaaaagttga taaataagtt tatccagaat   16560
ctcaagtccg gctatctgat actagactta caccagaata tcttcgttaa gaatctatcc   16620
aagtcagaga aacagattat tatgacgggg ggtttgaaac gtgagtgggt ttttaaggta   16680
acagtcaagg agaccaaaga atggtataag ttagtcggat acagtgccct gattaaggac   16740
taattggttg aactccggaa ccctaatcct gccctaggtg gttaggcatt atttgcaata   16800
tattaaagaa aactttgaaa atacgaagtt ctattccca gctttgtctg gtggccggca    16860
tggtcccagc ctcctcgctg gcgccggctg ggcaacattc gaggggacc gtcccctcgg    16920 taatggcgaa tgggacgcgg ccgatccggc tgctaacaaa gcccgaaagg aagctgagtt   16980
ggctgctgcc accgctgagc aataactagc ataacccctt ggggcctcta aacgggtctt   17040
gaggggtttt ttgctgaaag gaggaactat atccggatgc ggccgcgggc cctatggtac   17100
ccagcttttg ttccctttag tgagggttaa ttccgagctt ggcgtaatca tggtcatagc   17160
tgtttcctgt gtgaaattgt tatccgctca caattccaca caacatagga gccggaagca   17220
taaagtgtaa agcctggggt gcctaatgag tgaggtaact cacattaatt gcgttgcgct   17280
cactgcccgc tttccagtcg ggaaacctgt cgtgccagct gcattaatga atcggccaac   17340
gcgcggggag aggcggtttg cgtattgggc gctcttccgc ttcctcgctc actgactcgc   17400
tgcgctcggt cgttcggctg cggcgagcgg tatcagctca ctcaaaggcg gtaatacggt   17460
tatccacaga atcaggggat aacgcaggaa agaacatgtg agcaaaaggc cagcaaaagg   17520
ccaggaaccg taaaaaggcc gcgttgctgg cgttttttcca taggctcggc cccccctgacg   17580 agcatcacaa aaatcgacgc tcaagtcaga ggtggcgaaa cccgacagga ctataaagat   17640
accaggcgtt ccccccctgga agctccctcg tgcgctctcc tgttccgacc ctgccgctta   17700
ccggatacct gtccgccttt ctcccttcgg aagcgtggc gctttctcaa tgctcacgct    17760
gtaggtatct cagttcggtg taggtcgttc gctccaagct gggctgtgtg cacgaacccc   17820
ccgttcagcc cgaccgctgc gccttatccg gtaactatcg tcttgagtcc aacccggtaa   17880
gacacgactt atcgccactg gcagcagcca ctggtaacag gattagcaga gcgaggtatg   17940
taggcggtgc tacagagttc ttgaagtggt ggcctaacta cggctacact agaaggacag   18000
tatttggtat ctgcgctctg ctgaagccag ttaccttcgg aaaaagagtt ggtagctctt   18060
gatccggcaa acaaaccacc gctggtagcg gtggtttttt tgtttgcaag cagcagatta   18120
cgcgcagaaa aaaaggatct caagaagatc ctttgatctt ttctacgggg tctgacgctc   18180
agtggaacga aaactcacgt taagggattt tggtcatgag attatcaaaa aggatcttca   18240
```

-continued

```
cctagatcct tttaaattaa aaatgaagtt ttaaatcaat ctaaagtata tatgagtaaa    18300
cttggtctga cagttaccaa tgcttaatca gtgaggcacc tatctcagcg atctgtctat    18360
ttcgttcatc catagttgcc tgactgcccg tcgtgtagat aactacgata cgggagggct    18420
taccatctgg ccccagtgct gcaatgatac cgcgagaccc acgctcaccg gctccagatt    18480
tatcagcaat aaaccagcca gccggaaggg ccgagcgcag aagtggtcct gcaactttat    18540
ccgcctccat ccagtctatt aattgttgcc gggaagctag agtaagtagt cgccagtta    18600 atagtttgcg caacgttgtt gccattgcta caggcatcgt ggtgtcacgc tcgtcgtttg    18660
gtatggcttc attcagctcc ggttcccaac gatcaaggcg agttacatga tcccccatgt    18720
tgtgaaaaaa agcggttagc tccttcggtc ctccgatcgt tgtcagaagt aagttggccg    18780
cagtgttatc actcatgctt atggcagcac tgcataattc tcttactgtc atgccatccg    18840
taagatgctt ttctgtgact ggtgagtact caaccaagtc attctgagaa tagtgtatgc    18900
ggcgaccgag ttgctcttgc ccggcgtcaa tacgggataa taccgcgcca catagcagaa    18960
ctttaaaagt gctcatcatt ggaaaacgtt cttcggggcg aaaactctca aggatcttac    19020
cgctgttgag atccagttcg atgtaaccca ctcgtgcacc caactgatct tcagcatctt    19080
ttactttcac cagcgtttct gggtgagcaa aaacaggaag gcaaaatgcc gcaaaaaagg    19140
gaataagggc gacacggaaa tgttgaatac tcatactctt ccttttttcaa tattattgaa    19200 gcatttatca gggttattgt ctcatgagcg gatacatatt tgaatgtatt tagaaaaata    19260
aacaaatagg ggttccgcgc acatttcccc gaaaagtgcc acctgaaatt gtaaacgtta    19320
atattttgtt aaaattcgcg ttaaattttt gttaaatcag ctcattttttt aaccaatagg    19380 ccgaaatcgg caaaatccct tataaatcaa agaatagac cgagataggg ttgagtgttg    19440
ttccagtttg gaacaagagt ccactattaa agaacgtgga ctccaacgtc aaagggcgaa    19500
aaaccgtcta tcagggcgat ggcccactac gtgaaccatc accctaatca agttttttgg    19560
ggtcgaggtg ccgtaaagca ctaaatcgga accctaaagg gagcccccga tttagagctt    19620
gacggggaaa gccggcgaac gtggcgagaa aggaagggaa gaaagcgaaa ggagcgggcg    19680
ctagggcgct ggcaagtgta gcggtcacgc tgcgcgtaac caccacaccc gccgcgctta    19740
atgcgccgct acagggcgcg tcccattcgc cattcaggct gcgcaactgt tgggaagggc    19800
gatcggtgcg ggcctcttcg ctattacgcc agccaccgcg gtg                     19843
```

<210> SEQ ID NO 3  
<211> LENGTH: 47  
<212> TYPE: DNA  
<213> ORGANISM: Artificial Sequence  
<220> FEATURE:  
<223> OTHER INFORMATION: Portion of the nucleotide sequence of MVSchw genome cDNA showing part of the P and C ORFs
<400> SEQUENCE: 3

```
atggcagaag agcaggcacg ccatgtcaaa aacggactgg aatgcat              47
```

<210> SEQ ID NO 4  
<211> LENGTH: 47  
<212> TYPE: DNA  
<213> ORGANISM: Artificial Sequence  
<220> FEATURE:  
<223> OTHER INFORMATION: Portion of the nucleotide sequence of MVSchw-deltaC genome cDNA  
<220> FEATURE:  
<221

```
                                                                  is replaced by a C nucleotide

<400> SEQUENCE: 4
atggcagaag agcaggcacg ccacgtcaaa aacggactgg aatgcat                47

<210> SEQ ID NO 5
<211> LENGTH: 47
<212> TYPE: DNA
<213> ORGANISM: Artificial Sequence
<220> FEATURE:
<223> OTHER INFORMATION: Portion of the nucleotide sequence of MVSchw-
      deltaC genome cDNA
<220> FEATURE:
<221> NAME/KEY: mutation
<222> LOCATION: (24)..(24)
<223> OTHER INFORMATION: The T nucleotide of native MVSchw genome cDNA
      is replaced by a C nucleotide
<220> FEATURE:
<221> NAME/KEY: mutation
<222> LOCATION: (39)..(39)
<223> OTHER INFORMATION: The G nucleotide of native MVSchw genome cDNA
      is replaced by an A nucleotide

<400> SEQUENCE: 5
atggcagaag agcaggcacg ccacgtcaaa aacggactag aatgcat                47
```